United States Patent
Loktionov et al.

(10) Patent No.: US 10,001,492 B2
(45) Date of Patent: *Jun. 19, 2018

(54) METHOD FOR DIAGNOSING INFLAMMATORY BOWEL DISEASE

(71) Applicant: DiagNodus Limited, Babraham, Cambridgeshire (GB)

(72) Inventors: Alexandre Loktionov, Cambridge (GB); Tatiana Bandaletova, Cambridge (GB)

(73) Assignee: Diagnodus Limited (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/035,004

(22) PCT Filed: Nov. 7, 2013

(86) PCT No.: PCT/GB2013/052935
§ 371 (c)(1),
(2) Date: May 6, 2016

(87) PCT Pub. No.: WO2015/067913
PCT Pub. Date: May 14, 2015

(65) Prior Publication Data
US 2016/0266147 A1   Sep. 15, 2016

Related U.S. Application Data

(63) Continuation-in-part of application No. 14/115,529, filed as application No. PCT/GB2012/050964 on May 3, 2012, now Pat. No. 9,448,145.

(30) Foreign Application Priority Data

May 5, 2011 (GB) .................................. 1107466.3

(51) Int. Cl.
*G01N 33/68* (2006.01)
(52) U.S. Cl.
CPC ... *G01N 33/6893* (2013.01); *G01N 2800/065* (2013.01)

(58) Field of Classification Search
CPC ......... G01N 33/6893; G01N 2800/065; G01N 33/50; G01N 33/53
See application file for complete search history.

(56) References Cited

U.S. PATENT DOCUMENTS

| | | | | |
|---|---|---|---|---|
| 5,928,883 A | * | 7/1999 | Gleich | C12Q 1/28 435/28 |
| 7,608,414 B2 | * | 10/2009 | Dotan | G01N 33/569 435/255.2 |
| 7,875,431 B2 | * | 1/2011 | Diehl | C12Q 1/6883 435/6.17 |
| 9,448,145 B2 | * | 9/2016 | Loktionov | G01N 33/5044 |

FOREIGN PATENT DOCUMENTS

WO    2012150453 A1    11/2012

OTHER PUBLICATIONS

Van Der Vekiens et al., Human and equine cardiovascular endocrinology: beware to compare, Cardiovascular Endocrinology 2013, vol. 2, No. 4, pp. 67-76.*
Torzewski et al., Animal Models of C-Reactive Protein, Hindawl Publishing Corporation, Mediators of Inflammation, vol. 2014, Article ID 683598, 2014, pp. 1-7.*
Michael Wagner et al., "Fecal Markers of Inflammation Used as Surrogate Markers for Treatment Outcome in Relapsing Inflammatory Bowel Disease", World Journal of Gastroenterology, Sep. 28, 2008, pp. 5584-5589.
Seung-Woo Shin et al., "Elevation of Eosinophil-Derived Neurotoxin in Plasma of the Subjects with Aspirin-Exacerbated Respiratory Disease: A Possible Peripheral Blood Protein Biomarker", PLOS ONE, Jun. 2013, vol. 8, Issue 6.

\* cited by examiner

*Primary Examiner* — Gary Counts
(74) *Attorney, Agent, or Firm* — Tarolli, Sundheim, Covell & Tummino LLP

(57) ABSTRACT

The present invention relates to a method for diagnosing inflammatory bowel disease (IBD), the method comprising determining the concentration of at least one IBD-specific biomarker in a sample of the colonic mucocellular layer obtained from a subject.

15 Claims, 27 Drawing Sheets

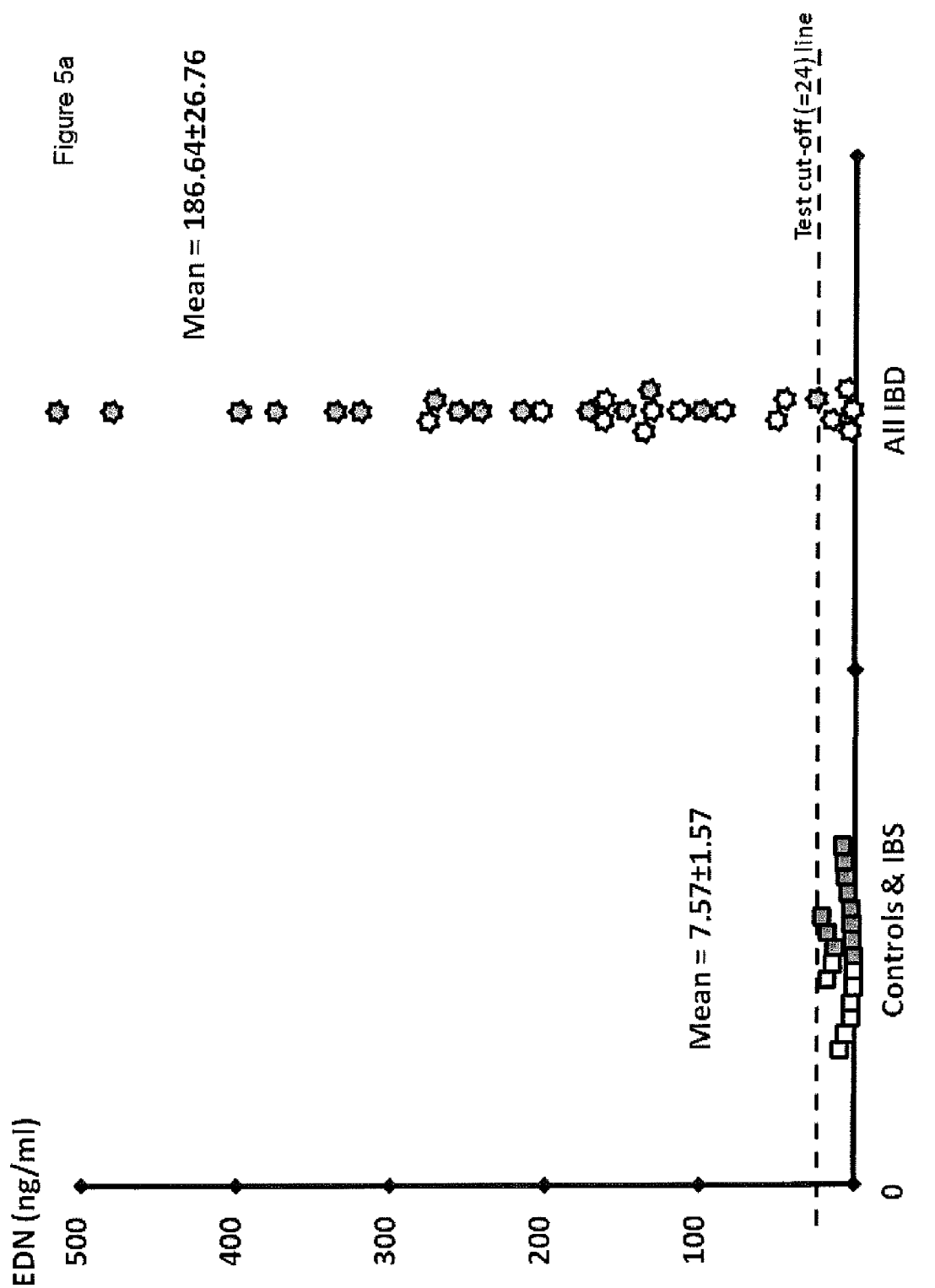

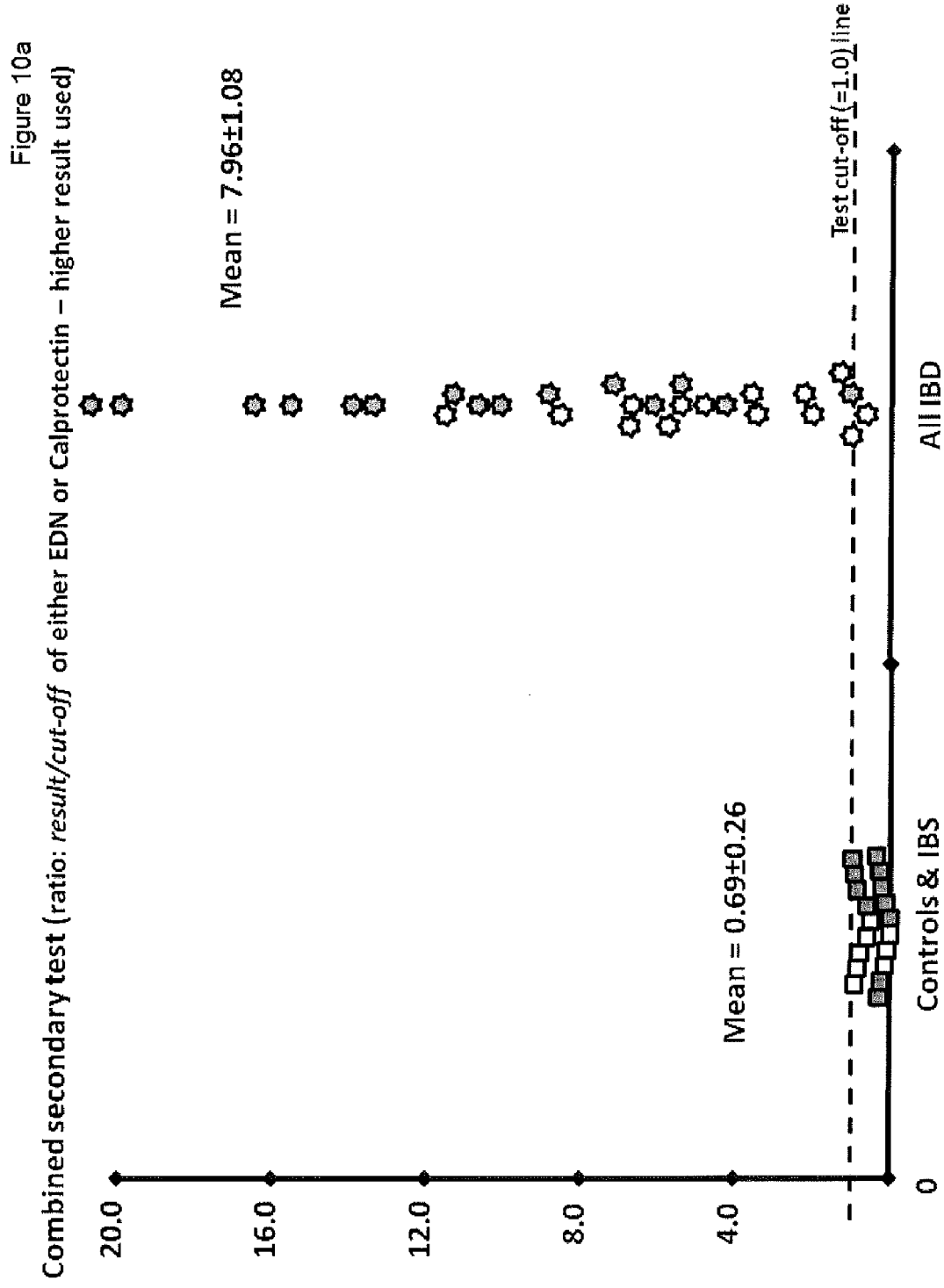

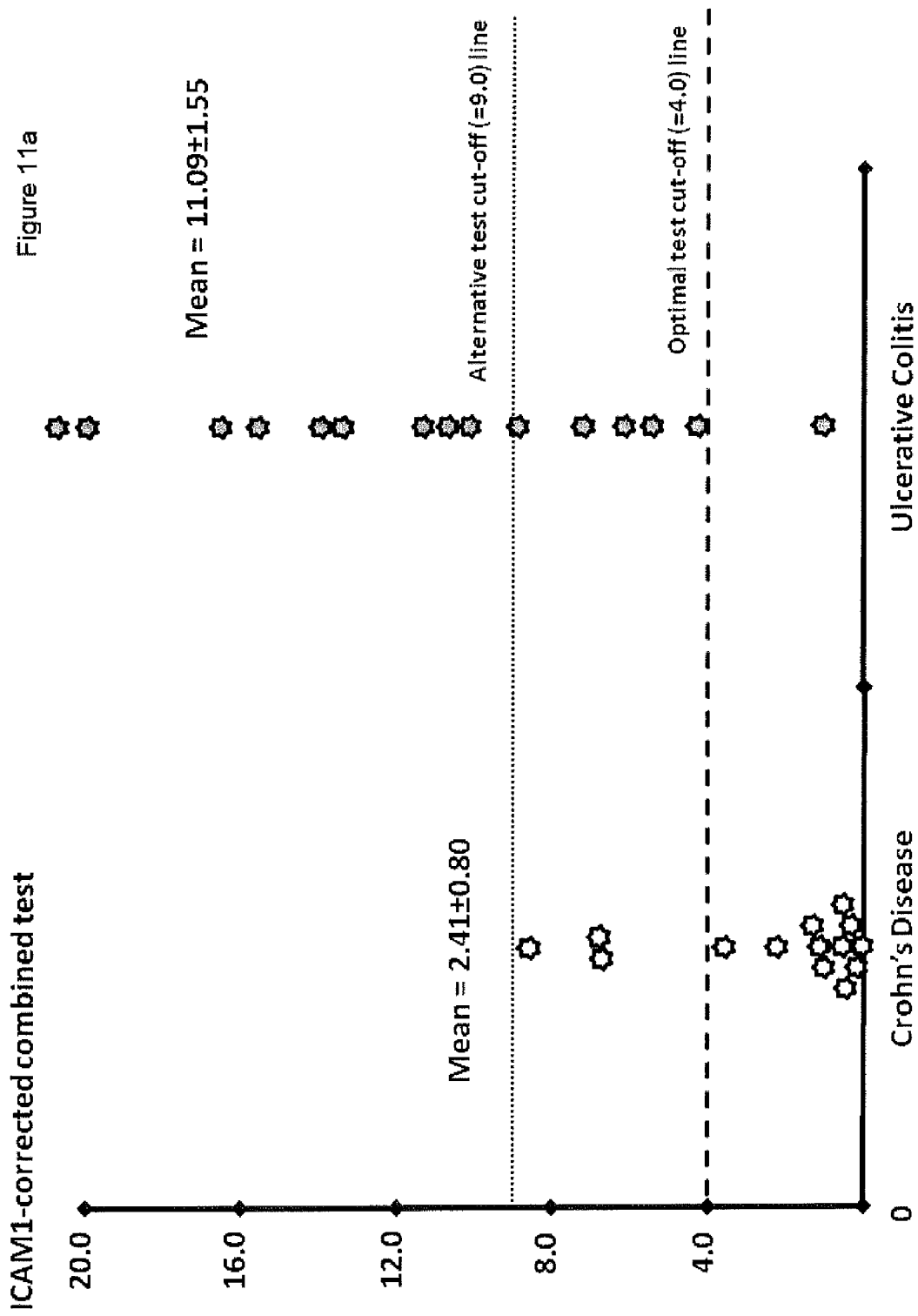

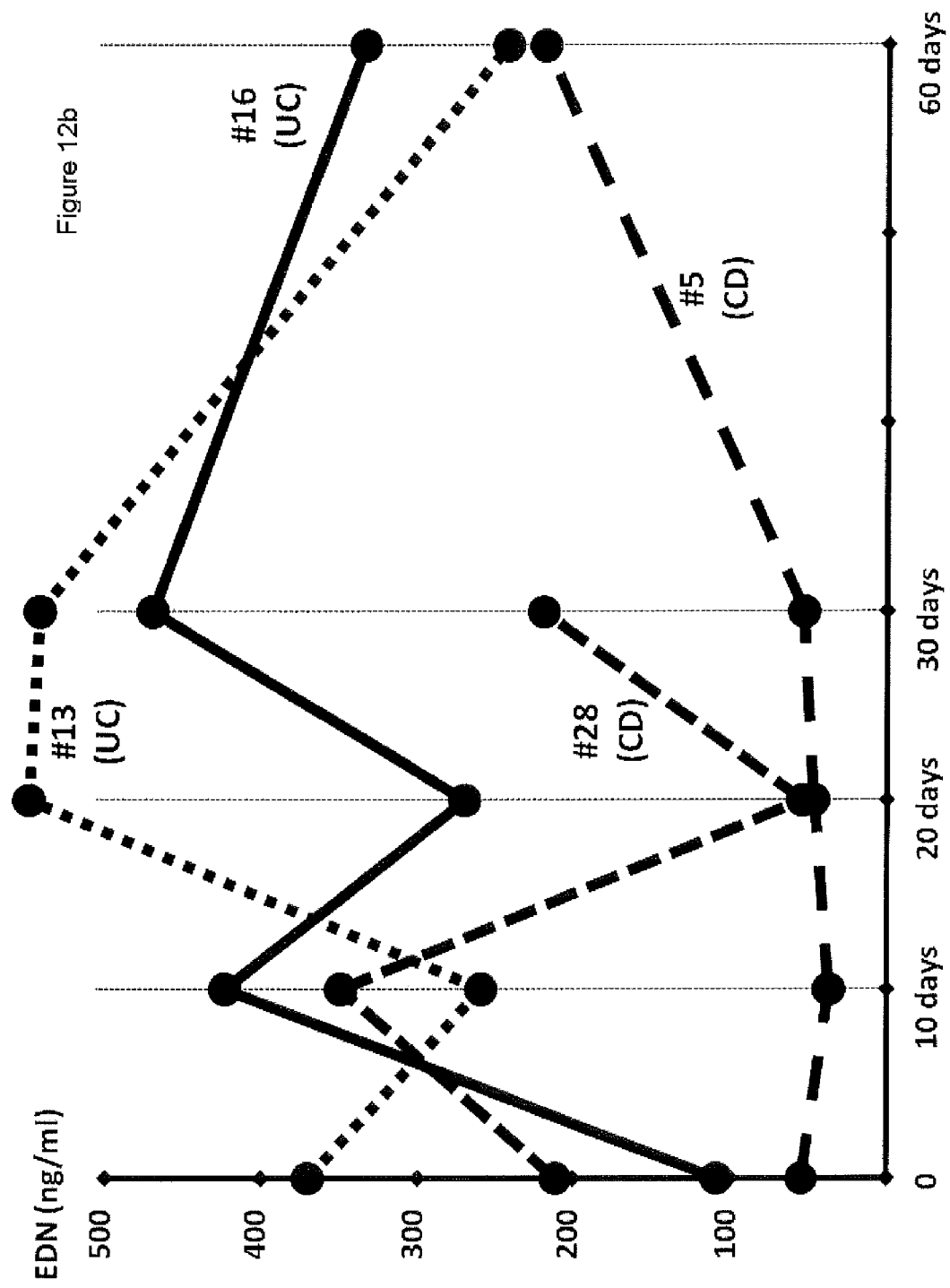

METHOD FOR DIAGNOSING INFLAMMATORY BOWEL DISEASE

RELATED APPLICATIONS

The present application is a U.S. National Stage application under 35 USC 371, claiming priority to International patent application Serial No. PCT/GB2013/052935, filed on Nov. 7, 2013. The present application is also a Continuation-in-Part of U.S. patent application Ser. No. 14/115,529, filed Jan. 21, 2014, which is a U.S. National Stage application under 35 USC 371, claiming priority to International patent application Serial No. PCT/GB2012/050964, filed on May 3, 2012, which claims priority from GB 1107466.3 filed on May 5, 2011. All of the aforementioned applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Nov. 11, 2013, is named sequence listing 7.11.13 (4526563-1).txt and is 9 KB in size.

FIELD OF THE INVENTION

The present invention relates to methods for diagnosing inflammatory bowel disease (IBD), such as ulcerative colitis (UC) or Crohn's disease (CD) and assessing intestinal inflammation intensity by measuring the amount of an IBD-specific biomarker(s) in a sample of colorectal mucocellular layer non-invasively collected from the surface of the anal area of a human subject following the natural act of defaecation. Simultaneous quantitative evaluation of several biomarkers in samples of human colorectal mucocellular layer provides additional methods for IBD monitoring, assessing effectiveness of applied therapy and individually selecting specific therapeutic modalities for IBD patients. The invention also provides a method for distinguishing between UC and Crohn's disease.

BACKGROUND OF THE INVENTION

Inflammatory bowel disease (IBD) is a group of common chronic disorders involving bowel inflammation. Ulcerative colitis (UC) and Crohn's disease (CD) are the most important conditions of this group. IBD is usually diagnosed in young adults. In most cases it is characterized by long remissions and incidental disabling flare-ups usually requiring treatment.

Currently there are about 2.4 million IBD patients in the EU and over 1.3 million in the US (Cosnes et al., 2011). The incidence and prevalence of the disease continue to grow (Molodecky et al, 2012). Once diagnosed, all IBD patients should be monitored for a possible relapse. Those developing relapses are treated, and treatment efficiency assessment is an important task in need of serious improvements. Differentiation between IBD and non-inflammatory diarrhoeas, such as Irritable Bowel Syndrome (IBS) constitutes another major problem, especially given that IBS affects 10-15% of the adult population in most developed Western countries (Agarwal & Whorwell, 2006; Khan & Chang, 2010).

IBD diagnosis confirmation usually requires colonoscopy, an efficient diagnostic procedure that is, however, highly invasive, expensive and can sometimes cause dangerous complications. Repeated colonoscopies in IBD patients may be dangerous; therefore currently IBD activity and therapy efficiency are usually assessed by disease activity indexes based on severity of clinical manifestations and results of indirect laboratory analyses (Satsangi et al, 2006). Colonoscopy is also widely used to differentiate between IBD and common functional conditions such as IBS.

Development of biomarker-based non-invasive diagnostic tests for IBD is generally recognised as an urgent problem, solution of which can help in addressing multiple important endpoints comprising: a) primary diagnosis of IBD and its differentiation from other conditions; b) differentiation between UC and CD; c) complication risk assessment; d) distinction between active IBD and remission; e) assessment of colonic mucosa damage and healing; f) IBD relapse prediction; g) Prediction of response to specific therapy and treatment choice; h) therapy efficiency monitoring and therapeutic adjustments (Lewis, 2011). Recent progress in biomarker use for these endpoints is reflected in numerous scientific publications and abundant patent literature. The main approaches can be roughly divided into methods employing non-colonic tissue or body fluids (especially blood/serum) and those using materials obtained directly from the colon, such as stool, colonic biopsy samples, and colonic lavage. The existing prior art is briefly outlined below.

The role of genetic factors in the pathogenesis of both UC (Louis et al, 2009) and CD (Weersma et al, 2009; Tamboli et al, 2011) is well known. There is a group of patent documents describing genetic markers for IBD diagnosis, often presented as complex multimarker panels exemplified by a family of patents by Harris and Alsobrook (U.S. Pat. Nos. 7,833,720; 7,833,721; 7,879,553; 7,923,544; 8,222,390; 8,227,589). Methods detecting single gene variants associated with IBD (WO03/052412) or specifically with CD (U.S. Pat. Nos. 6,001,569; 6,534,263) were also proposed. Determination of IBD-related changes in the human gut microbiome is the main element of another genotyping-based technique (US Pat. App. No. 2013/0045874). Other relevant patents using genetic markers describe approaches targeting changes in microRNAs (WO94/21662; US Pat App. Nos. 2011/0117111; 2013/0143764) and various gene expression profiles (U.S. Pat. Nos. 7,875,431; 8,257,923; US Pat. App. Nos. 2009/0155788; 2009/0186034; 2009/0311260; 2010/0267575; 2011/0082188; EP1462527). However, genetic approaches have not provided a clinically applicable method so far, being mostly confined to the prediction of Crohn's disease risk (Weersma et al, 2009) and assessment of pharmacogenetics of drugs used for its treatment (Roberts & Barclay, 2012). In addition to limited diagnostic efficiency, most of these methods are exceedingly technically complex.

The use of protein biomarkers defines another major group of original approaches to IBD diagnosis. Several existing patents describe diagnostic methods employing biomarkers of this type detectable in serum. Detection of perinuclear anti-neutrophil cytoplasmic antibodies (pANCA) associated with UC and CD-associated anti-*saccharomyces cerevisiae* antibodies (ASCA) constitutes an important component of most techniques using serum samples, however various additional markers were also considered (Peyrin-Biroulet et al, 2007). A number of multimarker methods proposed for human serum samples combines pANCA and/or ASCA with either multiple protein biomarkers of human or bacterial origin (U.S. Pat. Nos. 6,218,129; 7,608,414 7,759,079; 7,873,479; 8,315,818; 8,445,215; 8,463,553; US Pat. App. Nos. 2006/0154276;

2010/0015156; 2010/0021455; 2010/0129838; 2010/0254971; 2010/0255513; WO2005/009339) or additional genetic markers (US Pat. App. Nos. 2011/0229471; 2012/0171672; 2013/0203053; 2013/0225439). Some basically similar techniques for IBD detection using serum samples do not include pANCA or ASCA, being focused on other bacterial (U.S. Pat. Nos. 7,361,733; 7,993,865; 7,993,866; 7,993,867; 8,318,901; US Pat. App. Nos. 2007/0275424; 2011/0251100; WO2009/135257; WO2011/130546) or human (U.S. Pat. No. 7,358,058; US Pat. App. No. 2009/0258848) proteins associated with gut inflammation, in particular inflammatory cytokines (US Pat. App. Nos. 2010/0316992; 2012/0258883; WO2012/037199). In addition to ASCA, antibodies to GP2 (a membrane glycoprotein known to be expressed in the exocrine part of the pancreas) have recently been suggested as a new marker for CD (Somma et al, 2013). Other proposed techniques are designed to detect diagnostically informative subtypes of circulating monocytes (WO2012/172347), specific T-cell-associated molecules (U.S. Pat. No. 7,989,173) or goblet cell antigen elevated in UC patients (US Pat. App. No. 2008/0293625). In addition, methods determining oligosaccharide ratio changes in IgG (U.S. Pat. No. 8,043,832), assessing complex metabolite (over 100 small molecules) profiles (US Pat. App. No. 2012/0003158) or measuring antibodies against a range of dietary components (US Pat. App. No. 2012/0058497) were published. Although the outlined peripheral blood or serological marker panels may potentially be useful for differentiating UC from CD, disease monitoring and defining therapeutic strategies (Peyrin-Biroulet et al, 2007), they do not perform better than non-specific C-reactive protein (Palmon et al, 2008). None of them is currently applied for practical clinical use. Another major group of biomarker-based approaches in the area of IBD is related to analysing samples directly derived from the gastrointestinal tract. Prior art of this type deserves special attention since the present invention belongs to this group.

The idea of using colonic tissue for IBD testing could certainly be applied to invasively obtained tissue (biopsy) samples (U.S. Pat. No. 7,972,807; Us Pat. App. Nos. 2004/132110; 2009/0305267), but stool sample analysis appears to be the most frequently used approach. A range of marker proteins detectable in stool samples obtained from IBD patients was investigated in this context (reviewed by Foell et al, 2009 and Lewis, 2011). The principal candidates were proteins found in neutrophil granules, in particular calprotectin, lactoferrin, S100A12 protein, dimeric pyruvate kinase, polymorphonuclear elastase, myeloperoxidase and human neutrophil lipocalin (Foell et al, 2009; Lewis, 2011; Sherwood, 2012). Among them calprotectin detection in stool samples using ELISA assay developed and patented by Fagerhol et al (U.S. Pat. No. 5,455,160) was extensively investigated and provided the most consistent results (van Rheenen et al, 2010; Lewis, 2011). This calprotectin assay has recently been improved as described in US Pat. App. No. 2013/132347. A rapid calprotectin test for faecal samples has also been devised (WO2012/052586). Stool calprotectin quantification is the only biomarker-based test for IBD detection recommended for clinical use and currently employed by some clinicians (Sherwood, 2012).

Several patents by Boon et al describe IBD detection and differentiation from IBS using lactoferrin analysis in stool samples (U.S. Pat. Nos. 7,192,724; 7,560,240; 7,892,762). The same group also proposed methods for distinguishing between UC and CD that employed detection in faeces of already mentioned ASCA (U.S. Pat. No. 6,872,540) or pANCA (U.S. Pat. No. 7,736,858), alone or in combination with lactoferrin quantification (U.S. Pat. No. 7,785,818). In other publications lactoferrin test was combined with neopterin detection (US Pat. App. No. 2012/0258477) or with assays for several protein biomarkers comprising calprotectin and a group of interleukins (US Pat. App. No. 2011/0212104). At the same time lactoferrin quantification in stool was also proposed for colorectal cancer diagnosis (U.S. Pat. No. 5,552,292). In general IBD detection or differentiation between IBD and IBS using lactoferrin determination in faeces appeared to be less efficient than stool calprotectin assay (Sherwood, 2012).

Although information on S100A12 protein diagnostic performance for IBD detection is relatively scarce compared to calprotectin and lactoferrin, there are reports indicating that quantitative testing of stool samples for S100A12 may provide better results than calprotectin analysis (Kaiser et al, 2007), especially in children (de Jong et al, 2006; Sidler et al, 2008). Nevertheless, an attempt to use this marker for paediatric UC monitoring was not successful (Turner et al, 2010). In the absence of large clinical studies introduction of faecal S100A12 test into healthcare practice remains questionable (Sherwood, 2012). The lack of information on this biomarker is reflected in the available patent literature. The only relevant patent applications identified were US Pat. App. 2010/0311758 describing the use of S100A12 (alternatively called Calgranulin C) for diagnosing a wide range of inflammatory diseases and US Pat. App. No. 2009/0286328 proposing faecal S100A12 detection for colorectal cancer diagnosis. Dymeric pyruvate kinase (M2-PK), which was initially regarded as colorectal cancer marker detectable in stool samples (Hardt et al, 2004) has also emerged as a potential faecal marker for IBD (Jeffery et al, 2009; Turner et al, 2010). An ELISA assay for M2-PK is described in U.S. Pat. No. 5,972,628 and its variant for the protein detection in stool samples in U.S. Pat. No. 7,226,751. However, M2-PK is not applied in clinical practice.

Polymorphonuclear elastase is another enzyme present in neutrophils, which was proposed as a candidate IBD biomarker (Langhorst et al, 2008; Foell et al, 2009). Although an immunoassay for this protein exists (U.S. Pat. No. 6,124,107), it is not regarded as a potential clinical test.

Some authors also suggested that inflammation-related neutrophil degranulation can be detected in stool samples by quantifying myeloperoxidase (Wagner et al, 2008; Masoodi et al, 2011) and human neutrophil lipocalin (Nielsen et al, 1996, 1999), but these tests are not sufficiently studied to be proposed for IBD detection.

Proteins associated with eosinophils, such as eosinophil cationic protein and eosin-derived neurotoxin (EDN) can also be detected in stool, but they were usually described as faecal markers of intestinal hypersensitivity and eosinophilic inflammation (Foell et al, 2009). The eosinophil-derived neurotoxin (EDN, also called Eosinophil Protein X) is a multifunctional protein possessing ribonuclease activity (Rosenberg, 2008). It is known to be a marker of eosinophil presence and degranulation, and its elevated amounts in stool samples were reported to correlate with allergic reactions (Majamaa et al, 1999; Magnusson et al, 2003). Although some authors described elevated EDN in stool being associated with the presence of inflammation (Bischoff et al, 1997; Saitoh et al, 1999; Peterson et al, 2002; Wagner et al, 2008), these observations were inconclusive. Increased EDN values were also reported in colorectal perfusion fluid (Carlson et al, 1999) and material collected from the surface of the rectal mucosa using an inflatable intrarectal device (Anderson et al, 2011; the collecting device was described in US Pat. App. 2008/0097238). The latter two studies, however, assessed very few IBD cases. In a patent by Gleich and Levy (U.S. Pat. No. 5,928,883) EDN was proposed as one of eosinopil granule proteins (alongside eosinophil peroxidase), combined determination of which in whole gut lavage liquid could be used for IBD diagnosis. On the basis of the existing published evidence faecal EDN was not regarded as a promising biomarker of IBD, being less reliable than calprotectin or other stool biomarkers (Wagner et al, 2008; Foell et al, 2009). EDN was never considered as an IBD biomarker suitable for clinical use.

Several inflammatory cytokines were also proposed as potential biomarkers of IBD (Foell et al, 2009). Tumour necrosis factor alpha (TNFα), a small peptide predominantly produced by activated macrophages, could be a very good candidate, being a recognised therapeutic target in IBD patients (Danese et al, 2013). Although immunoassays for TNFα exist (e.g. U.S. Pat. Nos. 5,223,395; 5,436,154; 7,285,269), the protein is unstable in stool samples (Foell et al, 2009). This constitutes a serious obstacle for using it for diagnostic purposes.

Additional biomarkers that are not derived from inflammatory cells can also be informative in the context of IBD diagnosis and monitoring. For example it is generally accepted that cell adhesion molecules (CAMs) are closely involved in leukocyte trafficking constituting a major mechanism in inflammatory process (Springer, 1995). Among them, intercellular adhesion molecule-1 (ICAM-1) is known to play an especially important role in the development of IBD inflammatory bowel disease (Vainer, 2010). Detection of a common polymorphism in the gene encoding ICAM-1 appears to correlate with IBD risk and was previously proposed as an approach to genetic screening for predisposition to IBD development (U.S. Pat. Nos. 5,681,699; 6,008,335; 6,884,590). In addition, specific inhibition of ICAM-1 expression has recently been proposed as an approach to IBD treatment (Miner et al, 2006; Vainer, 2010). All available information regarding ICAM-1 presence in the colonic mucosa is limited by descriptive morphological observations from biopsy samples (Vainer, 2010), whereas it has never been quantified in either mucosal or stool samples.

Assessment of the degree of epithelial damage and its healing during convalescence constitutes another important aspect in the context of IBD. Soluble cytokeratin 18 (CK-18) is known to be released from epithelial cells following their death (Ueno et al, 2005). Although the presence of CK-18 in stool samples has never been investigated, elevated levels of this protein were once reported in samples obtained intrarectally from a few IBD patients (Anderson et al, 2011).

D-dimer is a small protein fragment generated during cross-linked fibrin degradation (Pabinger & Ay, 2009). Its increased presence can indicate chronic bleeding that is a common phenomenon in many IBD patients. Increased D-dimer levels in plasma samples from IBD patients were previously observed (Kume et al, 2007), but little was known on D-dimer changes in the gut. This biomarker could also be measured in intrarectally collected material (Anderson et al, 2011). D-dimer measurement might be informative for assessing intestinal inflammation severity and bleeding-related complication risk.

Some authors proposed using measurements of total human DNA in stool for IBD monitoring (Casellas et al, 2007), however the efficiency of this approach needs further evaluation. Finally, patent literature search allowed identifying less promising stool tests based upon the determination of intestinal 0-glycans (US Pat. App. No. 2009/0311707), HMGB1 protein (US Pat. App. No. 2013/0137123) and COX-2 protein (U.S. Pat. No. 7,220,825).

The presented background information shows that despite the availability of a number of potentially promising biomarkers of intestinal inflammation the field is still poorly developed. The only clinically employed biomarker-based test for IBD is stool calprotectin detection, the applicability of which is considerably limited due to the necessity of stool collection and handling. Presently there is no reliable alternative non-invasive test for IBD.

We have previously devised a new method of non-invasive collection of excreted colonic mucocellular layer (Loktionov, 2007) material from the anal area following natural bowel opening (WO2012/150453). This simple procedure based on sample self-collection provides material containing highly informative cells in abundance and can be easily applied to a range of biomarker detection-based diagnostic and monitoring applications in the area of colorectal disease. We have applied the new collection technique and tested a range of potential biomarkers in samples obtained from IBD patients and controls.

For convenience, a list of references cited herein follows:

U.S. PATENT DOCUMENTS

| | | |
|---|---|---|
| 4,816,567 | March 1989 | Cabilly et al. |
| 5,223,395 | June 1993 | Gero |
| 5,436,154 | July 1995 | Barbanti et al. |
| 5,455,160 | October 1995 | Fagerhol et al. |
| 5,545,806 | August 1996 | Lonberg et al. |
| 5,552,292 | September 1996 | Uchida et al. |
| 5,569,825 | October 1996 | Lonberg et al. |
| 5,625,126 | April 1997 | Lonberg et al. |
| 5,633,425 | May 1997 | Lonberg et al. |
| 5,661,016 | July 1997 | Lonberg et al. |
| 5,681,699 | October 1997 | Rotter et al. |
| 5,928,883 | July 1999 | Gleich et al. |
| 5,972,628 | October 1999 | Eigenbrodt et al. |
| 6,001,569 | December 1999 | Plevy et al. |
| 6,008,335 | December 1999 | Rotter et al. |
| 6,124,107 | September 2000 | Humes et al. |
| 6,187,546 | February 2001 | O'Neill et al. |
| 6,218,129 | April 2001 | Walsh et al. |
| 6,534,263 | March 2003 | Plevy et al. |
| 6,872,540 | March 2005 | Boone et al. |
| 6,884,590 | April 2005 | Rotter et al. |
| 7,192,724 | March 2007 | Boone et al. |
| 7,220,825 | May 2007 | Nair |
| 7,226,751 | June 2007 | Eigenbrodt et al. |
| 7,285,269 | October 2007 | Babcock et al. |
| 7,358,058 | April 2008 | Bergmann et al. |
| 7,361,733 | April 2008 | Hershberg et al. |
| 7,560,240 | July 2009 | Boone et al. |
| 7,608,414 | October 2009 | Dotan et al. |
| 7,736,858 | June 2010 | Boone et al. |
| 7,759,079 | July 2010 | Oh et al. |
| 7,785,818 | August 2010 | Boone et al. |
| 7,833,720 | November 2010 | Harris et al. |
| 7,833,721 | November 2010 | Harris et al. |
| 7,873,479 | January 2011 | Lois et al. |
| 7,875,431 | January 2011 | Diehl et al. |
| 7,879,553 | February 2011 | Harris et al. |
| 7,892,762 | February 2011 | Boone et al. |
| 7,923,544 | April 2011 | Harris et al. |
| 7,972,807 | July 2011 | Phanstiel et al. |
| 7,989,173 | August 2011 | Chen |
| 7,993,865 | August 2011 | Targan et al. |
| 7,993,866 | August 2011 | Targan et al. |
| 7,993,867 | August 2011 | Targan et al. |
| 8,043,832 | October 2011 | Miyoshi et al. |
| 8,222,390 | July 2012 | Harris et al. |
| 8,227,589 | July 2012 | Harris et al. |
| 8,257,923 | September 2012 | Diehl et al. |
| 8,315,818 | November 2012 | Lois et al. |
| 8,317,728 | November 2012 | Triva |
| 8,318,901 | November 2012 | Hershberg et al. |

| 8,445,215 | May 2013 | Wang et al. |
| 8,463,553 | June 2013 | Lois et al. |

U.S. PATENT APPLICATIONS

| US2004/0132110 | July 2004 | Desreumaux et al. |
| US2006/0154276 | July 2006 | Lois et al. |
| US2007/0275424 | November 2007 | Gewirtz et al. |
| US2008/0097238 | April 2008 | Loktionov et al. |
| US2008/0293625 | November 2008 | Stocker et al. |
| US2009/0155788 | June 2009 | Abbas et al. |
| US2009/0186034 | July 2009 | Abbas et al. |
| US2009/0258848 | October 2009 | Chakravarti et al. |
| US2009/0286328 | November 2009 | Wild et al. |
| US2009/0305267 | December 2009 | Krause et al. |
| US2009/0311260 | December 2009 | Goddard et al. |
| US2009/0311707 | December 2009 | Xia |
| US2010/0015156 | January 2010 | Dubinsky et al. |
| US2010/0021455 | January 2010 | Targan et al. |
| US2010/0129838 | May 2010 | Barken |
| US2010/0254971 | October 2010 | Dotan et al. |
| US2010/0255513 | October 2010 | Denson et al. |
| US2010/0267575 | October 2010 | Xu et al. |
| US2010/0311758 | December 2010 | Roth et al. |
| US2010/0316992 | December 2010 | Debad et al. |
| US2011/0082188 | April 2011 | Chakravarti |
| US2011/0117111 | May 2011 | Kwon et al. |
| US2011/0212104 | September 2011 | Beaumont et al. |
| US2011/0229471 | September 2011 | Rotter et al. |
| US2011/0251100 | October 2011 | Li et al. |
| US2012/0003158 | January 2012 | Alexander et al. |
| US2012/0058497 | March 2012 | Suga et al. |
| US2012/0171672 | July 2012 | Barken et al. |
| US2012/0258477 | October 2012 | Buchman |
| US2012/0258883 | October 2012 | Chappell et al. |
| US2013/0045874 | February 2013 | Ehrlich |
| US2013/0137123 | May 2013 | Cucchiara et al. |
| US2013/0143764 | June 2013 | Ogier-Denis et al. |
| US2013/0203053 | August 2013 | Princen et al. |
| US2013/0225439 | August 2013 | Princen et al. |
| US2013/132347 | September 2013 | Mørk et al. |

OTHER PATENT DOCUMENTS

| WO94/04690 | March 1994 | Ashkenazi et al. |
| WO94/21662 | September 1994 | Altman et al. |
| WO97/34631 | September 1997 | Ward |
| WO03/052412 | June 2003 | Allen et al. |
| EP1462527 | September 2004 | Costello et al. |
| WO2009/135257 | November 2009 | Radford-Smith |
| WO2011/130546 | October 2011 | Norman |
| WO2012/037199 | March 2012 | Li et al. |
| WO2012/0525860 | April 2012 | Genzor et al. |
| WO2012/150453 | July 2012 | Loktionov et al. |
| WO2012/172347 | December 2012 | Winqvist et al. |

OTHER PUBLICATIONS

Agarwal & Whorwell (2006) BMJ 332: 280-283.
Anderson et al. (2011) Int J Colorectal Dis 26: 1287-1297.
Bandaletova et al. (2002) APMIS 110: 239-246.
Bischoff et al. (1997) Dig Dis Sci 42: 394-403.
Carlson et al. (1999) Am J Gastroenterol 94: 1876-83.
Carter et al. (1992) Nat Biotechnol 10: 163-167.
Carter et al. (1995) J Hematotherapy 4: 463-470.
Casellas et al. (2007) Inflamm Bowel Dis 13: 386-390.
Clackson et al. (1991) Nature 352: 624-628.
Cole et al. (1985) in Monoclonal Antibodies and Cancer Therapy, Alan R. Liss, Inc. NY: pp. 77-96.
Cosnes et al. (2011) Gastroenterology 140: 1785-1794.
Danese et al. (2013) Aliment Pharmacol Ther 37: 855-866.
De Jong et al. (2006) Inflamm Bowel Dis 12: 566-572.
Foell et al. (2009) Gut 58: 859-868.
Hardt et al. (2004) Br J Cancer 91: 980-984.
Holliger & Hudson (2005) Nat Biotechnol 23: 1126-1136.
Jefferey et al. (2009) Inflamm Bowel Dis 15: 1630-1634.
Kabat (1980) J Immunol 125: 961-969.
Kabat et al (1992) Sequences of Proteins of Immunological Interest. 5-th edition. NIH, Bthesda, Md.: 2719p.
Kaiser et al. (2007) Gut 56: 1706-1713.
Khan & Chang (2010) Nat Rev Gastroenterol Hepatol 7: 565-581.
Kohler & Milstein (1995) Nature 256: 495-497.
Kozbor & Roder (1983) Immunol Today 4: 72-79.
Langhorst et al. (2008) Am J Gastroenterol 103: 162-169.
Lewis (2011) Gastroenterology 140: 1817-1826.
Linnet (1985) Clin Chem 31: 574-580
Loktionov (2007) Int J Cancer 120: 2281-2289.
Loktionov et al. (1998) Clin Ca Res 4: 337-342.
Loktionov et al. (2009) Int J Oncol 34: 301-311.
Loktionov et al. (2010) Int J Cancer 126: 1910-1919.
Lonberg & Huszar (1995) Int Rev Immunol 13: 65-93.
Louis et al. (2009) Gut 58: 1173-1176.
Magnusson et al. (2003) Clin Exp Allergy 33: 1052-1059.
Majamaa et al. (1999) Clin Exp Allergy 29: 1502-1506.
Marks et al. (1991) J Mol Biol 222: 581-597.
Masoodi et al. (2011) Ger Med Sci 9: Doc3.
Merchant et al. (1998) Nat Biotechnol 16: 677-681.
Miner et al. (2006) Aliment Pharmacol Ther 23: 1403-1413.
Molodecky et al. (2012) Gastroenterology 142: 46-54.
Nielsen et al. (1996) Gut 38: 414-420.
Nielsen et al. (1999) Am J Gastroenterol 94: 2923-2928.
Pabunger & Ay (2009) Atheroscl Thromb Vasc Biol 29: 332-336.
Palmon et al. (2008) Inflamm Bowel Dis 14: 5187-5189.
Peterson et al. (2002) Am J Gastroenterol 97: 1755-1762.
Peyrin-Biroulet et al. (2007) Inflamm Bowel Dis 13: 1561-1566.
Roberts & Barclay (2012) J Gastroenterol Hepatol 27: 1546-1554.
Rodrigues et al. (1993) J Immunol 151: 6954-6961.
Rosenberg (2008) Curr Pharm Biotechnol 9: 135-140.
Saitoh et al. (1999) Am J Gastroenterol 94: 3513-3520.
Satsangi et al. (2006) Gut 55: 749-753.
Sherwood (2012) J Clin Pathol 65: 981-985.
Sidler et al. (2008) Inflamm Bowel Dis 14: 359-366.
Somma et al. (2013) Gastroenterol Res Pract 2013: 683824.
Springer (1995) Annu Rev Physiol 57: 827-872.
Suresh et al. (1986) Methods Enzymol 121: 210-228.
Tamboli et al. (2011) Clin Experim Gastroenterol 4: 127-140.
Turner et al. (2010) Gut 59: 1207-1212.
Ueno et al. (2005) Biomed Pharmacother 59: S359-S362.
Vainer (2010) APMIS 118 (Suppl 129): 1-46.
van Rheenen et al. (2010) BMJ 341: c3369.
Wagner et al. (2008) World J Gastroenterol 14: 5584-5589.
Weersma et al. (2009) Gut 58: 388-395.

SUMMARY OF THE INVENTION

In a first aspect of the invention there is provided a method for diagnosing an inflammatory bowel disease (IBD), the method comprising determining the concentration of at least one IBD-specific biomarker, or a fragment or variant thereof, in a sample of the colonic mucocellular layer obtained from a subject, wherein the sample is obtained from the surface of the anal area following defaecation, comparing said concentration to a threshold value and determining that the subject has IBD when the concentration of at least one IBD-specific biomarker is said sample is equal to or greater than the threshold value.

In an alternative embodiment, the sample is an intestinal mucocellular layer. Alternatively, the sample may be a sample originating from the internal surface of the bowel.

In a preferred embodiment, the sample is taken from the anal area in the vicinity of the exterior opening of the anal canal.

In one embodiment the at least one IBD-specific biomarker is selected from the group consisting of eosinophil-derived neurotoxin (EDN), calprotectin, S100A12, ICAM1, CK-18, D-dimer, TNF-α, ASCA, pANCA, anti-GP2 antibodies, lactoferrin and total amount of human DNA in the sample or a combination thereof. The IBD-specific biomarker may also be a cytokine, alone or in combination with another IBD-specific biomarker.

In one embodiment, the IBD-specific biomarker is EDN and the threshold value is (or is equivalent to) between 15 ng/ml and 35 ng/ml when the (collected) sample is lysed in 3 ml of lysis buffer. In an alternative embodiment, the IBD-specific biomarker is calprotectin and the threshold value is or is equivalent to between 3.5 µg/ml and 6.0 µg/ml when the collected sample is lysed in 3 ml of lysis buffer. In a further alternative embodiment the IBD-specific biomarker is S100A12 and the threshold value is or is equivalent to 50 ng/ml when the collected sample is lysed in 3 ml of lysis buffer. In a further alternative embodiment the IBD-specific biomarker is ICAM1 and the threshold value is or is equivalent to 150 pg/ml when the collected sample is lysed in 3 ml of lysis buffer.

In an another embodiment, the IBD-specific biomarker is EDN the threshold value is, or is equivalent to, 15 ng/ml when the collected sample is lysed in 3 ml of lysis buffer. In an alternative embodiment, the IBD-specific biomarker is calprotectin and the threshold value is, or is equivalent to, 3.5 µg/ml when the collected sample is lysed in 3 ml of lysis buffer.

In one embodiment the concentration of the IBD-specific biomarker is determined by contacting the sample with at least one antibody capable of specifically binding the IBD-specific biomarker or a fragment or variant thereof.

In a second aspect of the invention there is provided a method for diagnosing an inflammatory bowel disease (IBD), the method comprising determining the concentration of the EDN protein, or a fragment or variant thereof, in a sample of the colonic mucocellular layer obtained from a subject, and determining that the subject has IBD when the concentration of EDN is, or is equivalent to a value, equal to or greater than 15 ng/ml when the collected sample is lysed in 3 ml of lysis buffer.

In a third aspect of the invention there is provided a method for diagnosing an inflammatory bowel disease (IBD), the method comprising determining the concentration of the calprotectin protein, or a fragment or variant thereof, in a sample of the colonic mucocellular layer obtained from a subject and determining that the subject has IBD when the concentration of calprotectin is, or is equivalent to a value, equal to or greater than 3.5 µg/ml when the collected sample is lysed in 3 ml of lysis buffer.

In one embodiment of the methods described herein, the method comprises determining that the subject has IBD when the concentration of EDN is, or is equivalent to a value, equal to or greater than 24 ng/ml when the collected sample is lysed in 3 ml of lysis buffer. In an alternative embodiment the concentration of EDN is, or is equivalent to a value, equal to or greater than 35 ng/ml when the collected sample is lysed in 3 ml of lysis buffer. In a further alternative embodiment, the concentration of EDN is, or is equivalent to a value, equal to or greater than a concentration value within the range 15 ng/ml to 35 ng/ml when the collected sample is lysed in 3 ml of lysis buffer.

In another embodiment of the methods described herein, the method comprises determining that the subject has IBD when the concentration of calprotectin is, or is equivalent to a value, equal to or more than 4.7 µg/ml when the collected sample is lysed in 3 ml of lysis buffer. In an alternative embodiment, the concentration of calprotectin is, or is equivalent to a value, equal to or more than 6.0 µg/ml when the collected sample is lysed in 3 ml of lysis buffer. In a further alternative embodiment, the concentration of calprotectin is, or is equivalent to a value, equal to or greater than a concentration value within the range 3.5 µg/ml and 6.0 µg/ml when the collected sample is lysed in 3 ml of lysis buffer.

In a fourth aspect of the invention there is provided a method for monitoring the effectiveness of a treatment for IBD the method comprising determining the concentration of at least one IBD-specific biomarker, or a fragment or variant thereof, in a sample of the colonic mucocellular layer obtained from a subject, wherein the sample is obtained from the surface of the anal area following defaecation, comparing said concentration to a threshold value and determining that the treatment is effective when the concentration of at least one IBD-specific biomarker is said sample is less than the threshold value.

In one embodiment the IBD-specific biomarker is EDN the threshold value is, or is equivalent to, between 35-120 ng/ml when the collected sample is lysed in 3 ml of lysis buffer. In a further embodiment, the threshold value is, or is equivalent to, less than 100 ng/ml when the collected sample is lysed in 3 ml of lysis buffer.

In an alternative embodiment, the IBD-specific biomarker is calprotectin and the threshold value is, or is equivalent to, between 6.0 and 10.0 µg/ml when the collected sample is lysed in 3 ml of lysis buffer. In a further embodiment, the threshold value is, or is equivalent to a value, less than 7.5 µg/ml when the collected sample is lysed in 3 ml of lysis buffer.

In a fifth aspect of the invention there is provided a method for monitoring the effectiveness of a treatment for IBD, the method comprising determining the concentration of the EDN protein, or a fragment or variant thereof, in a sample of the colonic mucocellular layer obtained from a subject post-treatment, and determining that the treatment is effective when the concentration of EDN is, or is equivalent to, less than a value between 35-120 ng/ml, when the collected sample is lysed in 3 ml of lysis buffer. In a preferred embodiment, the concentration of the EDN protein, or a fragment or variant thereof is measured at at least two time points post-treatment and the method comprises determining that the treatment is effective when the concentration of EDN at at least one time point (preferably the later time point) is, or is equivalent to, less than a value between 35-120 ng/ml, when the collected sample is lysed in 3 ml of lysis buffer. In a further alternative embodiment, the concentration of EDN is, or is equivalent to, less than 100 ng/ml when the collected sample is lysed in 3 ml of lysis buffer.

In a further aspect of the invention there is provided a method for monitoring the effectiveness of a treatment for IBD, the method comprising determining the concentration of the calprotectin protein, or a fragment or variant thereof, in a sample of the colonic mucocellular layer obtained from a subject post-treatment, and determining that the treatment is effective when the concentration of calprotectin is, or is equivalent to, less than a value between 6.0 and 10.0 µg/ml when the collected sample is lysed in 3 ml of lysis buffer. In a preferred embodiment, the concentration of the calprotectin protein, or a fragment or variant thereof is measured at at least two time points post-treatment and the method comprises determining that the treatment is effective when the concentration of calprotectin at at least one time point (preferably the later time point) is, or is equivalent to, less than a value between 6.0 and 10.0 µg/ml when the collected sample is lysed in 3 ml of lysis buffer. In a further alternative embodiment, the concentration of calprotectin is, or is equivalent to a value, less than 7.5 µg/ml when the collected sample is lysed in 3 ml of lysis buffer.

In an alternative embodiment, monitoring the effectiveness of a treatment for IBD comprises determining the concentration of the EDN protein and/or calprotectin protein, or a fragment or variant thereof, in a sample of the colonic mucocellular layer obtained from a subject pre and at least one time point post-treatment and determining that the treatment is ineffective when the concentration of EDN and/or calprotectin in the at least one post-treatment sample is equivalent to or greater than the concentration in the pre-treatment sample. In a preferred embodiment the treatment is ineffective when the concentration in the post-treatment sample is, or is equivalent to, a value equal to or greater than a value between 35-120 ng/ml for EDN and between 6.0 and 10.0 µg/ml for calprotectin when the collected sample is lysed in 3 ml of lysis buffer. In a preferred embodiment, the concentration of the EDN protein and/or calprotectin protein, or a fragment or variant thereof is measured at at least two time points post-treatment and the method comprises determining that the treatment is ineffective when the concentration of EDN and/or calprotectin is, or is equivalent to a value, equal to or greater than a value between 35-120 ng/ml for EDN and between 6.0 and 10.0 µg/ml for calprotectin. In a further alternative embodiment, the concentration in the post-treatment sample is, or is equivalent to, a value equal to or greater than 100 ng/ml for EDN and 7.5 µg/ml for calprotectin when the collected sample is lysed in 3 ml of lysis buffer.

In one embodiment, the concentration of EDN and/or calprotectin is measured at at least one of the following time points: 0 (pre-treatment), 10, 20, 30, 40, 50, 60, 90, 120, 240, 360 days post-treatment or a combination thereof. In one embodiment the concentration of EDN and/or calprotectin is measured at day 0 (pre-treatment) and any one or more of the following time points: 10, 20, 30, 40, 50, 60, 90, 120, 240, 360 days post-treatment.

In a further aspect of the invention there is provided a method for monitoring for disease relapse in an IBD patient in remission, the method comprising determining the concentration of at least one IBD-specific biomarker, or a fragment or variant thereof, in a sample of the colonic mucocellular layer obtained from a subject in remission, preferably at predetermined intervals, wherein the sample is obtained from the surface of the anal area following defaecation, comparing said concentration to a threshold value and determining a disease relapse when the concentration of the of at least one IBD-specific biomarker is said sample is equal to or greater than the threshold value.

In one embodiment the IBD-specific biomarker is EDN the threshold value is, or is equivalent to, between 35-120 ng/ml, when the collected sample is lysed in 3 ml of lysis buffer. In a further embodiment, the threshold value is, or is equivalent to, 100 ng/ml when the collected sample is lysed in 3 ml of lysis buffer.

In an alternative embodiment, the IBD-specific biomarker is calprotectin and the threshold value is, or is equivalent to, between 6.0 and 10.0 µg/ml when the collected sample is lysed in 3 ml of lysis buffer. In a further embodiment, the threshold value is, or is equivalent to, 7.5 µg/ml when the collected sample is lysed in 3 ml of lysis buffer.

In a further aspect of the invention there is provided a method for monitoring for disease relapse in an IBD patient in remission, the method comprising determining the concentration of the EDN protein, or a fragment or variant thereof, in a sample of the colonic mucocellular layer obtained from a subject at, preferably, predetermined intervals, and determining a disease relapse when the concentration of EDN is, or is equivalent to, a value equal to or greater than a value between 35-120 ng/ml when the collected sample is lysed in 3 ml of lysis buffer. In a preferred embodiment, the concentration of the EDN protein, or a fragment or variant thereof is measured at at least two time points and the method comprises determining a disease relapse when the concentration of EDN at at least one time point is, or is equivalent to, a value equal to or greater than a value between 35-120 ng/ml when the collected sample is lysed in 3 ml of lysis buffer. In a further alternative embodiment, the concentration of EDN is, or is equivalent to, a value equal to or greater than 100 ng/ml when the collected sample is lysed in 3 ml of lysis buffer.

In another aspect of the invention there is provided a method for monitoring for disease relapse in an IBD patient in remission, the method comprising determining the concentration of the calprotectin protein, or a fragment or variant thereof, in a sample of the colonic mucocellular layer obtained from a subject at predetermined intervals, and determining a disease relapse when the concentration of calprotectin is, or is equivalent to, a value equal to or greater than a value between 6.0 and 10.0 µg/ml when the collected sample is lysed in 3 ml of lysis buffer. In a preferred embodiment, the concentration of the calprotectin protein, or a fragment or variant thereof, is measured at at least two time points and the method comprises determining a disease relapse when the concentration of calprotectin is, or is equivalent to, a value equal to or greater than a value between 6.0 and 10.0 µg/ml when the collected sample is lysed in 3 ml of lysis buffer. In a further embodiment, the concentration of calprotectin is, or is equivalent to, a value equal to or greater than 7.5 µg/ml when the collected sample is lysed in 3 ml of lysis buffer.

In a further aspect of the invention there is provided a method of selecting a treatment for an IBD patient, the method comprising determining the concentration of at least one IBD-specific biomarker, or a fragment or variant thereof, in a sample of the colonic mucocellular layer obtained from a subject, wherein the sample is obtained from the surface of the anal area following defaecation, comparing said concentration to a threshold value and selecting a IBD-targeted therapy when the concentration of the at least one IBD-specific biomarker is said sample is equal to or greater than the threshold value.

In one embodiment the IBD-specific biomarker is EDN the threshold value is or is equivalent to, 35 ng/ml when the collected sample is lysed in 3 ml of lysis buffer. In an alternative embodiment, the IBD-specific biomarker is calprotectin and the threshold value is or is equivalent to, 6.0 µg/ml when the collected sample is lysed in 3 ml of lysis buffer.

In a further aspect of the invention there is provided a method of selecting a treatment for an IBD patient, the method comprising determining the concentration of the EDN protein, or a fragment or variant thereof, in a sample of the colonic mucocellular layer obtained from a subject, and selecting a IBD-targeted therapy when the concentration of EDN is, or is equivalent to, a value, equal to or greater than a value between between 35-120 ng/ml when the collected sample is lysed in 3 ml of lysis buffer. In a further embodiment, the concentration of EDN is, or is equivalent to, a value equal to or more than 100 ng/ml when the collected sample is lysed in 3 ml of lysis buffer.

In another aspect of the invention there is provided a method of selecting a treatment for an IBD patient, the method comprising determining the concentration of the calprotectin protein, or a fragment or variant thereof, in a sample of the colonic mucocellular layer obtained from a subject, and selecting a IBD-targeted therapy when the concentration of calprotectin is, or is equivalent to, a value, equal to or greater than a value between 6.0 and 10.0 µg/ml when the collected sample is lysed in 3 ml of lysis buffer. In a further embodiment, the concentration of calprotectin is, or is equivalent to, a value equal to or greater than 7.5 µg/ml when the collected sample is lysed in 3 ml of lysis buffer.

In a further aspect of the invention there is provided a method of selecting a subject for IBD-targeted therapy, the method comprising determining the concentration of at least one IBD-specific biomarker, or a fragment or variant thereof, in a sample of the colonic mucocellular layer obtained from a subject, wherein the sample is obtained from the surface of the anal area following defaecation, comparing said concentration to a threshold value and selecting the subject for IBD-targeted therapy when the concentration of the at least one IBD-specific biomarker is said sample is equal to or greater than the threshold value.

In one embodiment the IBD-specific biomarker is EDN the threshold value is, or is equivalent to, 35 ng/ml when the collected sample is lysed in 3 ml of lysis buffer. In an alternative embodiment, the IBD-specific biomarker is calprotectin and the threshold value is, or is equivalent to, 6.0 µg/ml when the collected sample is lysed in 3 ml of lysis buffer.

In a further aspect of the invention there is provided a method of selecting a subject for IBD-targeted therapy, the method comprising determining the concentration of the EDN protein, or a fragment or variant thereof, in a sample of the colonic mucocellular layer obtained from the subject, and selecting the subject for IBD-targeted therapy when the concentration of EDN is, or is equivalent to, a value, equal to or greater than a value between 35-120 ng/ml when the collected sample is lysed in 3 ml of lysis buffer. In a further embodiment, the concentration of EDN is, or is equivalent to, a value equal to or more than 100 ng/ml when the collected sample is lysed in 3 ml of lysis buffer.

In another aspect of the invention there is provided a method of selecting a subject for IBD-targeted therapy, the method comprising determining the concentration of the calprotectin protein, or a fragment or variant thereof, in a sample of the colonic mucocellular layer obtained from the subject, and selecting the subject for IBD-targeted therapy when the concentration of calprotectin is, or is equivalent to, a value, equal to or greater than a value between 6.0 and 10.0 µg/ml when the collected sample is lysed in 3 ml of lysis buffer. In a further embodiment, the concentration of calprotectin is, or is equivalent to, a value equal to or more than 7.5 µg/ml when the collected sample is lysed in 3 ml of lysis buffer.

In one embodiment of the methods described herein, the IBD is Crohn's disease. In an alternative embodiment of the methods described herein the IBD is Ulcerative colitis.

In one embodiment of the methods described herein, the methods further comprise determining the concentration of at least one further biomarker for IBD in said sample. In a preferred embodiment, the at least one further biomarker is selected from the group consisting of S100A12, ICAM1, CK-18, D-dimer, TNF-α, ASCA, pANCA, anti-GP2 antibodies, lactoferrin and total amount of human DNA in the sample or a combination thereof. The IBD-specific biomarker may also be a cytokine, alone or in combination with another IBD-specific biomarker.

In another embodiment of the methods described herein, the method further comprises analysing the cytology of said sample.

In one embodiment of the methods described herein, the subject has or is at risk of developing IBD. In an alternative embodiment the subject has no clinical signs or manifestations of IBD (i.e. the subject is asymptomatic). In a preferred embodiment, the subject is human.

In a further embodiment of the methods described herein, the concentration of the IBD-specific biomarker is determined by contacting the sample with at least one antibody capable of specifically binding the IBD-specific biomarker protein, or a fragment or variant thereof. In an alternative embodiment, the concentration of the IBD-specific biomarker is determined by detecting the expression levels of the IBD-specific biomarker, or a fragment or variant thereof. In a further embodiment total amount of human DNA in the sample is determined. The methods may further comprise comparing the concentration of the IBD-specific biomarker in a subject's sample with the concentration levels in a control or reference sample.

In a further aspect of the invention there is provided a method for diagnosing an IBD, the method comprising determining the concentration of both EDN and calprotectin, or a fragment or variant thereof of either protein, in a sample of colonic mucocellular layer obtained from a subject; comparing the concentration of both proteins to a threshold value to obtain a ratio of calprotectin concentration/calprotectin threshold and EDN concentration/EDN threshold; and determining that the subject has IBD when either or both ratio is above 1.0.

In a preferred embodiment, the threshold value for calprotectin is, or is equivalent to a value, of 4.7 µg/ml when the collected sample is lysed in 3 ml of lysis buffer. In a further embodiment, the threshold value for calprotectin is, or is equivalent to a value, of 3.5 µg/ml when the collected sample is lysed in 3 ml of lysis buffer. In an alternative embodiment, the threshold value for calprotectin is, or is equivalent to a value, 6.0 µg/ml when the collected sample is lysed in 3 ml of lysis buffer.

In an alternative embodiment, the threshold value for EDN is, or is equivalent to a value, of 24 ng/ml when the collected sample is lysed in 3 ml of lysis buffer. In a further preferred embodiment, the threshold value for EDN is 15 ng/ml when the collected sample is lysed in 3 ml of lysis buffer. In an alternative embodiment, the threshold value for EDN is 35 ng/ml when the collected sample is lysed in 3 ml of lysis buffer.

In a preferred embodiment, the IBD is ulcerative colitis. In an alternative embodiment, the IBD is Crohn's disease.

In a further embodiment, the method further comprises determining the concentration of at least one further biomarker for IBD in said sample. In one embodiment the at least one further biomarker is selected from the group consisting of S100A12, ICAM1, CK-18, D-dimer, TNF-α, ASCA, pANCA, anti-GP2 antibodies, lactoferrin and total amount of human DNA in the sample or a combination thereof. The IBD-specific biomarker may also be a cytokine, alone or in combination with another IBD-specific biomarker.

In a further aspect of the invention there is provided a method of differentially diagnosing ulcerative colitis from Crohn's disease, the method comprising determining the concentration of both calprotectin and EDN, or a fragment or variant thereof of either protein, in a sample of colonic mucocellular layer obtained from a subject, comparing the concentration of both proteins to a threshold value to obtain a ratio of calprotectin concentration/calprotectin threshold and EDN concentration/EDN threshold; and determining that the subject has ulcerative colitis when either or both ratio is above 4.0. In a further embodiment, the method further comprises determining the concentration of at least one other IBD-specific biomarker. Preferably, the at least one other IBD-specific biomarker is ASCA and/or GP-2 antibodies.

In a preferred embodiment, the method further comprises determining the concentration of the ICAM1 protein, or a fragment or variant thereof in said sample. Preferably, the method further comprises multiplying the ratio by a weighting factor when ICAM1 cannot be detected in said sample. Preferably, the weighting factor is less than zero. More preferably, the weighting factor is 0.1. In a preferred embodiment, the subject is determined to have ulcerative colitis (rather than Crohn's disease) when either or both ratio is equal to or greater than 4.0. In a further preferred embodiment, the subject is determined to have ulcerative colitis when either or both ratio is equal to or greater than 9.0.

In a further preferred embodiment, the method further comprises determining the concentration of at least one further IBD-specific biomarker in said sample. In one embodiment, the at least one further IBD-specific biomarker is selected from the group consisting of ASCA (Anti-*Saccharomyces cerevisiae* antibodies), GP-2 and perinuclear cytoplasmic antibodies (pANCA).

In a further aspect of the invention there is provided a method for diagnosing ulcerative colitis, the method comprising determining the concentration of the S100A12 protein, or a fragment or variant thereof, in a sample of colonic mucocellular layer obtained from a subject, and determining that the subject has ulcerative colitis when the concentration of S100A12 is, or is equivalent to a value, equal or more than 50 ng/ml when the collected sample is lysed in 3 ml of lysis buffer.

In another aspect of the invention there is provided a method for diagnosing an inflammatory bowel disease (IBD), the method comprising determining the concentration of the ICAM1 protein, or a fragment or variant thereof, in a sample of the colonic mucocellular layer obtained from a subject, comparing said concentration to a threshold value and determining that the subject has an IBD when the concentration of ICAM1 is equal to or greater than the threshold value. In one embodiment the threshold value is or is equivalent to 150 μg/ml when the collected sample is lysed in 3 ml of lysis buffer.

In a further aspect of the invention there is provided a method of differentially diagnosing ulcerative colitis from Crohn's disease, the method comprising determining the concentration of ICAM1, or a fragment or variant thereof in a sample of colonic mucocellular layer obtained from a subject, comparing the concentration to a threshold value and determining that the subject has ulcerative colitis when the concentration of ICAM1 is equal to or greater than the threshold vale. In one embodiment the threshold value is or is equivalent to 150 μg/ml when the collected sample is lysed in 3 ml of lysis buffer.

In another aspect of the invention there is provided a method of selecting a treatment for an IBD patient, the method comprising determining the concentration of the ICAM1 protein, or a fragment or variant thereof, in a sample of the colonic mucocellular layer obtained from a subject, and selecting a ICAM1-targeted therapy when the concentration of ICAM1 is above a threshold value. In one embodiment the threshold value is or is equivalent to 150 μg/ml when the collected sample is lysed in 3 ml of lysis buffer. In one embodiment the ICAM1-targeted therapy is alicaforsen.

In a further aspect of the invention there is provided a method for assessing colonic mucosa damage, the method comprising determining the concentration of at least one epithelial-damage specific biomarker, or a fragment or variant thereof, in a sample of the colonic mucocellular layer obtained from a subject, comparing said concentration to a threshold value, and determining that the colonic mucosa is damaged when the concentration of the at least one epithelial-damage specific biomarker is equal to or greater than the threshold value. In one embodiment, the epithelial damage-specific biomarker is CK-18 and the threshold value is, or is equivalent to 300 U/L when the collected sample is lysed in 3 ml of lysis buffer. In a further embodiment, the epithelial damage-specific biomarker is CK-18 and the threshold value is, or is equivalent to 500 U/L when the collected sample is lysed in 3 ml of lysis buffer. In another embodiment, the epithelial damage-specific biomarker is CK-18 and the threshold value is, or is equivalent to, a value within the range 100 U/L to 35 U/L when the collected sample is lysed in 3 ml of lysis buffer.

In an alternative embodiment of the methods described above the threshold value is determined by measuring the concentration of an IBD-specific biomarker in a group of one or more control subjects. Preferably, a group of five or more control subjects. More preferably, a group of ten or more control subjects.

In a further alternative embodiment, the threshold value defines a fractile of a distribution of measured concentrations for a population of control subjects without IBD. Preferably, said fractile is a 0.9 or greater fractile. Preferably, said distribution is assumed to be a Gaussian distribution.

In an alternative embodiment, the threshold value identifies that said subject is IBD-positive with greater than a threshold value. In a further alternative embodiment, said threshold value is associated with a defined probability of determining that said subject has IBD, when said subject has IBD. Preferably, said defined probability is greater than 60%, preferably 65%, preferably 70%, preferably 75%, preferably 80%, preferably 85%, preferably 90%, preferably 95%, preferably 100%.

In one embodiment of any of the methods described above the sample of colonic mucocellular layer from said subject is obtained from the surface of the anal area following defaecation. Preferably, the sample is obtained from the surface of the anal area in the vicinity of the exterior opening of the anal canal. The sample may be obtained by taking a swab of said area. Preferably the sample is taken prior to cleaning the area. In a further embodiment, the sample is taken within 5 minutes of defaeccation. More preferably, the sample is taken within 4, 3, 2 or 1 minute of defaecation.

In embodiments of the invention, when the concentration of a biomarker, in particular EDN and/or calprotectin is determined, it may be determined in any volume of lysis, in which case the measured concentration may be expressed as if the lysis had been in 3 ml of solution, i.e. normalised to the above-mentioned 3 ml of lysis buffer.

For reasons of clinical repeatability of the test it can also be advantageous to define the threshold with reference to a standardised swab size/type and/or swab procedure—but this is not essential to the above-mentioned threshold values used, for example, for distinguishing between patient groups. This is because although it may be useful to have clinical tests conducted under standardised conditions, in practice the variation introduced by say, using one swab as compared with multiple swabs of the same region, or by using a larger or a smaller swab on a region, may be relatively small. Nonetheless such a standardised swab procedure may comprise, for example, a single swab of the target area and/or a defined swab size and/or shape. For example the swab shape may be defined as a circle or oval, optionally with a minimum dimension of not less than 5 mm and/or with a maximum dimension of not more than 10 mm, 15 mm or 20 mm. Additionally or alternatively the swab size may be defined as having a surface area of at least 40 mm$^2$, 160 mm$^2$, 350 mm$^2$ or 600 mm$^2$.

In a further aspect of the invention, we provide a non-invasive method for collecting a sample of intestinal or bowel cells or cell fragments comprising taking a swab of mucocellular layer material originating from said bowel or intestine from the surface of the anal area in the vicinity of the exterior opening of the anal canal, wherein said swab is taken following defaecation. Preferably the swab is taken prior to cleaning the area. In a further embodiment, we describe a method of collecting a sample of intestinal or bowel cells or cell fragments using the above method and analysing said sample for the presence of one or more IBD-specific markers. Accordingly, we also provide a method for diagnosing and screening for bowel disease using the above method. The bowel disease may be a IBD, colorectal cancer, anal cancer or advanced colorectal polyps.

In a final aspect of the invention there is provided a kit. In a preferred embodiment the kit is suitable for implementing any of the above described methods. In one embodiment the kit comprises at least one antibody, wherein each of said antibody is capable of binding to at least one IBD-specific biomarker or a fragment or variant thereof. Preferably, the antibody is capable of binding to EDN and/or calprotectin or a fragment or variant thereof. In another alternative embodiment, the kit comprises at least one antibody capable of binding S100A12, or a fragment or variant thereof. In a further alternative embodiment the kit comprises at least one antibody capable of binding ICAM1, or a fragment or variant thereof.

In a preferred embodiment the kit comprises agents for the detection of the at least one antibody binding to said biomarker. In a further embodiment the kit comprises instructions for use. In a further embodiment the kit comprises a positive control sample.

In a further preferred embodiment, the kit comprises at least one swab. Preferably the kit comprises two swabs. In a further preferred embodiment, the kit further comprises a sample tube. Preferably, the sample tube comprises a material-lysing lysis buffer. The sample tube may further comprise a material-preserving buffer. The kit may further comprise a fixative for cytological samples. The kit may further comprise a sampling card containing at least one, preferably two, microscope slides. In a further embodiment the kit further comprises a lateral flow assay. In an alternative embodiment the kit comprises an electrochemical biosensor or biosensors.

In all above embodiments where a range is stated, the value may be either end-point of the range, or a value within the stated range. For example, where the threshold value is between 15 ng/ml and 35 ng/ml, this value is of 15 ng/ml and 35 ng/ml.

A—The rectum is empty between two normal acts of defaecation. Gradual accumulation of the colonic mucocellular layer is progressing. 20—rectum; 21—anus; 22—colonic mucocellular layer overlaying the rectal mucosa.

B—Stool (23) portions start entering the rectum. At this moment there is no significant contact between stool and the colonic mucocellular layer.

C—The rectum is filled with stool, which comes into a close contact with the colonic mucocellular layer. Muscular contraction of the rectum preceding defaecation enhances this contact.

D—Defaecation. Stool is being evacuated from the rectum by concerted rectal contractions and anal canal opening. A considerable proportion of the colonic mucocellular layer is evacuated together with stool, being predominantly on its surface or on the walls of the anal canal (as an additional lubricant). Fragments of the colonic mucocellular layer (24) remain on the surface of the external anal/perianal area often mixed with stool fragments.

E—Immediately post-defaecation. The colonic mucocellular layer is considerably depleted immediately following defaecation. Its excreted fragments remain on the surface of the external anal/perianal area (and are removed by cleaning unless sample collection is planned).

Figure 2:
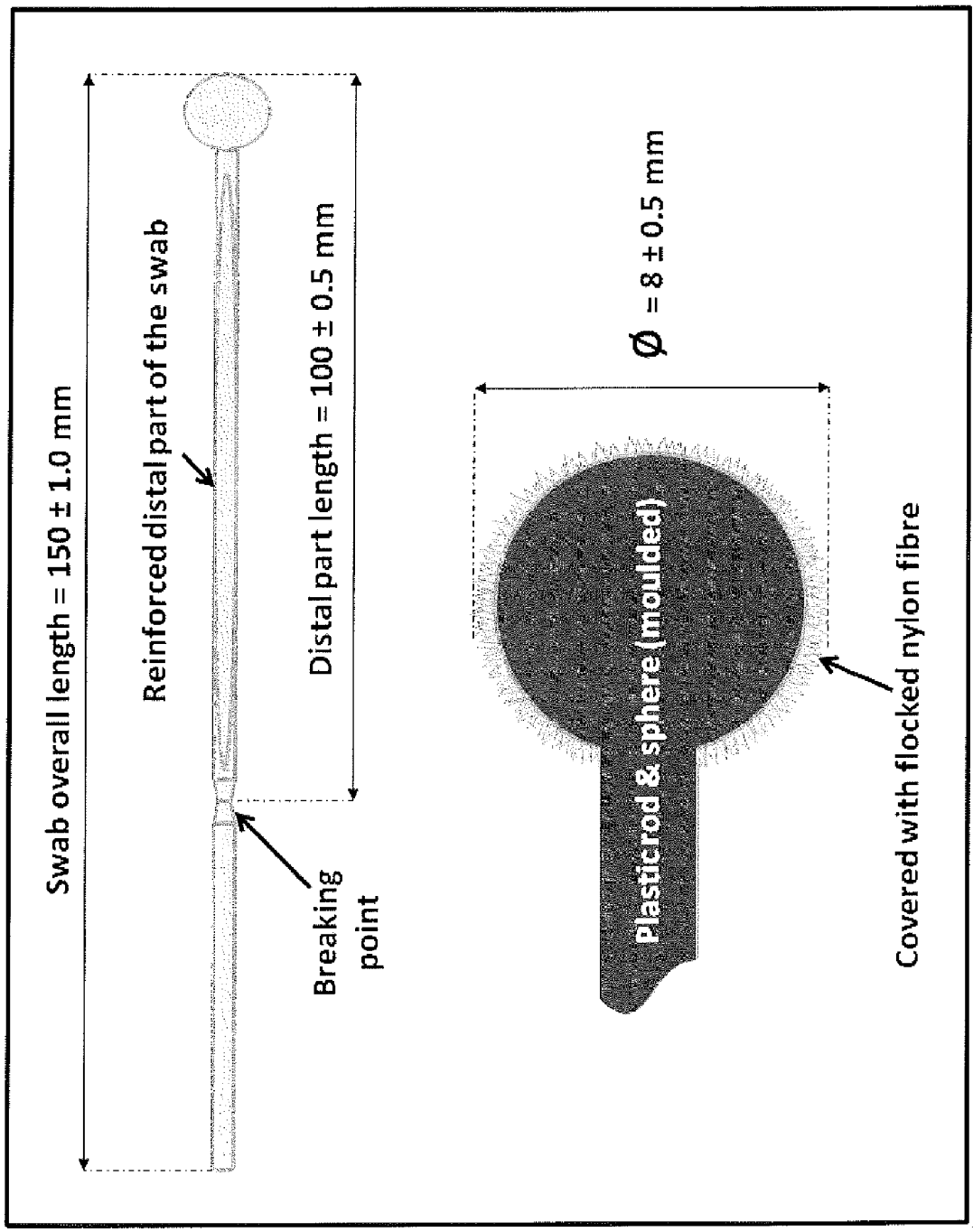

F—Post-defaecation collection of the excreted fragments of the colonic mucocellular layer using the swab described in this invention (see FIG. 2).

FIG. 2: Features of the swab used for collecting colonic mucocellular layer samples from the anal area of a human subject suspected of being affected with inflammatory bowel disease immediately following bowel opening.

Figure 3A:

FIG. 3a: Photomicrograph of a sample of colonic mucocellular layer obtained using the swab shown in FIG. 2 from a healthy volunteer. The sample was placed on a microscope slide and stained with haematoxylin and eosin. The main feature of samples obtained from healthy people was scarcity of cellular material. Exfoliated normal colonocytes (two colonocytes are marked by arrows) constituted the predominant cell type in such samples.

Figure 3B:
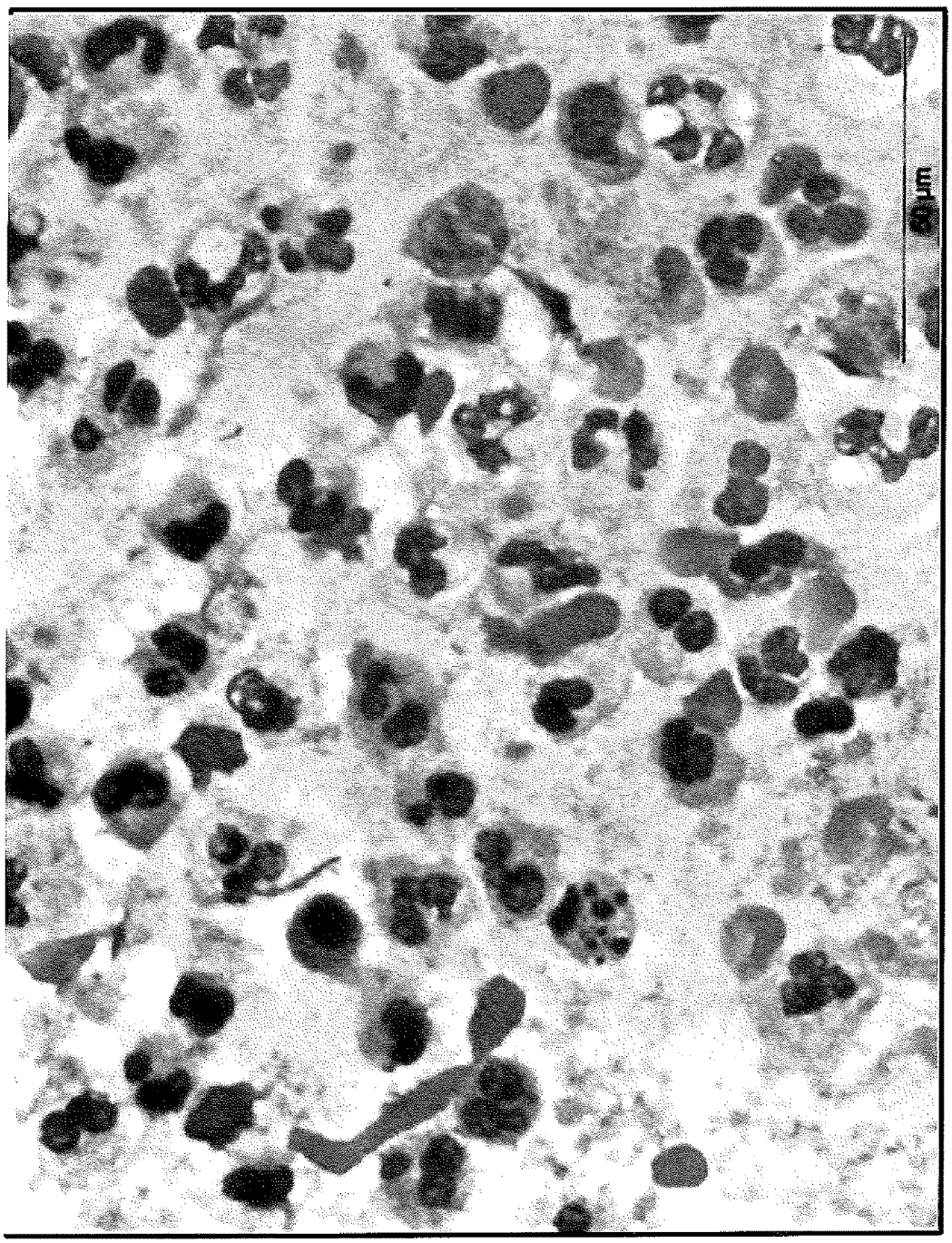

FIG. 3b: Photomicrograph of a sample of colonic mucocellular layer obtained using the swab shown in FIG. 2 from a patient with ulcerative colitis (UC). The sample was placed on a microscope slide and stained with haematoxylin and eosin. Samples obtained from UC patients were characterised by abundant presence of very well preserved free inflammatory cells, especially polymorhonuclear leukocytes comprising neutrophils (multiple cells with segmented nuclei that can be seen) and eosinophils. Erythrocyte presence (several erythrocytes are present) was also common reflecting frequent bleeding.

Figure 3C:
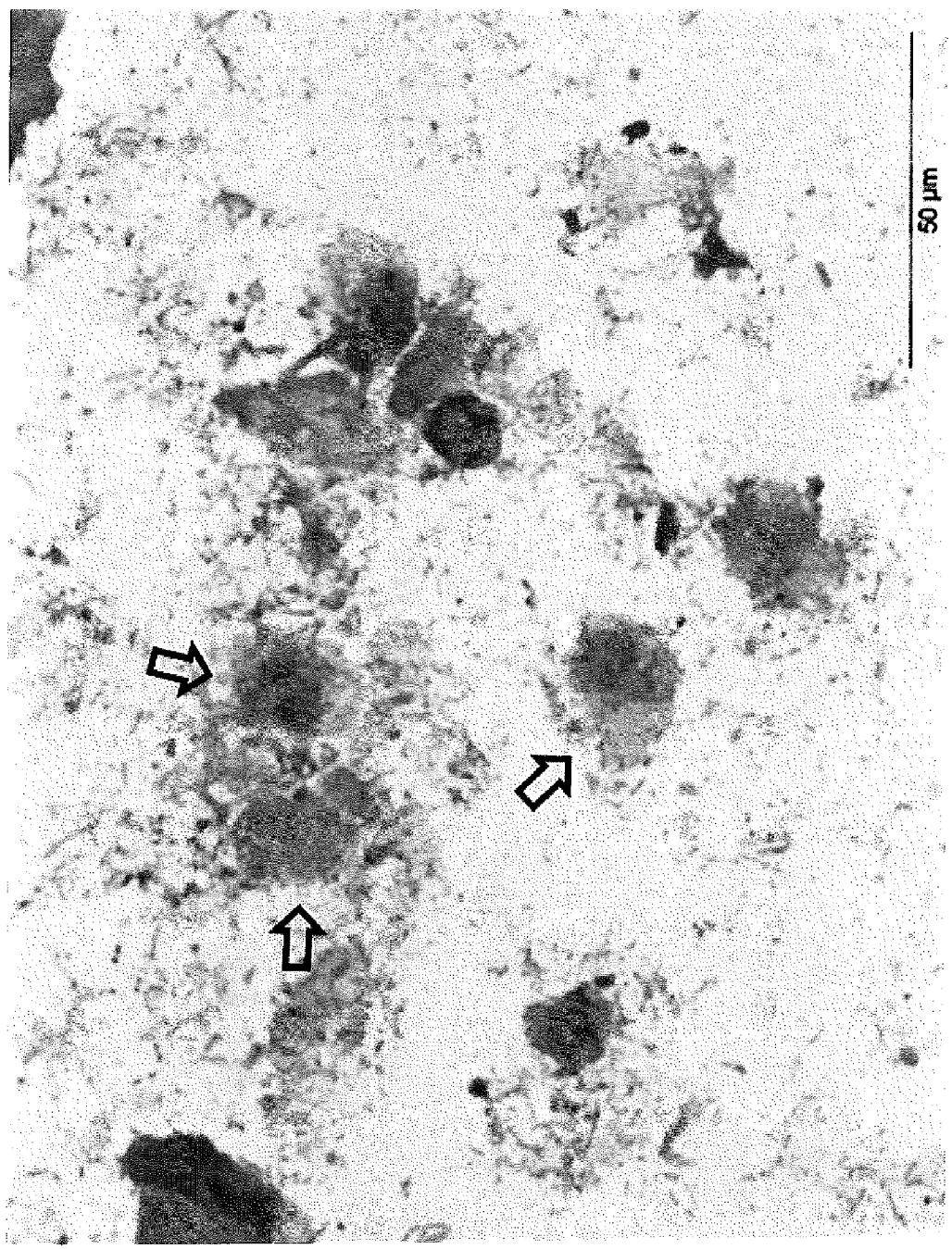

FIG. 3c: Photomicrograph of a sample of colonic mucocellular layer obtained using the swab shown in FIG. 2 from a patient with Crohn's disease (CD) predominantly affecting ileum (proximal CD). The sample was placed on a microscope slide and stained with haematoxylin and eosin. Proximal CD cases were often characterised by the presence of distinguishable, but damaged polymorphonuclear leukocytes ("leukocyte shadows") marked by arrows.

Figure 4A:
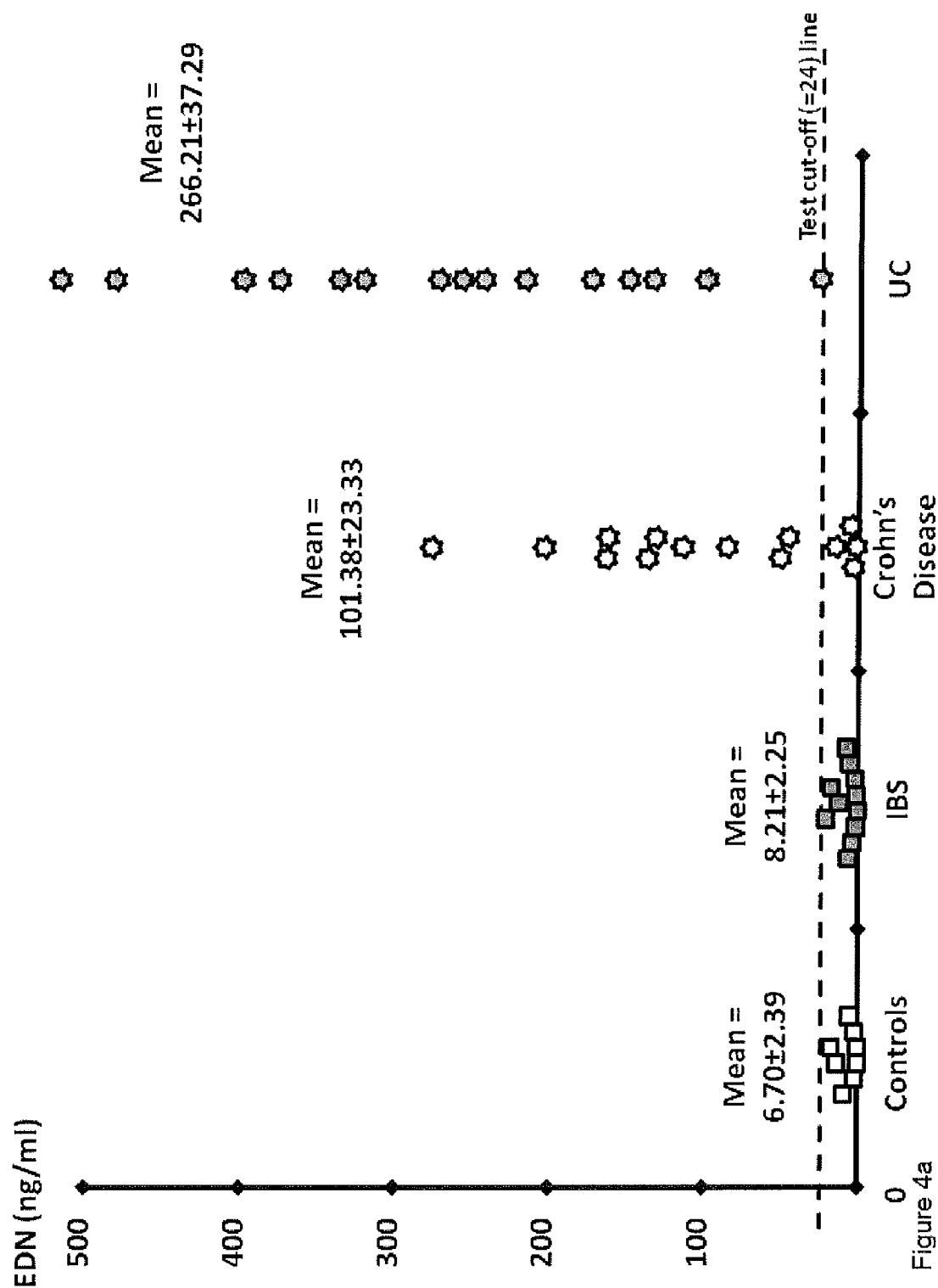

FIG. 4a: EDN concentrations (ng/ml) measured in lysates of colonic mucocellular layer samples obtained from eight healthy volunteers (white squares), 11 patients with IBS (grey squares), 14 patients with Crohn's disease (CD—white stars) and 15 IBD patients with UC (grey stars). All measured samples from patients with CD and UC were obtained before treatment initiation. Results in the control and IBS groups were uniformly low (all EDN concentration values were below 24 ng/ml). Among IBD patients EDN concentrations were higher in the UC subgroup, where all results were above 24 ng/ml. In the CD subgroup four results were below this threshold (all three cases of ileal CD were among them). Result distributions did not deviate from normal distribution allowing application of parametric statistics.

Figure 4B:
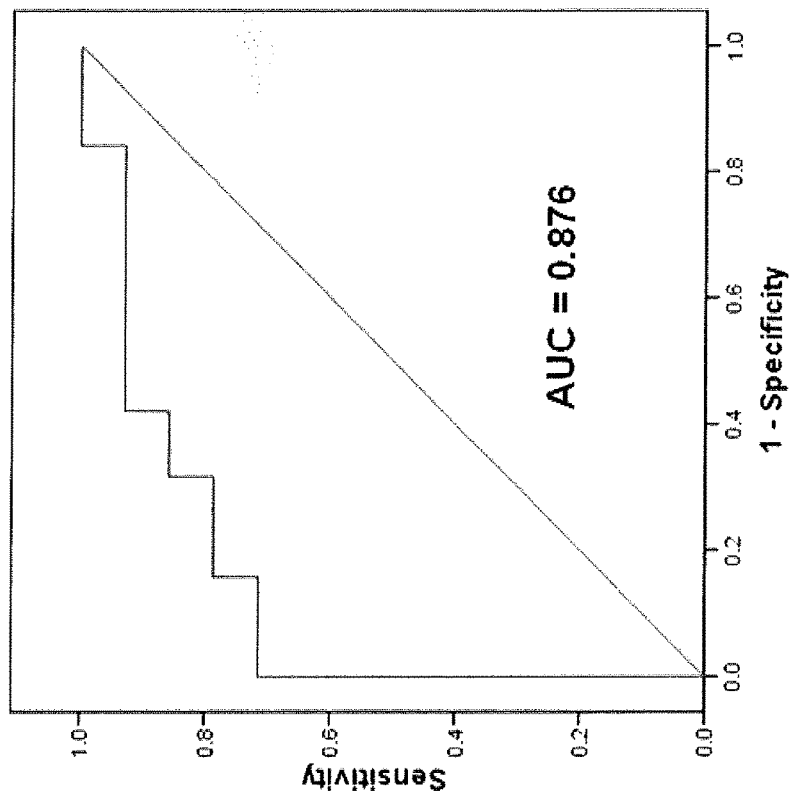

FIG. 4b: Receiver Operating Characteristic (ROC) curve illustrating EDN test sensitivity and specificity for detecting CD (14 patients with CD were compared with 19 individuals from control and IBS groups). Area under the curve is 0.876. At EDN concentration cut-off point=24 ng/ml (optimal cut-off): test sensitivity=71.4%; test specificity=100%. At EDN concentration cut-off point=15 ng/ml (lower limit cut-off): test sensitivity=78.6%; test specificity=84.2%. At EDN concentration cut-off point=35 ng/ml (upper limit cut-off): test sensitivity=71.4%; test specificity=100%.

Figure 4C:
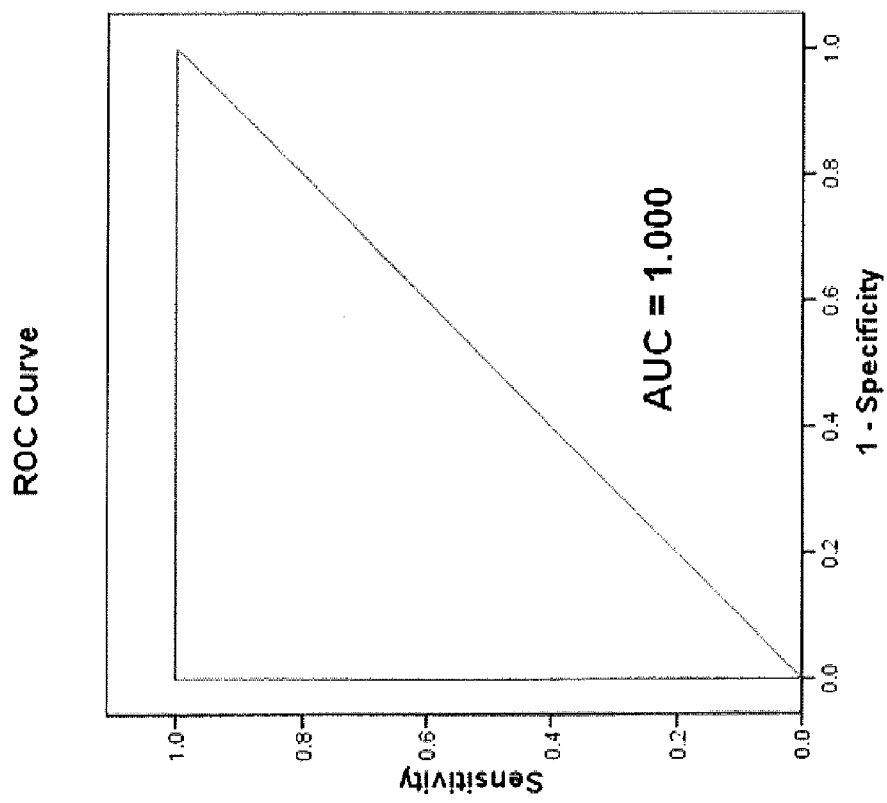

FIG. 4c: ROC curve illustrating EDN test sensitivity and specificity for detecting UC (15 patients with UC were compared with 19 individuals from control and IBS groups). Area under the curve is 1.000. At EDN concentration cut-off point=24 ng/ml (optimal cut-off): test sensitivity=100%; test specificity=100%. At EDN concentration cut-off point=15 ng/ml (lower limit cut-off): test sensitivity=100%; test specificity=84.2%. At EDN concentration cut-off point=35 ng/ml (upper limit cut-off): test sensitivity=93.3%; test specificity=100%.

FIG. 5a: EDN concentrations (ng/ml) measured in lysates of colonic mucocellular layer samples obtained from healthy volunteers and patients with IBS (pooled results from 19 individuals) and IBD patients (pooled results from 29 cases). Average EDN concentration value in the IBD group was 24.7-fold higher than in the control & IBS group.

Figure 5B:
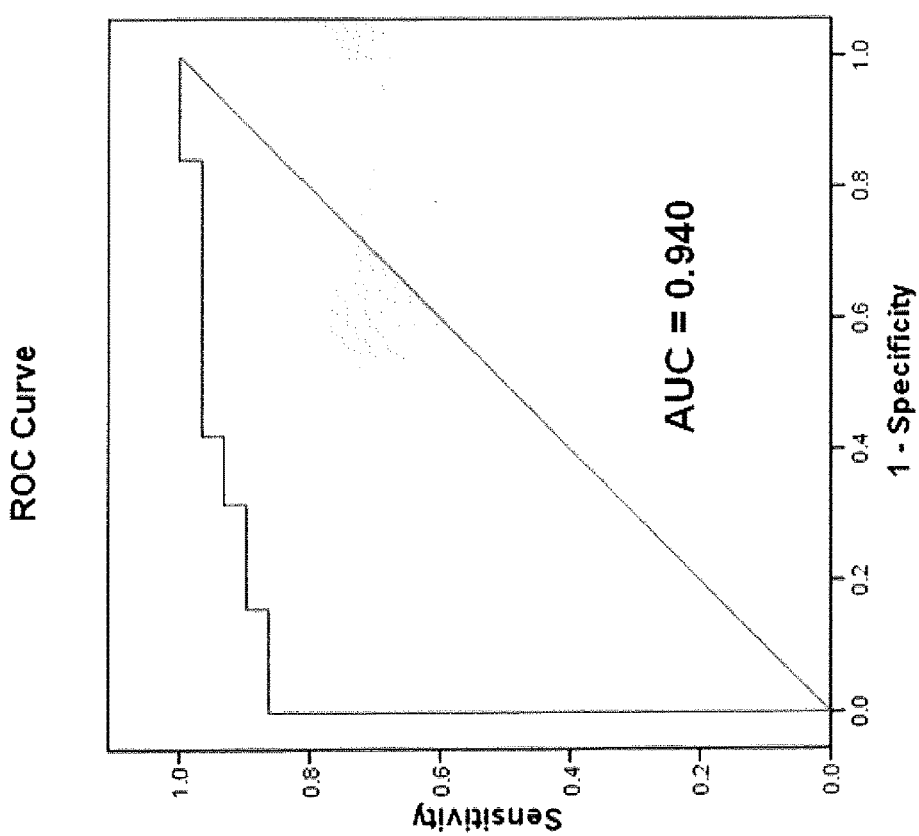

FIG. 5b: ROC curve illustrating EDN test sensitivity and specificity for detecting IBD (29 patients with IBD were compared with 19 individuals from control and IBS groups). Area under the curve is 0.940. At EDN concentration cut-off point=24 ng/ml (optimal cut-off): test sensitivity=86.2%; test specificity=100%. At EDN concentration cut-off point=15 ng/ml (lower limit cut-off): test sensitivity=89.7%; test specificity=84.2%. At EDN concentration cut-off point=35 ng/ml (upper limit cut-off): test sensitivity=82.8%; test specificity=100%.

Figure 6A:
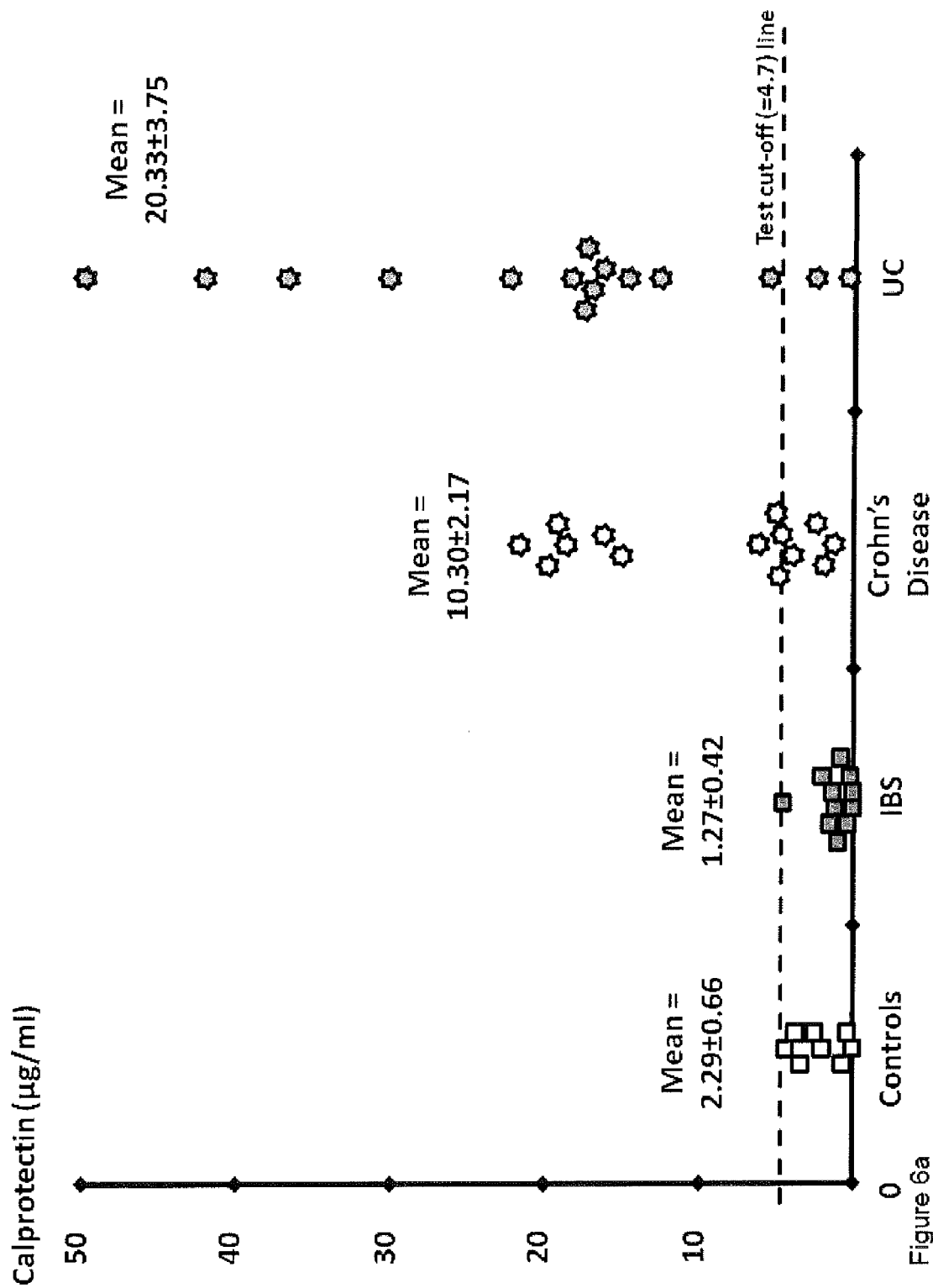

FIG. 6a: Calprotectin concentrations (µg/ml) measured in lysates of colonic mucocellular layer samples obtained from eight healthy volunteers (white squares), 11 patients with IBS (grey squares), 14 patients with Crohn's disease (CD—white stars) and 15 IBD patients with UC (grey stars). All measured samples from patients with CD and UC were obtained before treatment initiation. Results in the control and IBS groups were uniformly low (all calprotectin concentration values are below 4.7 µg/ml). Among IBD patients calprotectin concentrations were higher in the UC subgroup, where all results except two were above 4.7 µg/ml. In the CD subgroup four results were below this threshold (there were no ileal CD cases among them). Result distributions did not deviate from normal distribution allowing application of parametric statistics.

Figure 6B:
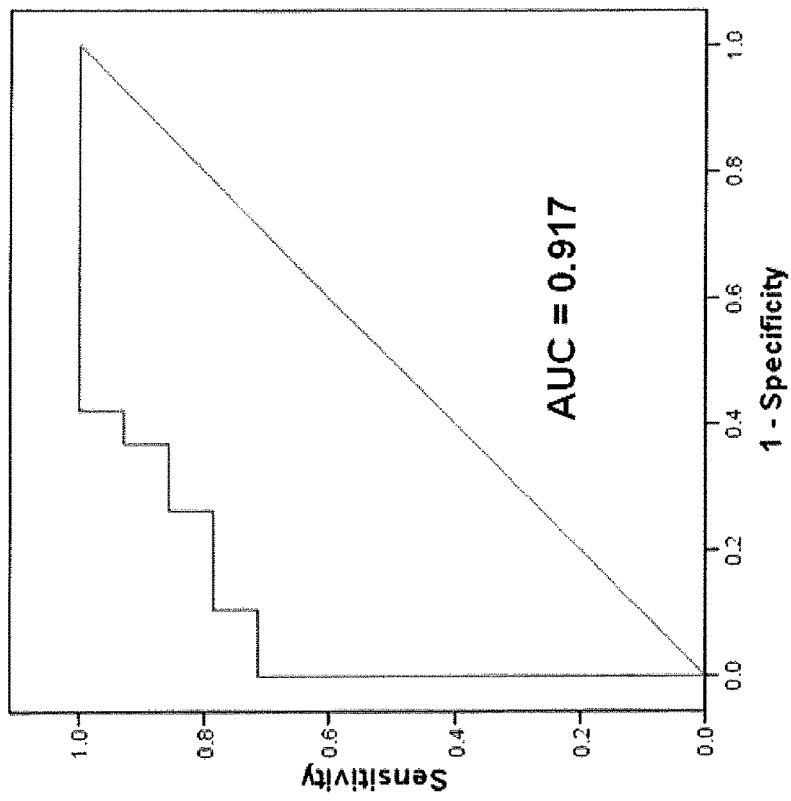

FIG. 6b: ROC curve illustrating calprotectin test sensitivity and specificity for detecting CD (14 patients with CD were compared with 19 individuals from control and IBS groups). Area under the curve is 0.917 (slightly higher than for EDN). At calprotectin concentration cut-off point=4.7 µg/ml (optimal cut-off): test sensitivity=71.4%; test specificity=100%. At calprotectin concentration cut-off point=3.5 µg/ml (lower limit cut-off): test sensitivity=78.6%; test specificity=78.9%. At calprotectin concentration cut-off point=6.0 µg/ml (upper limit cut-off): test sensitivity=50.0%; test specificity=100%.

Figure 6C:
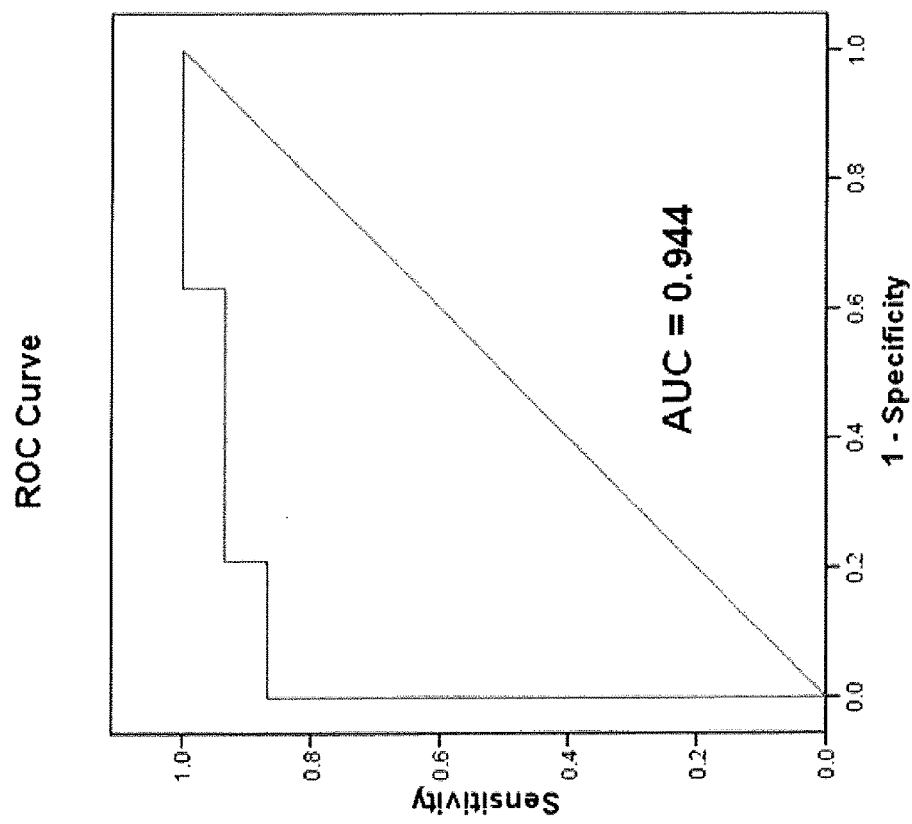

FIG. 6c: ROC curve illustrating calprotectin test sensitivity and specificity for detecting UC (15 patients with UC were compared with 19 individuals from control and IBS groups). Area under the curve is 0.944 (lower than for EDN). At calprotectin concentration cut-off point=4.7 µg/ml (optimal cut-off): test sensitivity=86.7%; test specificity=100%. At calprotectin concentration cut-off point=3.5 µg/ml: test sensitivity=86.7%; test specificity=78.9%. At calprotectin concentration cut-off point=6.0 µg/ml (upper limit cut-off): test sensitivity=80.0%; test specificity=100%.

Figure 7A:
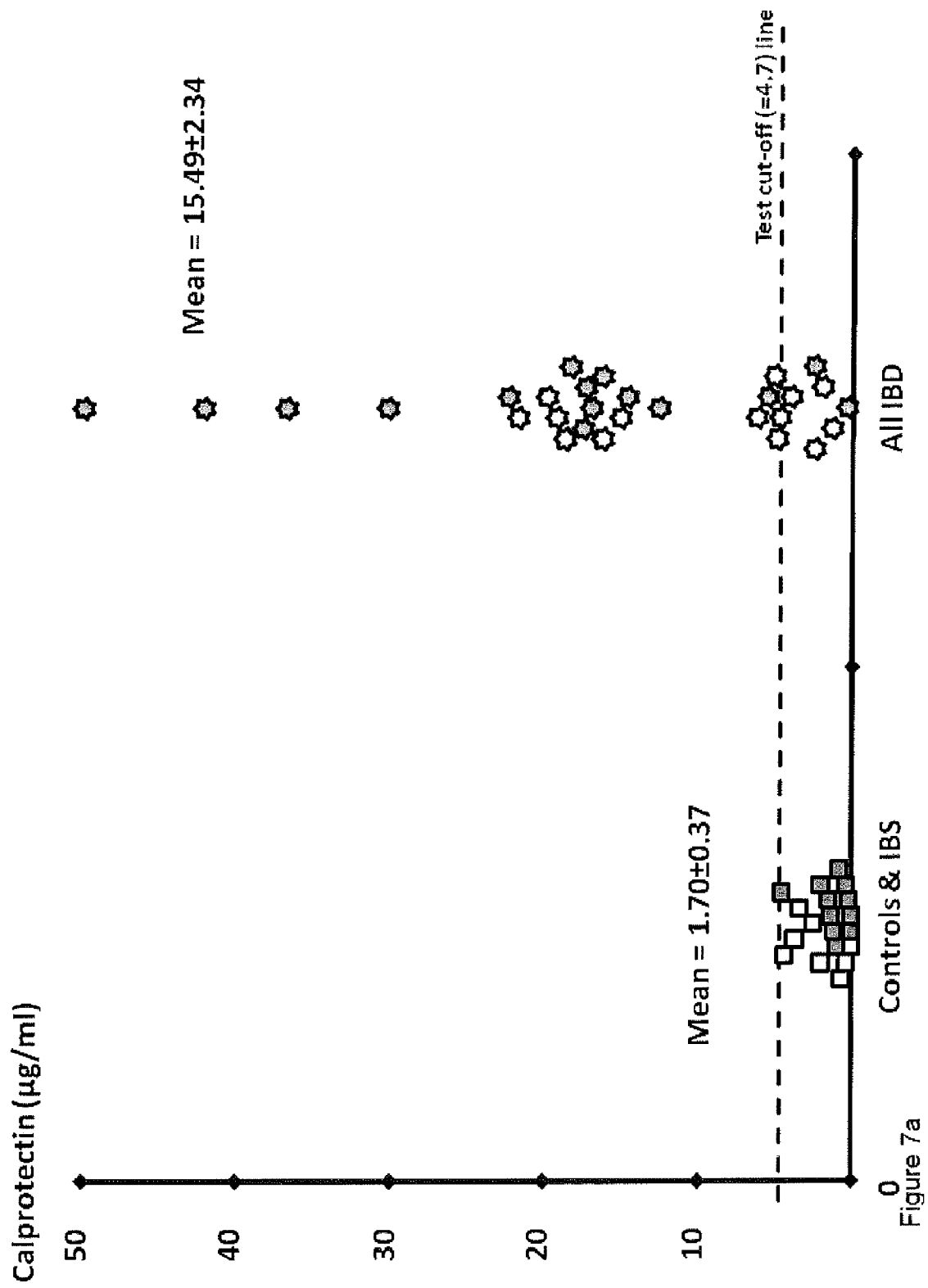

FIG. 7a: Calprotectin concentrations (µg/ml) measured in lysates of colonic mucocellular layer samples obtained from healthy volunteers and patients with IBS (pooled results from 19 individuals) and IBD patients (pooled results from 29 cases). Average calprotectin concentration value in the IBD group was 9.1-fold higher than in the control & IBS group.

Figure 7B:
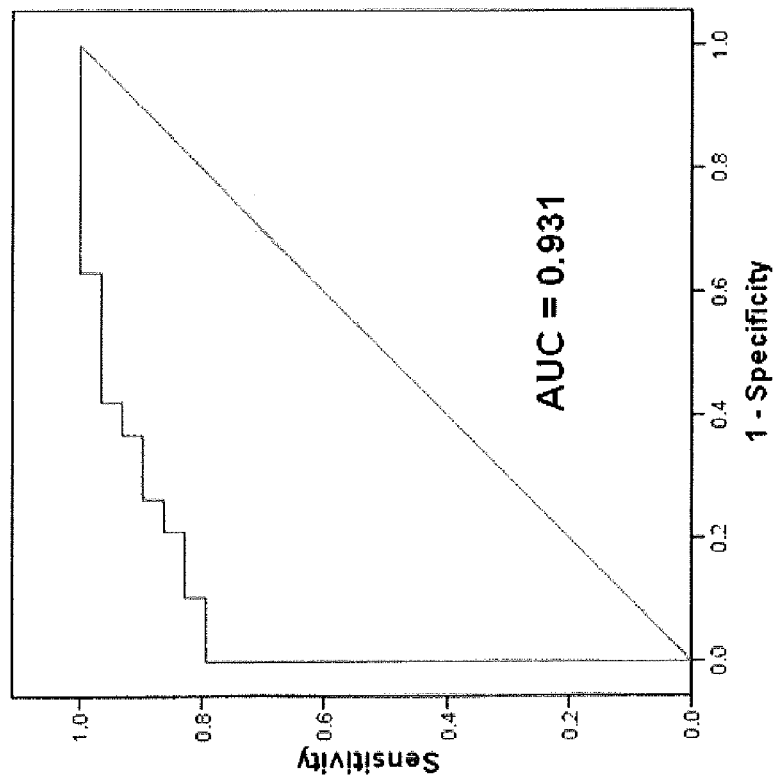

FIG. 7b: ROC curve illustrating calprotectin test sensitivity and specificity for detecting IBD (29 patients with IBD were compared with 19 individuals from control and IBS groups). Area under the curve is 0.931. At calprotectin concentration cut-off point=4.7 µg/ml (optimal cut-off): test sensitivity=79.3%; test specificity=100%. At calprotectin concentration cut-off point=3.5 µg/ml (lower limit cut-off): test sensitivity=82.8%; test specificity=78.9%. At calprotectin concentration cut-off point=6.0 µg/ml (upper limit cut-off): test sensitivity=65.5%; test specificity=100%. Overall performance of the calprotectin test for IBD detection appeared to be inferior in comparison with the EDN test.

Figure 8:
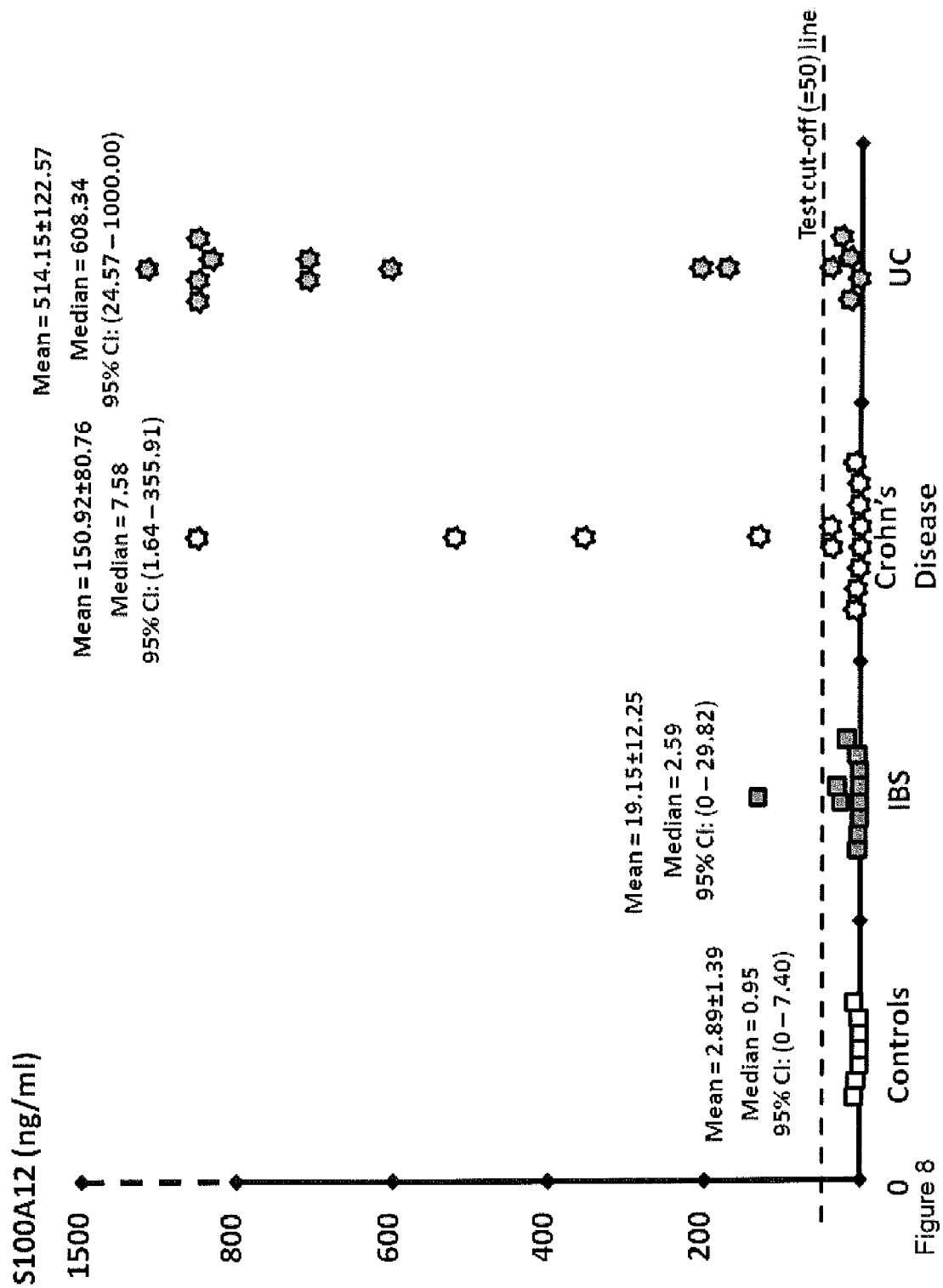

FIG. 8: S100A12 protein concentrations (ng/ml) measured in lysates of colonic mucocellular layer samples obtained from seven healthy volunteers (white squares), 11 patients with IBS (grey squares), 14 patients with Crohn's disease (CD—white stars) and 15 IBD patients with UC (grey stars). All measured samples from patients with CD and UC were obtained before treatment initiation. Results in the control and IBS groups were mostly low. A wide range of results was observed among IBD patients. In the CD group the majority of patients had low S100A12 concentrations, whereas elevated levels of this protein were detected in most cases of UC. Application of parametric statistics produced visibly exaggerated mean estimates in the IBS and CD groups, therefore median values and 95% confidence intervals are shown as well. Although S100A12 test could be considered for UC detection, its performance for detecting CD and IBD in general was clearly inferior compared to EDN and calprotectin tests.

Figure 9:
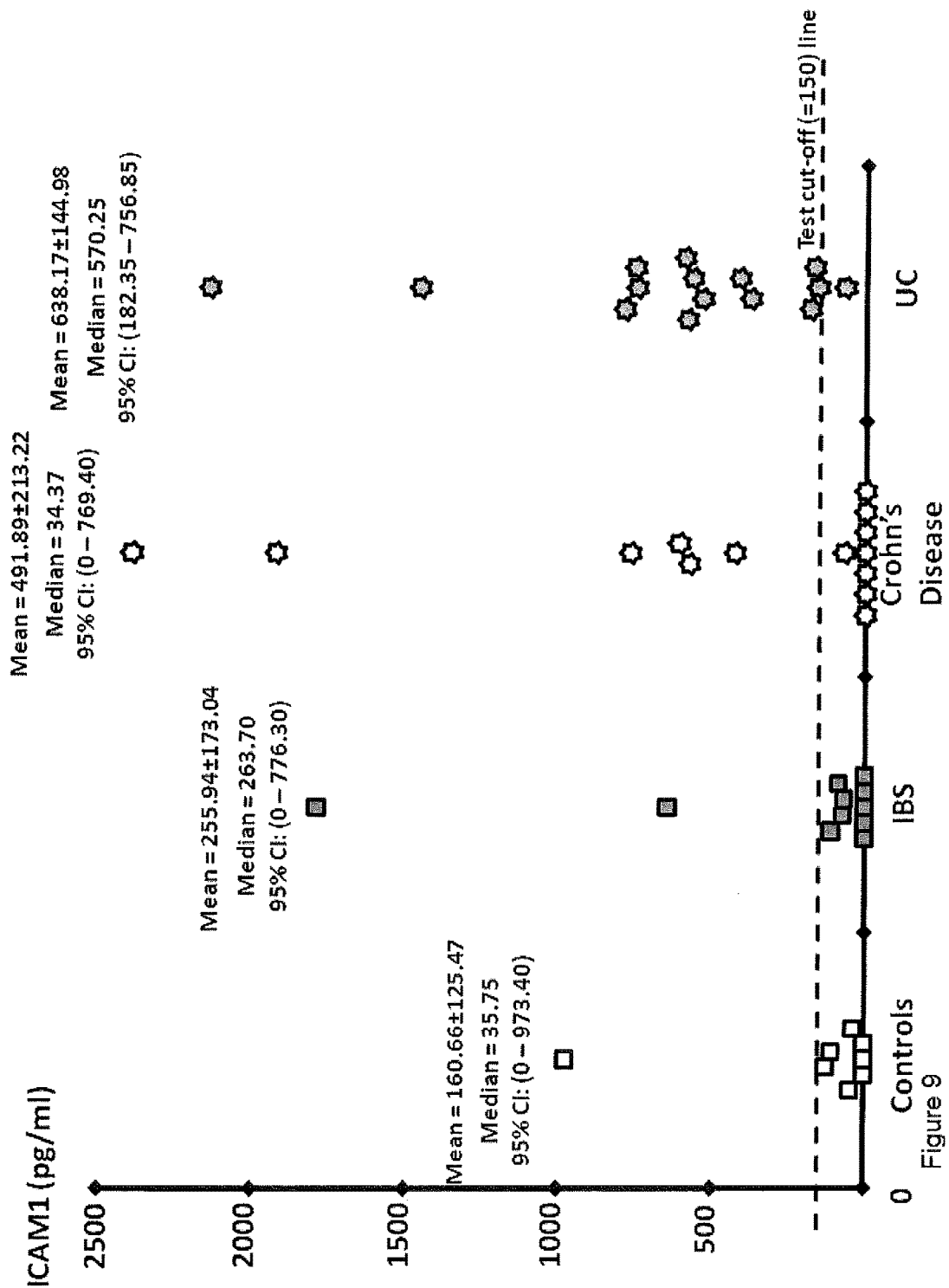

FIG. 9: ICAM1 protein concentrations (pg/ml) measured in lysates of colonic mucocellular layer samples obtained from eight healthy volunteers (white squares), 11 patients with IBS (grey squares), 14 patients with Crohn's disease (CD—white stars) and 15 IBD patients with UC (grey stars). All measured samples from patients with CD and UC were obtained before treatment initiation. Results in the control and IBS groups were mostly low, however high values were observed in one control and two IBS patients. Result distribution was clearly bimodal in the CD group with no ICAM1 presence detectable in seven cases. In contrast, ICAM1 was detected in all UC cases (only one result below 150 µg/ml). Application of parametric statistics produced clearly exaggerated mean estimates in all groups except UC, therefore median values and 95% confidence intervals are shown as well. The results showed that ICAM1 test was not a good candidate for IBD detection, but allowed to identify an important subset of patients with CD.

FIG. 10a: Results of combined secondary analysis (combined test) based upon the use of EDN and calprotectin measurement in lysates of colonic mucocellular layer samples obtained from healthy volunteers and patients with IBS (pooled results from 19 individuals) and IBD patients (pooled results from 29 cases). Two-step analysis was applied. The first step comprised determination of the following two ratios: a) detected EDN concentration/EDN test optimal cut-off point (24 ng/ml); b) detected calprotectin concentration/calprotectin test optimal cut-off point (4.7 µg/ml). At the second step the obtained two ratios for each individual were compared and the higher of each two values was used as the result for the individual. Ratios below or equal to 1.0 were interpreted as negative results, whereas ratios above 1.0 were interpreted as positive results. It is remarkable that negative results were obtained in all subjects from the control and IBS groups. In contrast, only one negative result (one CD case) was observed in the IBD group.

Figure 10B:
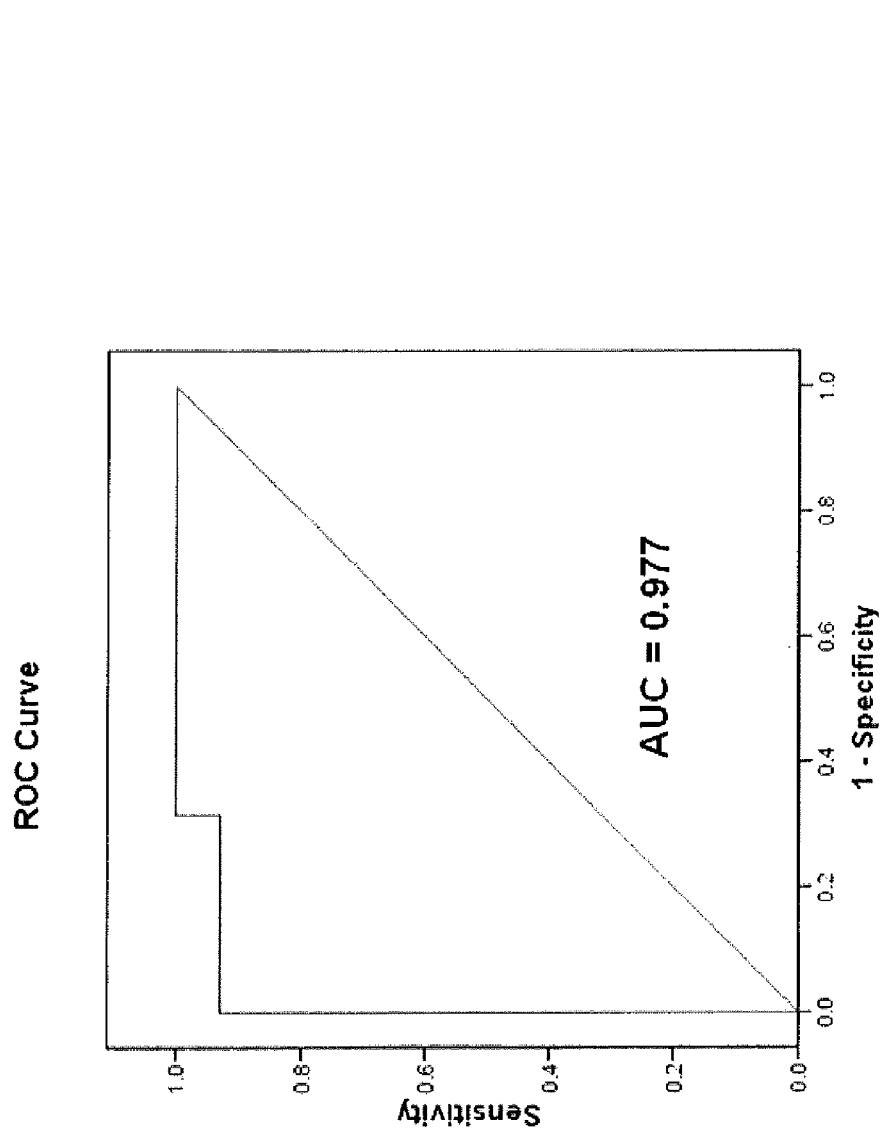

FIG. 10b: ROC curve illustrating combined test (see FIG. 10a) sensitivity and specificity for detecting CD (14 patients with CD were compared with 19 individuals from control and IBS groups). Area under the curve is 0.977. At combined test cut-off point=1.0: test sensitivity=92.9%; test specificity=100%. Combined test performance was superior compared to either EDN or calprotectin test.

Figure 10C:
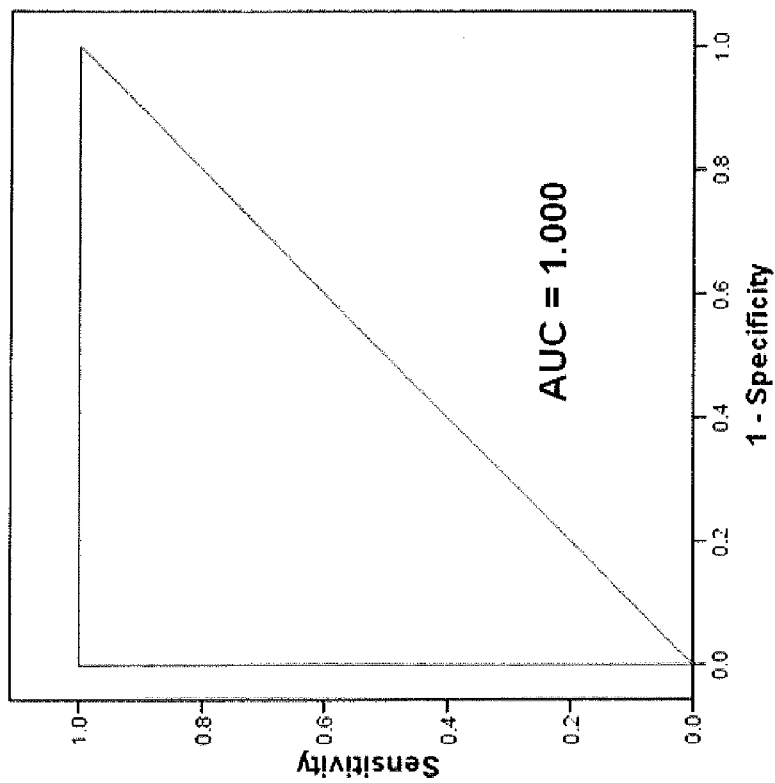

FIG. 10c: ROC curve illustrating combined test (see FIG. 10a) sensitivity and specificity for detecting UC (15 patients with UC were compared with 19 individuals from control and IBS groups). Area under the curve is 1.00. At combined test cut-off point=1.0: test sensitivity=100%; test specificity=100%. The combined test was equal to EDN test in correctly identifying all UC cases or inflammation-free subjects.

Figure 10D:
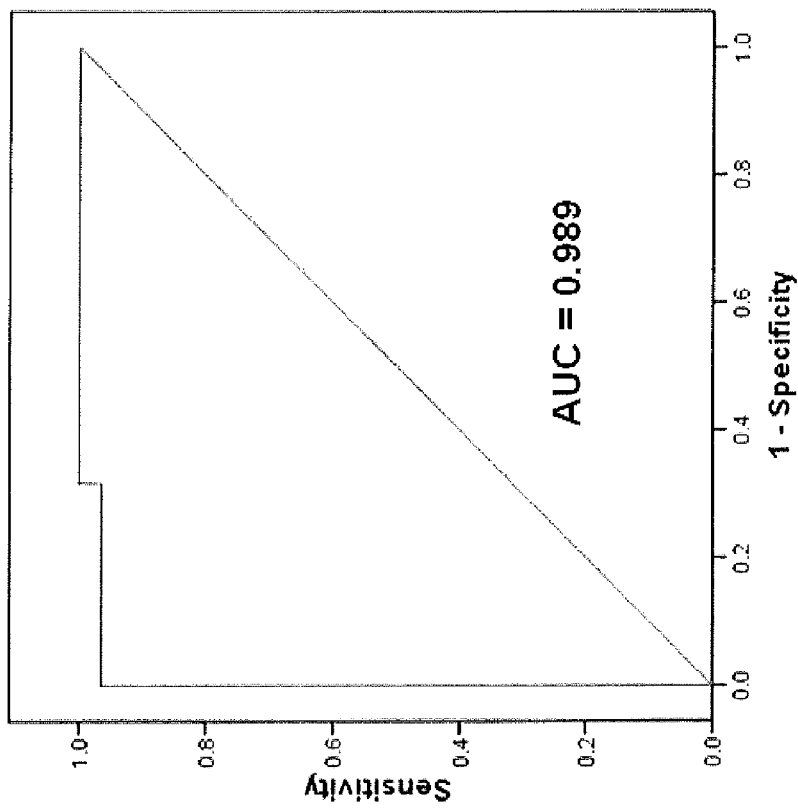

FIG. 10d: ROC curve illustrating combined test (see FIG. 10a) sensitivity and specificity for detecting IBD (29 patients with IBD were compared with 19 individuals from control and IBS groups). Area under the curve is 0.989. At combined test cut-off point=1.0: test sensitivity=96.6%; test specificity=100%. Combined test performance was superior compared to either EDN or calprotectin test due to better detection of CD cases.

Figure 11B:
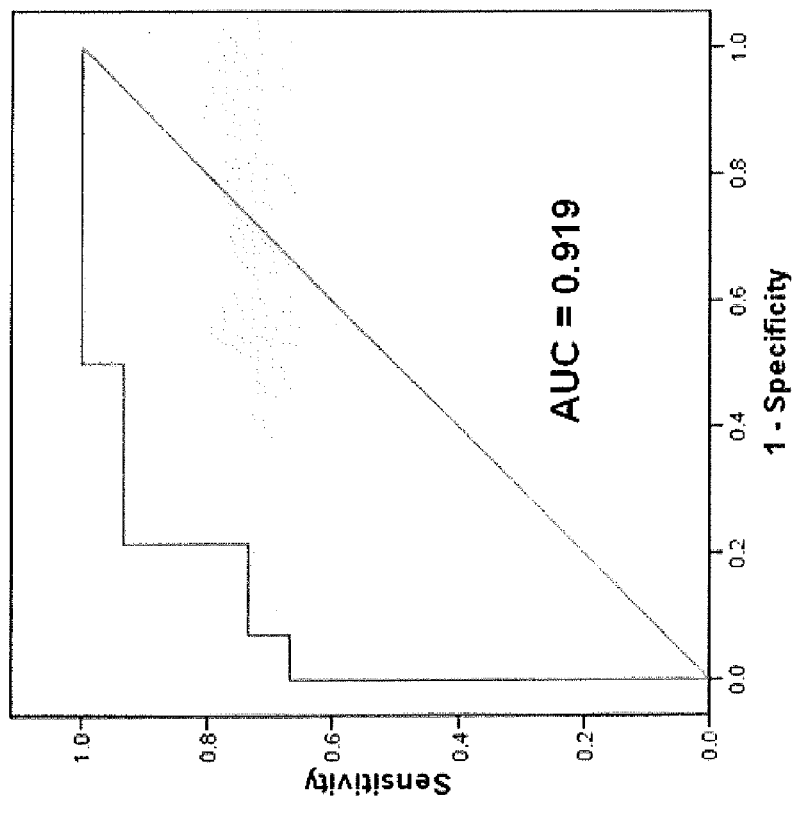

FIG. 11a: Application of the combined test with ICAM1 correction for discriminating UC from CD among IBD patients. Given that the absence of detectable ICAM1 was a characteristic feature of some CD patients, the results of the combined test (see FIG. 9) were modified by introducing a multiplier of 0.1 only in the cases where no ICAM1 could be detected in the corresponding sample. In all other cases the results were not changed. The figure shows ICAM1-corrected combined test results in 14 CD cases (white stars) and 15 UC cases (grey stars) demonstrating a significant difference between the two groups. The optimal cut-off point for the combined test (=4.0) providing the best combination of sensitivity and specificity obtained by the analysis of the corresponding ROC curve (see FIG. 11b). An alternative cut-off point=9.0 providing UC detection with 100% specificity is also shown.

FIG. 11b: ROC curve illustrating sensitivity and specificity of ICAM1-corrected combined test (see FIG. 11a) for discriminating UC from CD among IBD patients (14 patients with CD were compared with 15 patients with UC). Area under the curve is 0.919. At ICAM1-corrected combined test cut-off point=4.0: test sensitivity=93.3%; test specificity=78.6%. At ICAM1-corrected combined test alternative cut-off point=9.0 (targeting high test specificity): test sensitivity=60.0%; test specificity=100%.

Figure 12A:
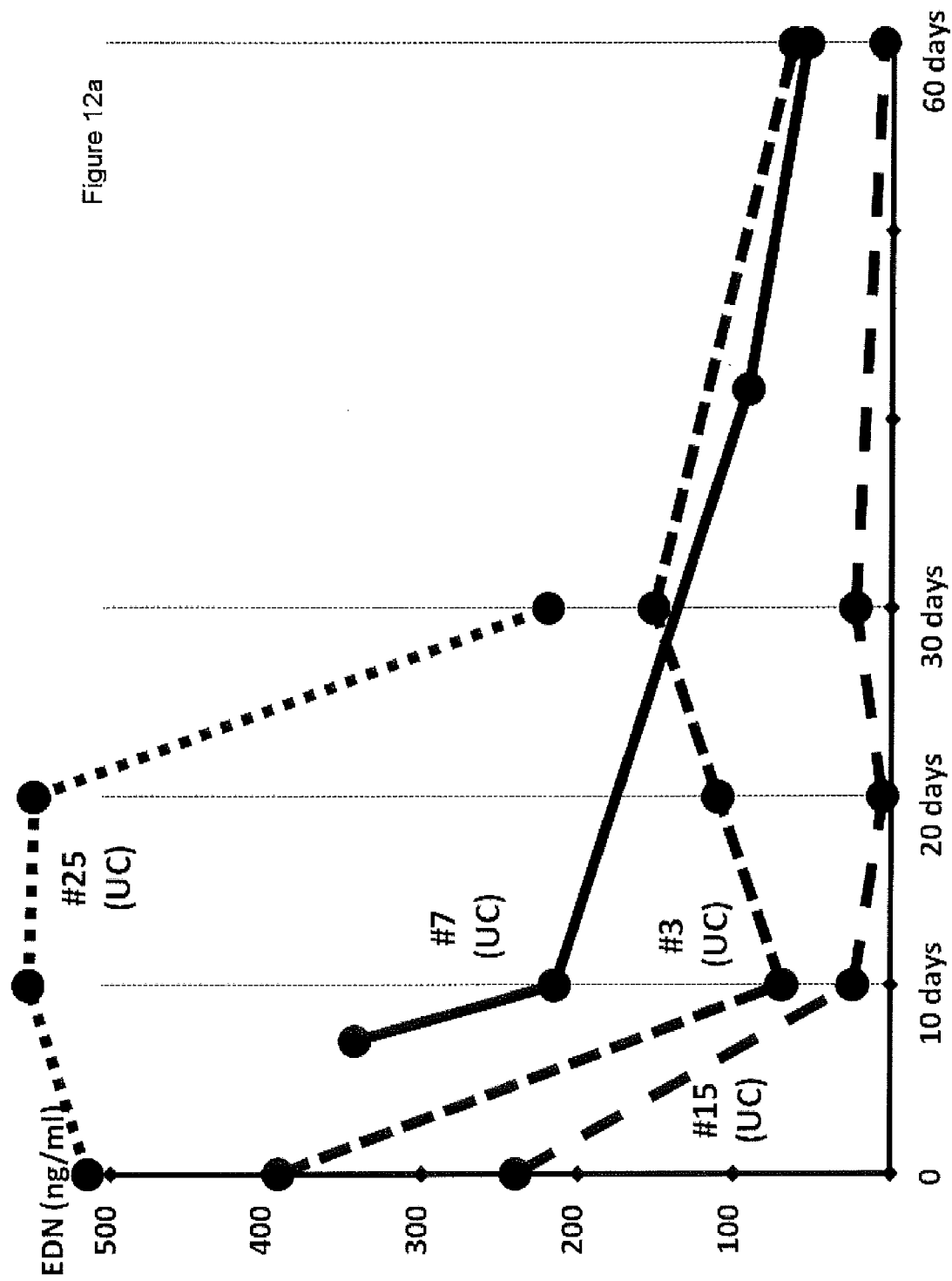

FIG. 12a: Dynamics of changes in EDN concentrations (ng/ml) in lysates of colonic mucocellular layer samples obtained from four IBD patients (all UC cases) before therapy initiation and at different time points during therapy. EDN concentration changes reflect changes in colonic inflammation intensity in these patients. Considerable decrease in EDN concentrations is observed in all four patients by day 30 following treatment initiation indicates reduction of inflammation intensity resulting from successful therapeutic interventions.

FIG. 12b: Dynamics of changes in EDN concentrations (ng/ml) in lysates of colonic mucocellular layer samples obtained from other four IBD patients (two UC and two CD cases) before therapy initiation and at different time points during therapy. Increasing or disorderly fluctuating EDN concentrations suggest that therapeutic interventions may require modifications in order to provide adequate anti-inflammatory effect in these patients.

Figure 13A:
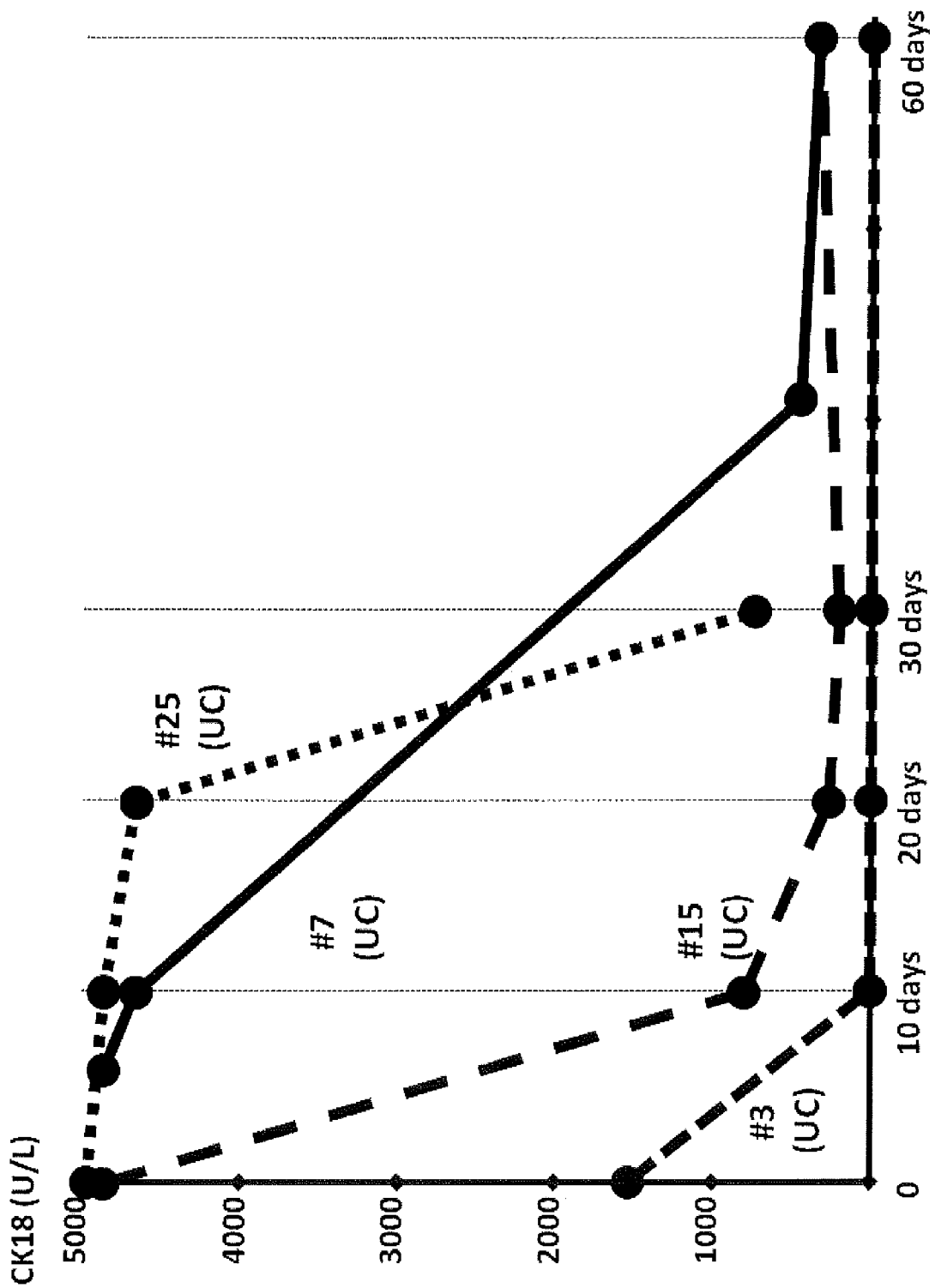

FIG. 13a: Dynamics of changes in soluble cytokzeratin-18 (CK18) concentrations (U/I) measured by M65 assay in lysates of colonic mucocellular layer samples obtained from four IBD patients (all UC cases already shown in FIG. 12a) before therapy initiation and at different time points during therapy. CK18 patterns are likely to reflect the presence of epithelial damage in the colonic mucosa of these patients. Considerable decrease in CK18 concentrations is observed in all four patients by day 30 following treatment initiation indicating positive therapeutic effect manifested by mucosal healing.

Figure 13B:
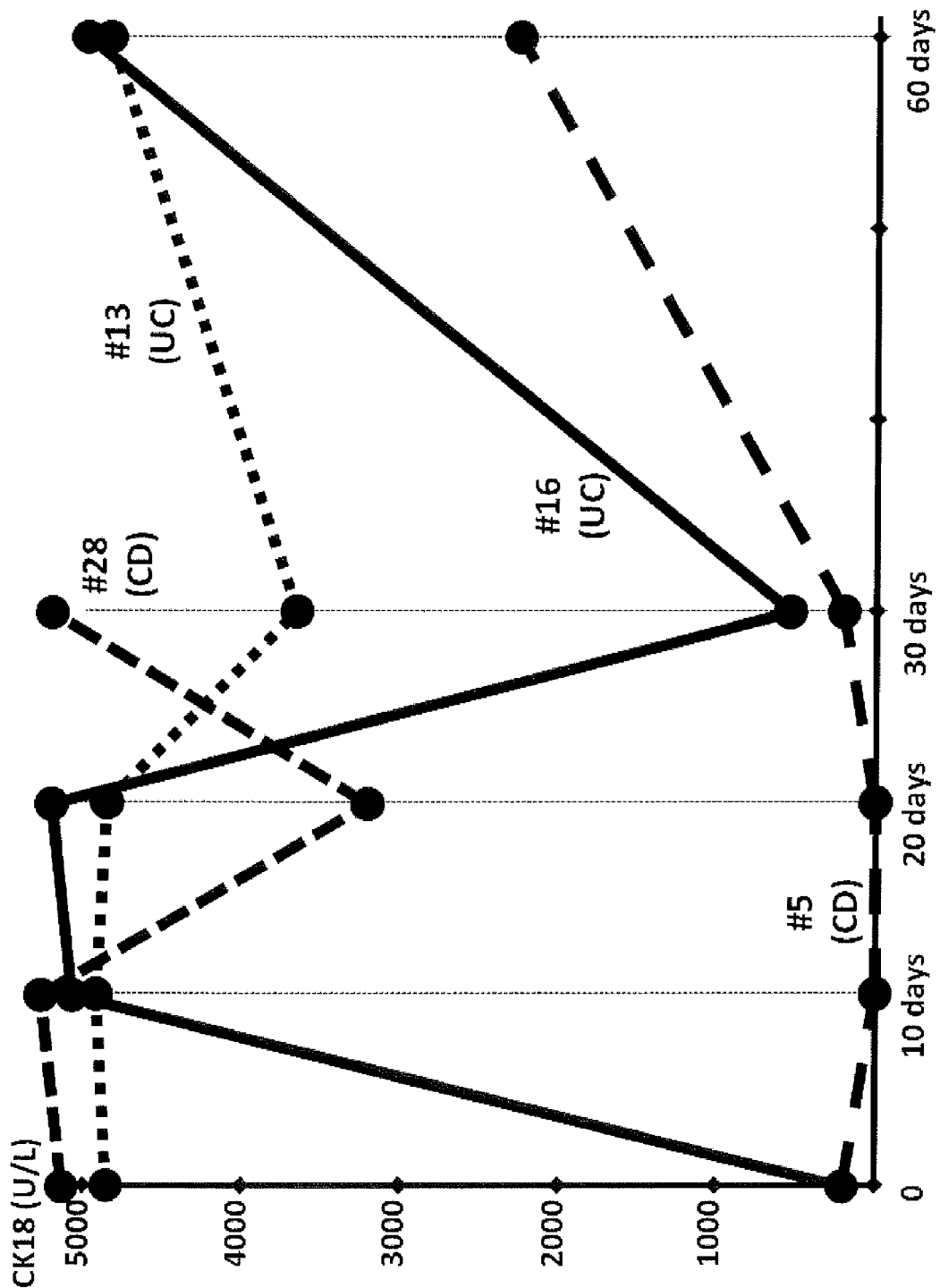

FIG. 13b: Dynamics of changes in soluble cytokeratin-18 (CK18) concentrations (U/I) measured by M65 assay in lysates of colonic mucocellular layer samples obtained from other four IBD patients (two UC and two CD cases already shown in FIG. 12b) before therapy initiation and at different time points during therapy. Persistently high or disorderly fluctuating CK18 concentrations suggest that therapeutic interventions may require modifications in order to provide adequate epithelial healing in these patients.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features being indicated as being preferred or advantageous.

As previously discussed there exists a need to develop new methods for the diagnosis of inflammatory bowel diseases. In particular, there exists a particular need to develop a non-invasive method for the detection of these diseases.

The inventors have surprisingly identified that a considerable portion of the colonic mucocellular layer is evacuated together with stool, and more importantly fragments of the mucocellular layer remain on the surface of the external anal/perianal area following defaectaion. Usually these fragments would be removed in the course of cleaning following defaecation. However, it has been identified that these fragments can be successfully collected and subsequently analysed. The present inventors have also surprisingly identified that within this sample a number of biomarkers, specifically IBD-specific biomarkers, can be accurately detected and their concentration levels measured, and moreover, that there exists a threshold value for these biomarkers wherein concentration values above this threshold is indicative of IBD.

Moreover, the inventors have identified that the mechanism of defaecation provides a level of physiological standardisation in the sample that can subsequently be obtained as a result from the surface of the external anal/perianal area. Such a level of uniformity in the sample cannot be obtained if the sample is obtained using an invasive procedure, such as using a swab to directly sample the rectal mucosa (internally) or by using previously devices for the collection of such a sample.

Figure 1:
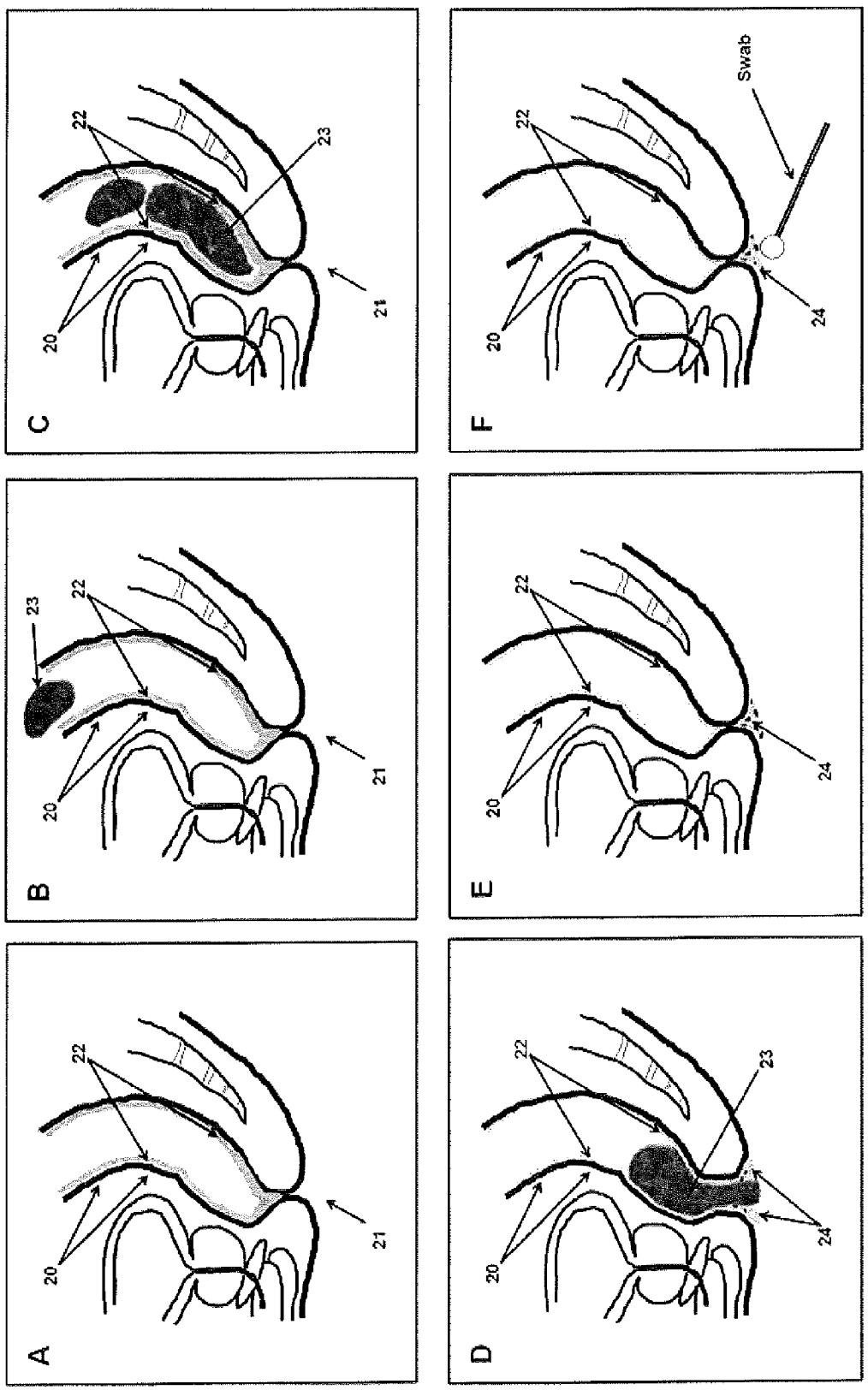
FIG. 1: shows a cross section of the human rectum, anus and adjacent organs

The physiological mechanisms behind this method of sample collection are presented in FIG. 1. It is evident that the existence and role of the mucocellular layer in the human large bowel is presently largely overlooked with only a few relevant publications (Loktionov, 2007; Loktionov et al., 2009; Loktionov et al., 2010).

FIGS. 1A & 1B shows that when the rectum is empty between two acts of defaecation the colonic mucocellular layer is not affected by the presence of faeces, which was demonstrated by its intrarectal collection (Loktionov et al., 2009; Loktionov et al., 2010). Once the rectum is filled with stool (see FIG. 10), the mucocellular layer comes into a close contact with stool, which is further enhanced by muscular contraction of the rectum preceding defaecation. This results in partial attachment of the mucocellular layer to excreted stool. This part of the mucocellular layer is then evacuated together with stool (FIG. 1D). The phenomenon is reflected by the detectable presence of mucocellular layer elements on the surface of excreted stool (Loktionov et al., 1998; Bandaletova et al, 2002; U.S. Pat. No. 6,187,546). At the same time it has been found that the position of the mucocellular layer between the intestinal wall and excreted faeces leaves a considerable part of the cell-containing mucus on the surface of the anal canal and eventually on the surface of the anal and perianal area (see FIGS. 1D & 1E). Although faecal contamination of various degrees is also present in this area following defaecation, the presence of colon-derived cellular material is significant. These conditions create an excellent opportunity for non-invasively collecting mucocellular layer fragments from the anal/perianal area as shown in FIG. 1F. Collection of mucocellular layer fragments from this site has never been attempted before.

It should also be noted that the colonic mucocellular layer should be depleted in the rectum following defaecation. For this reason the necessity of the distinct physiological act of defaecation as a prerequisite for sample collection according to the method disclosed in this invention constitutes an important natural standardizing factor. Furthermore, the necessity of collecting samples immediately after defaecation makes sample self-collection the preferable way of using the device. It should also be stressed that absolute non-invasiveness of the sample collection method makes repeated sample collection extremely easy (it can be repeated following the next defaecation without any harm).

Once a sample of the colonic mucocellular layer is collected, it is placed in a tube with a buffer or medium. Then the sample can be either shipped to a laboratory for analytical assessment or immediately analysed using a lateral flow assay or a biosensor-based quantitative test.

By 'inflammatory bowel disease' or 'IBD' is meant a group of chronic disorders involving bowel inflammation. Included within this group are Crohn's disease (including ileitis, Ileocolic, and colitis) and ulcerative colitis (including distal, proctitis, proctosigmoiditis, left-sided colitis, extensive colitis and pancolitis), Inflammatory bowel disease may also include microscopic colitis (comprising collagenous colitis and lymphocytic colitis), ischaemic colitis, diversion colitis, allergic colitis, indeterminate colitis and Behçet's disease.

The term 'eosinophil-derived neurotoxin' or 'EDN' refers to the protein encoded by the RNASE2 gene and can be represented by the following sequence (SEQ ID NO: 1):

```
SEQ ID NO: 1:
mvpklftsqi clllllglla vegslhvkpp qftwaqwfet qhinmtsqqc tnamqvinny qrrcknqntf llttfanvvn vcgnpnmtcp snktrknchh sgsqvplihc nlttpspqni sncryaqtpa nmfyivacdn rdqrrdppqy pvvpvhldri i
```

The nucleic acid sequence encoding EDN (M30510.1) is incorporated herein by reference.

The term 'calprotectin' refers to different heterodimers and tetramers of the proteins encoded by the S100 calcium-binding protein A8 (S100A8) gene and by the S100 calcium-binding protein A9 (S100A9) and can be represented by the following sequences (SEQ ID No: 2 and SEQ ID No: 3):

```
SEQ ID NO: 2:
mltelekaln siidvyhkys likgnfhavy rddlkkllet ecpgyirkkg advwfkeldi ntdgavnfqe flilvikmgv aahkkshees hke
```

The nucleic acid sequence encoding S1008A (NM_002964.4) is incorporated herein by reference.

```
                                        SEQ ID NO: 3
mtckmsqler nietiintfh qysvklghpd tlnggefkel vrkdlqnflk kenknekvie himedldtna dkqlsfeefi mlmarltwas hekmhegdeg pghhhkpglg egtp
```

The nucleic acid sequence encoding S100A9 (NM_002965.3) is incorporated herein by reference.

The term '5100A12' refers to the protein encoded by the S100A12 gene and can be represented by the following sequence (SEQ ID NO: 4).

```
SEQ ID NO: 4:
mtkleehleg ivnifhqysv rkghfdtlsk gelkqlltke lantiknikd kavideifqg ldanqdeqvd fqefislvai alkaahyhth ke
```

The nucleic acid encoding S100A12 (NM_005621.1.) is incorporated herein by reference.

The term 'ICAM1' or 'intracellular adhesion molecule 1' refers to the protein encoded by the ICAM1 gene and can be represented by the following sequence (SEQ ID NO: 5):

```
                                         SEQ ID NO: 5
mapssprpal pallvllgal fpgpgnaqts vspskvilpr ggsvlvtcst scdqpkllgi etplpkkell lpgnnrkvye lsnvqedsqp mcysncpdgq staktfltvy wtpervelap lpswqpvgkn ltlrcqvegg apranltvvl lrgekelkre pavgepaevt ttvlvrrdhh ganfscrtel dlrpqglelf entsapyqlq tfvlpatppq lvsprvlevd tqgtvvcsld glfpvseaqv hlalgdqrln ptvtygndsf sakasysvta edegtqrltc avilgnqsqe tlqtvtiysf papnviltkp evsegtevtv kceahprakv tlngvpaqpl gpraqlllka tpedngrsfs csatlevagq lihknqtrel rvlygprlde rdcpgnwtwp ensqqtpmcq awgnplpelk clkdgtfplp igesvtvtrd legtylcrar stqgevtrkv tvnvlsprye iviitvvaaa vimgtaglst ylynrqrkik kyrlqqaqkg tpmkpntqat pp
```

The nucleic acid enclosing ICAM1 (NM_000201.2) is incorporated herein by reference.

All references to the protein also encompass all alternatively spliced isoforms.

The term 'fragment' refers to a portion of the amino acid or nucelotide sequence that is less than the complete length and includes at least a minimum length capable of maintaining the biological properties required in the present invention.

The term 'variant' refers to the protein sequence where the amino acids are substantially identical to SEQ ID NO: 1, 2, 3, 4 or 5. A variant retains the biological function and activity of the protein in question. The variant may be achieved by modifications such as insertion, substitution or deletion of one or more of the amino acids. In a preferred embodiment, the variant thereof has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO:1, 2, 3 or 4.

An 'IBD-specific biomarker' refers to a protein (or nucleic acid) that causes or is associated with the presence of inflammatory bowel disease. Specifically, the biomarker may selected from the group consisting of eosinophil-derived neurotoxin (EDN), calprotectin, S100A12, ICAM1, CK-18, D-dimer, TNF-α, ASCA, pANCA, anti-GP2 antibodies, lactoferrin and total amount of human DNA in the sample. The biomarker may also be a cytokine.

A 'subject' as described herein can be any subject having an inflammatory bowel disorder. For example, the subject can be any mammal, such as a human, including a human IBD patient. Exemplary nonhuman mammals include a nonhuman primate (such as a monkey or ape) and a rodent, such as mouse or rat.

A lysis buffer' refers to any solution or buffer solution used for the purpose of lysing cells. The composition of the lysis buffer would be known to the skilled person. In one embodiment, the lysis buffer may comprise Tris-HCL, NaCl, Triton X-100. The lysis buffer may alternatively or additionally comprise EDTA, EGTA, SDS, deoxycholate, and/or NP-40.

The term 'treatment' refers to the management of a patient through medical or surgical means. The treatment improves or alleviates at least one symptom of a medical condition or disease and is not required to provide a cure. The treatment can encompass any known treatment for IBD. Examples include anti-inflammatory drugs. For example, the anti-inflammatory drug may be sulfasalazine, mesalamine, balsalazide, blsalazin and corticosteroids. Alternatively, the treatment may be an immune system suppressor. Examples include azathioprine, mercaptopurine, cyclosporine, infliximab, adalimumab, certolizumab pegol, methotrexate and natalizumab. Other treatments can include antibiotics (for example, metronidazole and ciprofloxacin), ICAM1 inhibitors (alicaforsen), anti-diarrheal drugs, laxatives, iron supplements, vitamin B12, calcium and vitamin D supplements or a patient-specific diet. Alternatively, the treatment may comprise surgery to remove part or all of the patient's intestine, colon and/or rectum.

The term 'antibody' as used herein refers to any immunolglobulin, preferably a full-length immunoglobulin. Preferably, the term covers monoclonal antibodies, polyclonal antibodies, multispecific antibodies, such as bispecific antibodies, intracellular antibodies (or intrabodies) and antibody fragments thereof, so long as they exhibit the desired biological activity. Antibodies may be derived from any species, but preferably are of rodent, for examples rat or mouse, human or rabbit origin. Alternatively, the antibodies, preferably monoclonal antibodies, may be humanised, chimeric or antibody fragments thereof. The term 'chimeric antibodies' may also include "primatised" antibodies comprising variable domain antigen-binding sequences derived from a non-human primate (e.g., Old World Monkey, Ape etc) and human constant region sequences. The immunoglobulins can also be of any type (e.g. IgG, IgE, IgM, IgD, and IgA), class (e.g., IgGI, IgG2, IgG3, IgG4, IgAI and IgA2) or subclass of immunoglobulin molecule.

The term 'monoclonal antibody' refers to a substantially homogenous population of antibody molecules (i.e. the individual antibodies comprising the population are identical except for possible naturally occurring mutations that may be present in minor amounts), produced by a single clone of B lineage cells, often a hybridoma. Importantly, each monoclonal has the same antigenic specificity—i.e. it is directed against a single determinant on the antigen.

The production of monoclonal antibodies can be carried out by methods known in the art. However, as an example, the monoclonal antibodies can be made by the hybridoma method (Kohler & Milstein, 1975), the human B cell hybridoma technique (Kozbor & Roder, 1983), or the EBV-hybridoma technique (Cole et al, 1985. Alternatively, the monoclonal antibody can be produced using recombinant DNA methods (see, U.S. Pat. No. 4,816,567) or isolated from phage antibody libraries using the techniques described in Clackson et al (1991) and Marks et al (1991).

Polyclonal antibodies are antibodies directed against different determinants (epitopes). This heterogenous population of antibody can be derived from the sera of immunised animals using various procedures well known in the art.

The term 'bispecific antibody' refers to an artificial antibody composed of two different monoclonal antibodies. They can be designed to bind either to two adjacent epitopes on a single antigen, thereby increasing both avidity and specificity, or bind two different antigens for numerous applications, but particularly for recruitment of cytotoxic T- and natural killer (NK) cells or retargeting of toxins, radionuclides or cytotoxic drugs for IBD treatment (Holliger & Hudson, 2005). The bispecific antibody may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO94/04690; Suresh et al, 1986; Rodrigues et al, 1993; Carter et al, 1992; Carter et al, 1995; Merchant et al, 1998).

Methods to prepare hybrid or bispecific antibodies are known in the art. In one method, bispecific antibodies can be produced by fusion of two hybridomas into a single 'quadroma' by chemical cross-linking or genetic fusion of two different Fab or scFv modules (Holliger & Hudson, 2005).

The term 'chimeric' antibody refers to an antibody in which different portions are derived from different animal species. For example, a chimeric antibody may derive the variable region from a mouse and the constant region from a human. In contrast, a 'humanised antibody' comes predominantly from a human, even though it contains non-human portions. Specifically, humanised antibodies are human immunoglobulins (recipient antibody) in which residues from a hypervariable region of the recipient are replaced by residues from hypervariable regions of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanised antibodies may comprise residues that are not found in the recipient antibody or in the donor antibody. These modifications are made to further refine antibody performance. In general, the humanised antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanised antibody optionally also will comprise at least a portion of an immunoglobulin constant region (Fc), typically that of a human immunoglobulin.

Recombinant antibodies such as chimeric and humanised monoclonal antibodies can be produced by recombinant DNA techniques known in the art. Completely human antibodies can be produced using transgenic mice that are incapable of expressing endogenous immunoglobulin heavy and light chains genes, but which can express human heavy and light chain genes. The transgenic mice are immunized in the normal fashion with a selected antigen. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995). For a detailed discussion of this technology for producing human antibodies and human monoclonal antibodies and protocols for producing such antibodies, see, for example, U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

The term 'antigen-binding fragment' in the context of the present invention refers to a portion of a full length antibody where such antigen-binding fragments of antibodies retain the antigen-binding function of a corresponding full-length antibody. The antigen-binding fragment may comprise a portion of a variable region of an antibody, said portion comprising at least one, two, preferably three CDRs selected from CDR1, CDR2 and CDR3. The antigen-binding fragment may also comprise a portion of an immunoglobulin light and heavy chain. Examples of antibody fragments include Fab, Fab', F(ab')2, scFv, di-scFv, and BiTE (Bi-specific T-cell engagers), Fv fragments including nanobodies, diabodies, diabody-Fc fusions, triabodies and, tetrabodies; minibodies; linear antibodies; fragments produced by a Fab expression library, anti-idiotypic (anti-Id) antibodies, CDR (complementary determining region), and epitope-binding fragments of any of the above that immunospecifically bind to a target antigen. For comparison, a full length antibody, termed 'antibody' is one comprising a VL and VH domains, as well as complete light and heavy chain constant domains.

The antibody may also have one or more effector functions, which refer to the biological activities attributable to the Fc region (a native sequence Fc region or amino acid sequence variant Fc region engineered according to methods in the art to alter receptor binding) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

The antibody can also be a functionally active fragment, derivative or analog of an antibody that immunospecifically binds to a target antigen. In this regard, functionally active means that the fragment, derivative or analog is able to elicit anti-idiotype antibodies that recognise the same antigen that the antibody from which the fragment, derivative or analog is derived recognised. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay), see, for example, Kabat (1980) and Kabat et al (1991).

The term 'antibody' may also include a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Furthermore, the antibody or antigen-binding fragments of the present invention may include analogs and derivatives of antibodies or antigen-binding fragments thereof that are either modified, such as by the covalent attachment of any type of molecule as long as such covalent attachment permits the antibody to retain its antigen binding immunospecificity. Examples of modifications include glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies or antigen-binding fragments of the present invention may also have modifications (e.g., substitutions, deletions or additions) in the Fc domain of the antibody. Specifically, the modifications may be in the Fc-hinge region and result in an increased binding for the FcRn receptor (WO97/34631).

In one aspect of the methods described herein, the concentration of at least one IBD-specific biomarker, or fragment or variant thereof, is measured in a sample of the colonic mucocellular layer and compared to a threshold value.

In one embodiment, the threshold value may be determined by determining the concentration of the IBD-specific biomarker in a group of one or more control subjects. Preferably this group comprises at least five control subjects. More preferably this group comprises at least ten control subjects.

Thus, in the methods described herein, the methods may further comprise the following steps:
a) obtaining a sample of the colonic mucocellular layer from at least one control subject and from the test subject;
b) measuring or determining the concentration levels of said IBD-specific biomarker (for example EDN, calprotectin, ICAM1 or S100A12) or a fragment or variant thereof in said sample from the at least one control subject and the test subject
c) comparing the observed concentration levels in a test subject to the concentration levels in at least one control subject, wherein a change, preferably an increase, in the concentration levels in the test subject indicates the presence of an IBD.

In one embodiment the at least one control subject represents a control or reference cohort and the concentration of the at least one IBD-specific biomarker is compared to the median concentration level in said control or reference cohort.

The control sample (i.e. the sample obtained from the at least one control subject) is taken from a reference cohort, that is one or more subjects of the same species (e.g., human subjects). The reference cohort is preferably healthy subjects. More preferably the subjects are believed not to have an IBD (or have inflammatory bowel syndrome (IBS), but not IBD). The individual members of a reference cohort may also share other similarities, such as similarities in stage of disease, previous treatment regimens, lifestyle (e.g., smokers or nonsmokers, overweight or underweight), or other demographics (e.g., age, genetic disposition).

In a further embodiment, the threshold value defines a fractile of a distribution of measured concentrations for a population of control subjects without IBD. Preferably, said fractile is a 0.9 or greater fractile. Preferably, said distribution is assumed to be a Gaussian distribution.

In an alternative embodiment, the threshold value identifies that said subject is IBD-positive with greater than a threshold value. In a further alternative embodiment, said threshold value is associated with a defined probability of determining that said subject has IBD, when said subject has IBD. Preferably, said defined probability is greater than 60%, preferably 65%, preferably 70%, preferably 75%, preferably 80%, preferably 85%, preferably 90%, preferably 95%, preferably 100%.

In an alternative embodiment, the concentration levels of a biomarker (for example, EDN, calprotectin, ICAM1 or S100A12) in a sample from a test subject can be measured and compared with a predetermined reference value. The 'predetermined reference value' or 'threshold concentration' (these terms are used interchangeably herein) can be established by skilled healthcare practitioners. For instance, the predetermined reference value can be established by measuring the levels of the biomarker in a normal population sample and correlating such levels with factors such as the incidence, severity, and/or frequency of developing IBD. Thus, a subject's concentration levels of the biomarker as compared against the concentration levels in a normal population can be indicative of whether the subject has IBD. Further, the predetermined reference value is preferably established by using the same assay technique as is used for measurement of the subject's biomarker level, to avoid any error in standardization.

In a preferred embodiment, the sample of the colonic mucocellular layer from the control subject may be obtained from the surface of the anal area following defaecation.

The invention also relates to a method for monitoring the effectiveness of a treatment for IBD. In a specific embodiment, the method comprises measuring the concentration levels of an IBD-specific biomarker over the course of a treatment period. If the concentration levels rise or stay the same compared to the levels pre-treatment or increase compared to a predetermined threshold value, the treatment can be concluded to be ineffective. Alternatively, if the concentration levels decrease compared to the levels pre-treatment or decrease compared to a predetermined threshold value, the treatment can be concluded to be effective. As a consequence the treatment may need to be altered or the dosage of the existing treatment. In this method, the test sample is from a patient who has received or is receiving treatment.

Thus, in one embodiment of the method for monitoring the effectiveness of a treatment the method may further comprise the steps of (i) optionally obtaining a pre-treatment sample from a patient prior to administration of the treatment; (ii) optionally detecting or measuring the concentration of the IBD-specific biomarker in the pre-treatment sample; (iii) obtaining one or more post-treatment samples from the subject at selected time intervals; (iv) determining the concentration levels of the IBD-specific biomarker in the post-treatment sample(s); (v) comparing the concentration levels of the IBD-specific biomarker in the pre-treatment sample with the concentration levels in the post-treatment sample or samples or comparing the concentration levels in the post-treatment samples taken at different time intervals; and (vi) optionally altering the administration of the treatment to the subject accordingly.

The invention also relates to a method for monitoring disease relapse in an IBD patient in remission. In a specific embodiment, the method comprises measuring the concentration levels of an IBD-specific biomarker over specified time intervals. As IBD is a life-long condition and so there is no upper time-limit for measuring the concentration levels of an IBD-specific biomarker in an IBD patient in remission. This will be the case unless the patient undergoes a radical procedure such as colectomy. As an example of the frequency, the method could comprise measuring the concentration levels of an IBD-specific biomarker once every 12 months, preferably every 6 months, more preferably every 3 months. The patient may or may not still be receiving treatment for IBD. If the concentration levels rise over the specified time intervals, the patient can be concluded to be out of remission—i.e. the disease has relapsed. Alternatively, if the concentration levels rise to be equal or greater than a threshold value the patient can be concluded to be out of remission. As a consequence the treatment may need to be altered (or the dosage of an existing treatment altered) or treatment resumed all together. However, if the concentration levels stay the same or decrease over the specified time intervals, or if the levels decrease with respect to a threshold value, the patient can be concluded to be still in remission.

Thus, in one embodiment of the method for monitoring for disease relapse in an IBD patient in remission, the method may further comprise the steps of (i) obtaining a sample from an IBD-patient in remission at one or more time intervals, ii) comparing said concentration levels to a threshold value and determining a disease relapse when the concentration of the IBD-specific biomarker is equal to or greater than a threshold value and iii) optionally re-starting or altering the administration of treatment to the subject accordingly.

The invention also relates to a method of selecting a treatment for an IBD patient. In a specific embodiment, the method comprises measuring the concentration levels of an IBD-specific biomarker and comparing the concentration level to a threshold value. If the concentration of the IBD-specific biomarker is above this threshold an IBD-specific treatment may be selected. However, if the concentration of the IBD-specific biomarker is below this threshold, no treatment may be selected. In one example, the concentration of the IBD-specific biomarker is indicative that the patient will respond to a specific type of therapy. This specific therapy may be directed against or be specific to the IBD-specific biomarker in question. For example, if the IBD-specific biomarker is ICAM1, the IBD-specific treatment may be alicaforsen. Alternatively, if the IBD-specific biomarker is TNF-α, the IBD-specific treatment may be infliximab. Accordingly, we also describe herein a method of tailoring or selecting a specific IBD-treatment depending on which IBD-specific biomarker is elevated in the patient's sample.

Accordingly, we further describe here, a method of predicting a response to a particular IBD-specific treatment (for example a ICAM1-targeted therapy or other IBD biomarker-targeted therapy), the method comprising measuring the concentration levels of at least one IBD-specific biomarker, comparing the concentration level(s) to a threshold value and determining whether a subject will respond to a particular IBD-specific treatment depending on whether the concentration of the IBD-specific biomarker is equal to or greater than a threshold value.

The threshold value for an IBD-specific biomarker may be any threshold value already mentioned above.

We further describe herein, a method for assessing colonic mucosa damage. In other words, we describe a method for assessing whether the colonic mucosa is healthy.

Preferably, the method comprises measuring the concentration levels of at least one epithelial damage-specific biomarker, comparing the concentration level(s) to a threshold value and determining that the colonic mucosa is damaged when the concentration of at least one epithelial damage-specific biomarker is equal to or greater than a threshold value.

The term 'epithelial damage specific biomarkers' means biomolecules released during epithelial cell death or their metabolites. Examples include proteins such as soluble cytokeratine-18 (CR-18) and intestinal fatty acid binding protein (1-FATP) and smaller molecules such as α-amino acide citrulline.

In one embodiment the epithelial damage-specific biomarker is CK-18 (Cytokeratin-18) and the threshold value is, or is equivalent to 300 U/L when the collected sample is lysed in 3 ml of lysis buffer.

In an alternative embodiment the concentration of CK-18 is, or is equivalent to a value, equal to or greater than 500 U/L when the collected sample is lysed in 3 ml of lysis buffer. In a further alternative embodiment the concentration of CK-18 is or is equivalent to a value, equal or greater than a concentration value within the range 100 U/L to 35 U/L when the collected sample is lysed in 3 ml of lysis buffer.

In the methods described herein, the concentration of the IBD-specific biomarker (for example calprotectin, EDN, ICAM1 or S100A12) can be determined by measuring protein levels (i.e. protein concentration) of the respective IBD-specific biomarker. In one embodiment protein levels can be measured by contacting the sample with at least one binding agent, such as an antibody, that is capable of specifically binding the IBD-specific biomarker in question.

In the embodiments of this invention where one uses antibodies against a protein IBD-specific biomarker for diagnostic purposes, one can select any immunogenic fragment of the biomarker peptide to raise an antibody as is well known to one skilled in the art. The fragments that are immunogenic will lead to generation of antibodies. Protein fragments can be readily screened for immunogenic activity. Preferably, one uses monoclonal antibodies, but one can also use polyclonal antibodies. One can perform an immunohistochemical analysis using a polyclonal or monoclonal antibody raised against the entire biomarker peptide, or any fragments thereof.

In a further embodiment, the method further comprises determining whether the antibody has bound to the protein—i.e. whether an antibody-antigen complex has formed. In one embodiment, the formation of an antibody-antigen complex is measured using immunoassay. In one example the immunoassay is an ELISA kit. Alternatively bound antibody can be detected using any method known in the art. Examples include 2D gels and ID SDS-PAGE followed by western blotting, dot-blots, and flow cytometry. Alternatively bound antibody is measured using a lateral flow assay or in a quantitative biosensor-based assay employing electrochemical biosensors.

Accordingly, the methods further comprise detection or quantitation of the antigen-antibody complex. Such methods would be well known to the skilled person. For example, any chemical that detects antigen-antibody binding may be used in the practice of the invention. In some embodiments, the detection chemicals comprise a labelled polymer conjugated to a secondary antibody. For example, a secondary antibody that is conjugated to an enzyme that catalyses the deposition of a chromogen at the antigen-antibody binding site may be provided. Such enzymes and techniques for using them in the detection of antibody binding are well known in the art. In one embodiment the secondary antibody is conjugated to an HRP-labelled polymer. Alternatively, the antigen-antibody complex can be detected using any commercial antibody binding detection system. Examples include BIO-PLEX by Bio-Rad and fluorescent labels.

Thus, in one embodiment of the methods of the invention, the methods further comprise the following steps:

(a) contacting a test sample from a subject with a binding agent specific for the biomarker in question, e.g. an antibody as described herein, which is directly or indirectly labeled with an enzyme;
(b) adding a substrate for the enzyme wherein the substrate is selected so that the substrate, or a reaction product of the enzyme and substrate, forms fluorescent complexes;
(c) quantitating protein concentration levels in the sample by measuring fluorescence of the fluorescent complexes; and
(d) comparing the quantitated levels to that of a standard.

Another embodiment of the invention comprises the following steps:
(a) incubating a test sample with a first antibody specific for the IBD-specific biomarker in question which is directly or indirectly labeled with a detectable substance, and a second antibody specific for the biomarker which is immobilized;
(b) separating the first antibody from the second antibody to provide a first antibody phase and a second antibody phase;
(c) detecting the detectable substance in the first or second antibody phase thereby quantitating protein concentration in the biological sample; and
(d) comparing the quantitated protein levels with a control or threshold value.

In an alternative embodiment, the concentration of the IBD-specific biomarker can be determined by measuring expression levels of the respective IBD-specific biomarker. This may comprise detection or measurement of DNA or RNA of the IBD-specific biomarker. Methods to detect RNA or DNA levels in a sample are well known to the skilled person and include any nucleic-acid hybridisation-based technique or amplification-based technique such as PCR (including all forms of PCR, such as real-time), a lateral flow assay or an electrochemical biosensor-based assay.

Kits for practicing the methods of the invention are further provided. A 'kit' refers to any manufacture (e.g., a package or a container) comprising at least one reagent, e.g. a binding agent such as an antibody, for specifically detecting the concentration levels of an IBD-specific biomarker described herein. The kit may be promoted, distributed, or sold as a unit for performing the methods of the present invention. Additionally, the kits may contain a package insert describing the kit and methods for its use. The kit may also comprise a solid support such as microtiter multi-well plates, a lateral flow assay or an electrochemical biosensor-based assay.

For example, the kit can contain reagents, tools, and instructions for determining an appropriate therapy for an IBD patient. Such a kit can include reagents for collecting a sample from a patient, such as a swab, and reagents for processing the sample. The kit can also include one or more reagents for detecting the concentration levels of the biomarker. In an alternative embodiment, the kit may also comprise one or more reagents for performing a gene expression analysis, such as reagents for performing RT-PCR, Northern blot, Western blot analysis, or immunohistochemistry to determine biomarker expression levels in a patient sample. Appropriate buffers for the assays can also be included.

A kit can contain separate containers, dividers or compartments for the reagents and informational material.

In particular embodiments, kits for practicing the methods of the invention are provided. Such kits are compatible with both manual and automated immunohistochemistry techniques (e.g., cell staining). These kits comprise at least one antibody capable of specifically binding to at least one of the IBD-specific biomarkers of the present invention. Chemicals for the detection of antibody binding to the biomarker in question, a counterstain, and a bluing agent to facilitate identification of positive staining cells are optionally provided. Alternatively, the immunochemistry kits of the present invention are used in conjunction with commercial antibody binding detection systems, such as, for example the BIOPLEX assay by Bio-Rad. Any chemicals that detect antigen-antibody binding may be used in the practice of the invention. In some embodiments, the detection chemicals comprise a labelled polymer conjugated to a secondary antibody. For example, a secondary antibody that is conjugated to an enzyme that catalyses the deposition of a chromogen at the antigen-antibody binding site may be provided. Such enzymes and techniques for using them in the detection of antibody binding are well known in the art. In one embodiment, the kit comprises a secondary antibody that is conjugated to an HRP-labelled polymer. Chromogens compatible with the conjugated enzyme (e.g., DAB in the case of an HRP-labeled secondary antibody) and solutions, such as hydrogen peroxide, for blocking non-specific staining may be further provided. The kits of the present invention may also comprise a counterstain, such as, for example, hematoxylin. A bluing agent (e.g., ammonium hydroxide) may be further provided in the kit to facilitate detection of positive staining cells.

In another embodiment, the immunohistochemistry kits of the invention comprise at least two reagents, e.g., antibodies, for the detection of more than one IBD-specific biomarker. Each antibody may be provided in the kit as an individual reagent or, alternatively, as an antibody cocktail comprising all of the antibodies directed to the different biomarkers of interest. Furthermore, any or all of the kit reagents may be provided within containers that protect them from the external environment, such as in sealed containers. Positive and/or negative controls may be included in the kits to validate the activity and correct usage of reagents employed in accordance with the invention. Controls may include samples, such as tissue sections, cells fixed on glass slides, etc., known to be either positive or negative for the biomarker in question. The design and use of controls is standard and well within the routine capabilities of those of ordinary skill in the art.

EXPERIMENTAL

The present invention describes a new diagnostic method for IBD detection and intestinal inflammation intensity assessment comprising the following key elements that can be combined as a sequence of steps:
1. Non-invasively obtaining by self-collection a sample of material rich in fragments of colonic mucocellular layer by swabbing the anal area of a human subject suspected of being affected with inflammatory bowel disease immediately following bowel opening;
2. Preserving the obtained sample and preparing it for quantitative protein analysis by buffer change followed by the lysis of collected cells, cryopreservation and pre-analysis dilution;
3. Assessing the obtained samples cytologically, wherein cytological patterns can be indicative of the presence or absence of said inflammatory bowel disorder and IBD type (ulcerative colitis or Crohn's disease);
4. Quantitatively determining the levels of biomarkers in said sample, wherein biomarker levels indicate the presence or absence of said inflammatory bowel disorder and provide an estimate of inflammation intensity;
5. Quantitatively determining the levels of biomarkers in said sample, wherein biomarker levels indicate the presence or absence of said inflammatory bowel disorder and provide an estimate of inflammation intensity when the said disorder is ulcerative colitis (UC);

6. Quantitatively determining the levels of biomarkers in said sample, wherein biomarker levels indicate the presence or absence of said inflammatory bowel disorder and provide an estimate of inflammation intensity when the said disorder is Crohn's disease (CD);

7. Determining the levels of biomarkers from the group comprising EDN, calprotectin, protein S100A12, intercellular adhesion molecule 1 (ICAM-1), soluble cytokeratin 18 (epithelial cell death marker), D-dimer (blood coagulation marker), M2-PK, TNFα, pANCA, ASCA, anti-GP2 antibodies, lactoferrin and total human DNA in said samples in order to further characterise IBD type (UC or CD), disease severity, efficiency of applied therapy and probability of response to particular therapeutic schemes;

8. Applying combined detection of levels of a combination or panel of protein biomarkers in said samples for complete characterisation of an individual with diagnosed or suspected IBD in order to determine the precise diagnosis and work out the most suitable therapeutic strategy.

This invention presents a combination of elements that provide a new method for IBD diagnosis, differentiation between IBD types (UC and CD), intestinal inflammation intensity monitoring and treatment efficiency assessment. Application of different biomarkers also provides means for assessing IBD-related damage to colorectal epithelium and selecting adequate therapeutic modalities.

The first key element of the new method is the use of a simple swab designed for non-invasively collecting (self-collecting) material from the anal area of a human subject suspected to have IBD following natural act of defaecation. The principle of the material collection method was described generally in our previous patent application WO2012/150453. The current working version of the swab is depicted in FIG. 2. One specific feature of the swab is its spherical shape providing additional uniformity of the area of contact with human body surface during sample collection. The shape and size (8 mm in diameter) of the collecting element of the swab also prevent from inadvertently introducing the swab in the anal canal during sample collection. The collecting element of the swab is covered with fibre with hydrophilic properties (flocked nylon) as described by Triva in U.S. Pat. No. 8,317,728. The fibre provides efficient sample collection and easy release of the collected material once the swab is placed in a buffer medium providing cell lysis. The rod of the swab has a breaking point at 100 mm from the end of the collecting element (FIG. 2). This allows breaking the proximal end of the swab rod off once a collected sample is placed into a 15 ml tube containing 3 ml of sample-preserving medium. The swabs prepared for sample collection are sterilised and provided to users sealed in plastic pockets.

The other elements of the invention are further described by referring to examples from a clinical trial that comprised groups of 29 IBD patients, 11 IBS patients and 8 healthy volunteers. The IBD patients all had a confirmed diagnosis of either ulcerative colitis (UC—in 15 cases) or Crohn's disease (CD—in 14 cases) and had presented at the clinic because of a flare-up of their disease. IBS patients were people with colorectal symptoms who were examined by colonoscopy and diagnosed to have IBS (IBD was excluded by clinicians). These people had presented at the clinic due to their symptoms. Control samples were obtained from a group of healthy volunteers without gastrointestinal symptoms or history of any disorders affecting gastrointestinal tract. All samples were taken by patients and healthy controls at home (self-collection). In the IBD group the first sample was taken from each patient prior to them starting on a course of medication intended to control their symptoms. Samples were then taken at day 10, 20, 30 and 60. The aim was to create an initial reference point before treatment (day 0-1) and then sample each patient twice while the symptoms of the flare-up were declining (day 10 and day 20), at day 30, when the patient's symptoms were often resolved and at day 60 in order to provide a follow-up point. Patients with IBS and healthy volunteers (controls) provided samples only once.

Each trial participant was given material collection kits (one kit per collection point) comprising the following essential elements:
  two swabs;
  a sample tube containing material-preserving buffer (see below);
  one sampling card containing two microscope slides with two windows for preparing smears for cytological analysis;
  fixative (spray-bottle) for cytological samples.

All trial participants were instructed to use the kit as follows:

1. Following a bowel movement (before using toilet paper/wipes) to unwrap one swab and gently press the swab tip against the surface of the exterior anal region to collect a sample onto tip (collecting element).
2. To open a preserving medium-containing tube (15 ml polypropylene laboratory tube), place the swab into the liquid and break off at the break point. To screw cap tight.
3. To unwrap the second swab and repeat the collection procedure described in (1).
4. To transfer a thin layer of material from the swab tip to both of the sampling card card windows.
5. To spray the windows of the sample card using the fixative-containing sprayer provided.

Preservation of samples at room temperature was achieved by using a preserving medium causing protein stabilisation by precipitation. The medium had the following composition: Tris—10 mM; NaCl—150 mM; EDTA—10 mM; Ammonium Sulfate—saturated; pH—7.5. 3 ml of the preserving medium was used for one collected sample. This sample preservation principle is described in our previous patent application (WO2012/150453).

Following the described collection procedure the samples were sent to the laboratory for analysis. No diagnostic information was provided to laboratory staff before sample analysis was completed and its results recorded.

Upon arrival to the laboratory sample tubes were opened, swabs temporarily removed and carefully placed in empty Eppendorf tubes. The sample tubes were centrifuged at 1920G (4500 RPM) for 5 minutes. Following centrifugation the resulting supernatant was carefully removed and discarded. The swabs were returned to the corresponding tubes and 3 ml of a lysis buffer were added to each sample tube. Lysis buffer composition was as follows: Tris—10 mM; NaCl—150 mM; Triton X-100—0.1%; pH—7.5M. Accelerated sample lysis was achieved by vigorously shaking the tubes for 15 minutes at 8000 rpm using Vortex (Vortex-Genie-2, Scientific Industries Inc.) equipped with a tube-holding rack. Alternatively sample lysis can be achieved by vertical rotation of the tubes for 30 minutes. 200 µl aliquots were prepared from each sample. The prepared aliquots were immediately frozen and kept at −80° C. until use.

Quantitative protein analysis in sample lysates was performed using commercially available ELISA kits for the following proteins: EDN—EDN ELISA Kit (Medical & Biological Laboratories Co., LTD, Japan); Calprotectin—CALPRO Calprotectin ELISA Test (ALP) (Nova Tec Immunodiagnostica GmbH, Germany); Protein S100A12—CircuLex S100A12/EN-RAGE ELISA Kit (CycLex Co., Ltd, Japan); ICAM-1—sE90548Hu Enzyme-linked Immunosorbent Assay Kit for ICAM1 (Uscn Life Science Inc., China/USA); Soluble CK18-M65 EpiDeath ELISA (PEVIVA AB, Sweden); D-dimer—E90506Hu Enzyme-linked Immunosorbent Assay Kit for D-dimer (Uscn Life Science Inc., China/USA); Glyceraldehyde-3-phosphate dehydrogenase (GAPDH)—GAPDH InstantOne ELISA (eBioscience, Inc., USA). In addition, total protein amount in all samples was determined using QuantiPro BCA Assay Kit (Sigma-Aldrich Co. LLC., USA).

ELISA assays were performed according to manufacturers' instructions. However, sample preparation and dilution had to be optimised for each particular assay. Upon defreezing samples were diluted: 1/5 for EDN and ICAM-1 detection; 1/50 for calprotectin and S100A12 detection, 1/10 for D-dimer and total protein detection. Undiluted samples were used for soluble CK18 and GAPDH detection. All results were expressed as protein concentrations (activity units for CK-18) and recalculated for the original sample lysates presuming that 3 ml of the initial preserving medium was replaced with 3 ml of the lysis buffer as described above.

Sample preservation and preparation for quantitative biomarker analysis, in particular protein analysis by ELISA comprising steps of buffer change & cell lysis, cryopreservation and pre-analysis dilution constitutes the second key element of the new method.

One of two slides with fixed smears prepared during sample collection was stained with haematoxylin and eosin. The remaining fixed smears were kept at −20° C. and used for immunocytochemical visualisation of target proteins when needed. All stained slides were thoroughly analysed microscopically. Photomicrographs have been made using Olympus DP-72 camera.

FIG. 3 shows photomicrographs demonstrating cytological patterns in the samples obtained from a healthy volunteer (FIG. 3a), a patient with UC (FIG. 3b) and a patient with proximal (ileal) CD (FIG. 3c). It is evident that colorectal mucocellular layer samples from healthy volunteers contain only small amounts of exfoliated normal colonocytes. In contrast, samples obtained from UC patients (FIG. 3b) are characterised by abundant presence of free inflammatory cells, especially polymorhonuclear leukocytes comprising neutrophils (multiple cells with segmented nuclei) and eosinophils. Macrophages, lymphocytes and sometimes mast cells and basophils can also be found. In patients with CD, especially in ileal CD cases partially damaged leukocytes ("leukocyte shadows" shown in FIG. 3c) were often observed. It can be concluded that non-invasively collected samples of colorectal mucocellular layer present a good material for diagnostic cytological analysis in the area of IBD.

Key elements 4-7 of the present invention are illustrated by findings of our clinical study presented below.

Results of quantitative assessment of a group of protein biomarkers in healthy volunteers and IBD patients before treatment initiation are presented in FIGS. 4-11.

The first clinically important endpoint addressed by the present invention is the detection of the presence of an inflammatory process in the gut allowing making a diagnostic conclusion on the presence of IBD. Comparison of concentrations of protein biomarkers in colorectal mucocellular layer samples non-invasively collected from IBD patients (with either CD or UC) or individuals without IBD (control and IBS groups) allowed concluding that both EDN and calprotectin assays demonstrated very good diagnostic performance (see FIGS. 4-7). EDN assay appeared to be the most efficient among all tested methods. The results of this test generally followed the normal (Gaussian) distribution, and it was remarkable that EDN concentrations were uniformly low in all samples obtained from inflammation-free controls and IBS patients (see FIG. 4a). Therefore it was justified to pool results from these two groups together and compare the pooled set to patients with CD, UC and all IBD cases. All EDN concentration results obtained among controls and IBS patients were below 24 ng/ml. This EDN concentration value is slightly above the 0.975 fractile of the distribution of control values often used as the discrimination threshold (cut-off point) in diagnostic tests (Linnet, 1985). Given that numbers of subjects in the study groups were limited, it can be conservatively inferred that the threshold concentration value (cut-off point) for this EDN test should be within the range between 15 ng/ml and 35 ng/ml if the procedure of sample collection, preparation and analysis described in this invention is used. EDN concentration determination used as a diagnostic test was especially efficient in detecting UC (FIG. 4a) with perfect (100%) sensitivity and specificity (FIG. 4c). This test also performed well for diagnosing CD in most cases (FIG. 4a). When applied for overall IBD detection (see FIGS. 5a & 5b), EDN measurement showed that average concentration of this protein among IBD patients was 24.9 times higher than among IBD-free individuals (FIG. 5a). At the optimal cut-off point of 24 ng/ml the EDN-based test provided sensitivity of 86.2% and specificity of 100% for IBD detection (see ROC curve presented in FIG. 5b).

The results of calprotectin test also followed the normal (Gaussian) distribution, and calprotectin concentrations were uniformly low (below 4.7 mg/ml) in all in all samples obtained from inflammation-free controls and IBS patients (see FIG. 6a). This allowed using the concentration of 4.7 µg/ml as the optimal cut-off point worked out in a way similar to that described above for EDN. It could be conservatively inferred that the threshold concentration value (cut-off point) for the calprotectin test should be within the range between 3.5 µg/ml and 6.0 µg/ml if the procedure of sample collection, preparation and analysis described in this invention is used. Calprotectin quantification performance appeared to be slightly inferior compared to EDN for diagnosing UC (FIGS. 6a & 6c), but detected CD as efficiently as the EDN-based test (compare FIGS. 6b and 4b). Moreover, calprotectin assay appeared to work better for detecting cases of proximal (ileal) CD (see FIG. 6a and corresponding legend). Calprotectin test could also be successfully applied for overall IBD detection (FIGS. 7a & 7b). Average calprotectin concentration among IBD patients was 9.1 times higher than among IBD-free subjects (FIG. 7a). At the optimal cut-off point of 4.7 µg/ml this test had sensitivity of 79.3% and 100% specificity when applied for overall IBD detection (see ROC curve presented in FIG. 7b).

Other tested protein biomarkers appeared to be less efficient for diagnosing IBD. Although quantification of both S100A12 (FIG. 8) and ICAM1 (FIG. 9) allowed to identify most of UC cases, the performance of these tests for CD detection was poor. Moreover, result distributions for these biomarkers deviated from the normal (Gaussian) distribution making the determination of the cut-off points complicated. It should, however, be noted that an obvious result distribution bimodality for these markers existed within the CD group. This bimodality was especially pronounced when ICAM1 assay was applied. No detectable ICAM1 could be found in seven (50%) out of 14 CD cases. In contrast, ICAM1 was detectable and usually present at high concentrations in all patients with UC (FIG. 9). The absence of ICAM1 in a significant proportion of CD patients could be used for distinguishing between UC and CD (see below).

The remaining biomarkers (CK-18 and D-dimer) could not be used for IBD diagnosis since their presence was detected only in some (more severe) cases and appeared to be more suitable for IBD treatment efficiency assessment (see below).

The tests based on EDN and calprotectin quantification allowed identifying most IBD cases, but their performance for CD detection, although good, was limited compared to the excellent UC detection rate. It was, however, noticed that different CD cases were missed by the two tests (see legends to FIGS. 4b and 6b), therefore it appeared to be beneficial to combine the two tests in order to achieve a better rate of CD detection. The outcome of each of the tests could be presented as a ratio of the obtained result and test optimal cut-off point providing the best combination of sensitivity and specificity (in our case—24 ng/ml for EDN and 4.7 µg/ml for calprotectin). In this setting the ratio=1.0 served as an obvious cut-off point of choice. Once these calculations were done, a pair of ratios became available for each case (Ratio EDN & Ratio Calprotectin). If the higher ratio result was selected as the outcome of this combined test (i.e. Combined Test Result=Ratio EDN if Ratio EDN≥Ratio Calprotectin and Combined Test Result=Ratio Calprotectin if Ratio EDN<Ratio Calprotectin), the distributions showed in FIG. 10a were obtained. Only one IBD patient (CD case) out of 29 could not be identified using the combined test, which demonstrated performance improvement for both CD detection (FIG. 10b shows sensitivity of 92.9% and specificity of 100% for CD) and IBD detection (FIG. 10d shows sensitivity of 96.6% and specificity of 100% for IBD). 100% sensitivity and specificity were obtained when the combined test was applied for UC detection (FIG. 10c).

The outcome of the combined test (see FIG. 10a) also allowed concluding that test results among patients with UC tended to be higher than in CD cases. The difference between the two subgroups of IBD patients became greater when results of ICAM1 measurement were taken into account. FIG. 11a shows a modification of combined test results when an additional multiplier=0.1 was introduced in all cases when no detectable ICAM1 was found in the samples (i.e. ICAM1-Corrected Combined Test Result=Combined Test Result if ICAM1 concentration >0 and ICAM1-Corrected Combined Test Result=Combined Test Result×0.1 if ICAM1 concentration=0). ROC curve analysis assessing sensitivity and specificity of the ICAM1-corrected combined test for discriminating UC from CD is shown in FIG. 11b The test allowed to achieve 66.7% sensitivity and 100% specificity at cut-off point=9.0 (area under the curve=0.919).

Application of protein biomarker measurements in samples of colorectal mucocellular layer obtained using our procedure also allowed assessing inflammation intensity and the extent of colonic epithelium damage/healing during IBD therapy. This approach is exemplified by FIGS. 12 & 13.

FIG. 12a demonstrates EDN concentration measurements made at different time points following treatment initiation in four IBD patients responding well to applied therapy. In all these cases EDN concentrations visibly decreased by day 30 or 60. EDN change patterns in other four patients who did not respond to applied therapeutic interventions are shown in FIG. 12b. In these cases EDN levels remain high or even grow indicating the necessity of correcting therapeutic schemes. In particular, late increase of EDN concentration in patient #5 is likely to be an early manifestation of a new relapse (flare-up) of the disease. Patterns obtained in these patients for other inflammation markers (calprotectin, S100A12, ICAM1) were generally similar.

The same cases are presented in FIGS. 13a and 13b, but for soluble cytokeratin 18 assay, which reflects the degree of colonic mucosa damage (the test specifically detects epithelial cell death). Patterns of changes in CK-18 concentrations generally correlate with EDN changes demonstrating parallelism between colonic inflammation intensity and associated mucosal damage.

Additional analyses of D-dimer concentrations in the collected samples (not shown) suggested that this marker may be useful for detecting the presence of chronic internal bleeding in some cases. Further exploration of this biomarker can help individualising and refining relevant therapeutic schemes.

The use of biomarkers detectable in colonic mucocellular layer samples for therapy efficiency assessment and patient monitoring purposes requires repeated material collections from the same patient providing material for analysis at different time points. Given that the variability of biomarker concentrations among subjects affected with IBD is very high, it appears that comparison of results obtained at different time points and presented as a sequential dynamic curve against therapeutic/clinical parameters should preferably be applied on the individual basis. It might, however, be possible to work out a system of thresholds (cut-off points) for different IBD types (e.g. UC and CD), different inflammation localisations (proximal, distal, pancolitis) and different degrees of IBD severity.

Total protein amount and GAPDH concentration were also detected in the mucocellular layer samples from these patients and controls in order to assess the necessity of introducing a reference assay for the quantitative methods presented above. No correlation between results of these assays and subjects' diagnoses could be found. Total protein assay results were not informative, being influenced by variability of faecal contamination present in some samples. GAPDH concentrations were very low in most samples from all groups and could not be employed as a useful reference standard. At the same time results obtained for EDN, calprotectin, S100A12, ICAM1 and CK-18 (see FIGS. 4-13) provided good diagnostic performance without introducing additional reference standards.

Presented evidence allows concluding that the invention described in this document provides a new family of methods for inflammatory bowel disease diagnosis and colon inflammation intensity evaluation. The invented methods are based upon quantification of a range of biomarkers in non-invasively collected samples of colonic mucocellular layer. Diagnostic applications of the invented methods comprise: IBD detection, IBD differentiation from non-inflammatory conditions with similar clinical manifestations (in particular IBS) and differentiation between different forms of IBD (UC vs CD). All diagnostic applications are based on collecting and analysing a single sample or a set of samples within a short period of time (e.g. a single defaecation or all bowel movements within 24 hours). The diagnostic tests applied to these samples are designed on the basis of comparing obtained quantitative results against chosen concentration (or activity) thresholds (cut-off points) delimiting positive (i.e. likely to be associated with the presence of the disease) results above the threshold and negative (i.e. likely to be associated with the absence of the disease) results below or equal to the threshold. Applications of the invented methods related to colon inflammation intensity evaluation are based upon repeated collection and analysis of samples performed at different time points over an extended period of time (e.g. therapy course or long-term monitoring of IBD patients in remission). The resulting sequence of test outcomes permits: evaluation of changes in the severity of inflammation as well as related mucosal damage and internal bleeding, assessment of the efficiency of applied therapy and early detection of new IBD flare-ups extremely useful for long-term monitoring of IBD patients in remission. In addition, the approach proposed by the invention can be highly efficient in helping to individualise IBD therapy through determining specific subsets of IBD patients requiring different therapeutic strategies. For example, ICAM-1 quantification (by a single test) can help identifying patients who are likely to respond to already existing therapeutic agents targeting ICAM-1 expression such as alicaforsen (Miner et al, 2006; Vainer, 2010). Likewise, detection of high levels of soluble CK18 can indicate extensive epithelial damage in an IBD patient and help appropriately adjusting applied therapeutic procedures.

It can also be concluded that it may be possible to use biomarkers described in this invention as a biomarker panel for a complete characterisation of an individual with suspected IBD in order to determine the precise diagnosis and work out the most preferable therapeutic strategy. This constitutes the eighth key element of the new method.

The invention claimed is:

1. A method for diagnosing an inflammatory bowel disease (IBD), the method comprising:
   detecting the concentration of at least one IBD-specific biomarker in a sample of the colonic mucocellular layer obtained from a subject, wherein the sample is obtained from the surface of the anal area following defecation prior to cleaning the anal area;
   comparing said concentration to a threshold value; and
   determining that the subject has IBD when the concentration of at least one IBD-specific biomarker in said sample is equal to or greater than the threshold value wherein the subject is a human, and wherein the at least one IB-specific biomarker is selected from the group consisting of eosinophil-derived neurotoxin (EDN), calprotectin, S100A12 and ICAM1.

2. The method of claim 1, wherein the sample is taken from the anal area in the vicinity of the exterior opening of the anal canal.

3. The method of claim 1, wherein the threshold value is determined by determining the concentration of said IBD-specific biomarker in a group of one or more control subjects.

4. The method of claim 1, wherein said threshold value defines a fractile of a distribution of measured concentrations for a population of control subjects without IBD.

5. The method of claim 4, wherein said fractile is a 0.9 or greater fractile.

6. The method of claim 5, wherein said distribution is assumed to be a Gaussian distribution.

7. The method of claim 1, wherein said threshold value identifies that said subject is IBD-positive with greater than a threshold value.

8. The method of claim 1, wherein said threshold value is associated with a defined probability of determining that said subject has IBD, when said subject has IBD.

9. The method of claim 8, wherein said defined probability is greater than 60%.

10. The method of claim 1, wherein said IBD-specific biomarker is EDN the threshold value is, or is equivalent to, between 15 ng/ml and 35 ng/ml when the collected sample is lysed in 3 ml of lysis buffer.

11. The method of claim 1, wherein said IBD-specific biomarker is calprotectin the threshold value is, or is equivalent to, between 3.5 µg/ml and 6.0 µg/ml when the collected sample is lysed in 3 ml of lysis buffer.

12. The method of claim 1, wherein said IBD-specific biomarker is S100A12 the threshold value is, or is equivalent to, 50 ng/ml when the collected sample is lysed in 3 ml of lysis buffer.

13. The method of claim 1, wherein said IBD-specific biomarker is ICAM1 the threshold value is, or is equivalent to, 150 pg/ml when the collected sample is lysed in 3 ml of lysis buffer.

14. The method of claim 1, wherein the concentration of the IBD-specific biomarker is determined by contacting the sample with at least one antibody capable of specifically binding the IBD-specific biomarker or a fragment or variant thereof.

15. A method for diagnosing an inflammatory bowel disease (IBD), the method comprising:
   collecting a sample of intestinal or bowel cells or cell fragments comprising taking a swab of mucocellular layer material that originates from said bowel or intestine and is excreted during defecation from the exterior opening of the anal area in the vicinity of the exterior opening of the anal canal, wherein said swab is taken following defecation;
   collecting the sample of intestinal or bowel cells or cell fragments from the swab of mucocellular layer material, wherein collecting includes transferring the sample of intestinal or bowel cells or cell fragments from the swab of mucocellular layer material into a medium for lysis;
   detecting the concentration of at least one IBD-specific biomarker in the sample of the colonic mucocellular layer obtained from a subject;
   comparing said concentration to a threshold value; and
   determining that the subject has IBD when the concentration of at least one IBD-specific biomarker in said sample is equal to or greater than the threshold value; and wherein the subject is a human, and wherein the at least one IB-specific biomarker is selected from the group consisting of eosinophil-derived neurotoxin (EDN), calprotectin, S100A12 and ICAM1.

* * * * *

SEQUENCE LISTING

```
<160> NUMBER OF SEQ ID NOS: 5

<210> SEQ ID NO 1
<211> LENGTH: 161
<212> TYPE: PRT
<213> ORGANISM: Homo sapiens

<400> SEQUENCE: 1

Met Val Pro Lys Leu Phe Thr Ser Gln Ile Cys Leu Leu Leu Leu
1               5                   10                  15

Gly Leu Leu Ala Val Glu Gly Ser Leu His Val Lys Pro Pro Gln Phe
                20                  25                  30

Thr Trp Ala Gln Trp Phe Glu Thr Gln His Ile Asn Met Thr Ser Gln
            35                  40                  45

Gln Cys Thr Asn Ala Met Gln Val Ile Asn Asn Tyr Gln Arg Arg Cys
        50                  55                  60

Lys Asn Gln Asn Thr Phe Leu Leu Thr Thr Phe Ala Asn Val Val Asn
65                  70                  75                  80

Val Cys Gly Asn Pro Asn Met Thr Cys Pro Ser Asn Lys Thr Arg Lys
                85                  90                  95

Asn Cys His His Ser Gly Ser Gln Val Pro Leu Ile His Cys Asn Leu
                100                 105                 110

Thr Thr Pro Ser Pro Gln Asn Ile Ser Asn Cys Arg Tyr Ala Gln Thr
            115                 120                 125

Pro Ala Asn Met Phe Tyr Ile Val Ala Cys Asp Asn Arg Asp Gln Arg
        130                 135                 140

Arg Asp Pro Pro Gln Tyr Pro Val Val Pro Val His Leu Asp Arg Ile
145                 150                 155                 160

Ile

<210> SEQ ID NO 2
<211> LENGTH: 93
<212> TYPE: PRT
<213> ORGANISM: Homo sapiens

<400> SEQUENCE: 2

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60
```

```
Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90
```

<210> SEQ ID NO 3
<211> LENGTH: 114
<212> TYPE: PRT
<213> ORGANISM: Homo sapiens

<400> SEQUENCE: 3

```
Met Thr Cys Lys Met Ser Gln Leu Glu Arg Asn Ile Glu Thr Ile Ile
  1               5                  10                  15

Asn Thr Phe His Gln Tyr Ser Val Lys Leu Gly His Pro Asp Thr Leu
                 20                  25                  30

Asn Gln Gly Glu Phe Lys Glu Leu Val Arg Lys Asp Leu Gln Asn Phe
             35                  40                  45

Leu Lys Lys Glu Asn Lys Asn Glu Lys Val Ile Glu His Ile Met Glu
 50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                 85                  90                  95

Gly Asp Glu Gly Pro Gly His His Lys Pro Gly Leu Gly Glu Gly
            100                 105                 110

Thr Pro
```

<210> SEQ ID NO 4
<211> LENGTH: 92
<212> TYPE: PRT
<213> ORGANISM: Homo sapiens

<400> SEQUENCE: 4

```
Met Thr Lys Leu Glu Glu His Leu Glu Gly Ile Val Asn Ile Phe His
  1               5                  10                  15

Gln Tyr Ser Val Arg Lys Gly His Phe Asp Thr Leu Ser Lys Gly Glu
                 20                  25                  30

Leu Lys Gln Leu Leu Thr Lys Glu Leu Ala Asn Thr Ile Lys Asn Ile
             35                  40                  45

Lys Asp Lys Ala Val Ile Asp Glu Ile Phe Gln Gly Leu Asp Ala Asn
 50                  55                  60

Gln Asp Glu Gln Val Asp Phe Gln Glu Phe Ile Ser Leu Val Ala Ile
 65                  70                  75                  80

Ala Leu Lys Ala Ala His Tyr His Thr His Lys Glu
                 85                  90
```

<210> SEQ ID NO 5
<211> LENGTH: 532
<212> TYPE: PRT
<213> ORGANISM: Homo sapiens

<400> SEQUENCE: 5

```
Met Ala Pro Ser Ser Pro Arg Pro Ala Leu Pro Ala Leu Leu Val Leu
  1               5                  10                  15

Leu Gly Ala Leu Phe Pro Gly Pro Gly Asn Ala Gln Thr Ser Val Ser
                 20                  25                  30

Pro Ser Lys Val Ile Leu Pro Arg Gly Gly Ser Val Leu Val Thr Cys
```

```
                35                  40                  45
Ser Thr Ser Cys Asp Gln Pro Lys Leu Leu Gly Ile Glu Thr Pro Leu
         50                  55                  60

Pro Lys Lys Glu Leu Leu Leu Pro Gly Asn Asn Arg Lys Val Tyr Glu
 65                  70                  75                  80

Leu Ser Asn Val Gln Glu Asp Ser Gln Pro Met Cys Tyr Ser Asn Cys
                 85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460
```

```
Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
            515                 520                 525

Ala Thr Pro Pro
530
```